(12) United States Patent
Greenberg et al.

(10) Patent No.: US 12,133,793 B2
(45) Date of Patent: *Nov. 5, 2024

(54) ENDOLUMINAL PROSTHESIS HAVING MULTIPLE BRANCHES OR FENESTRATIONS AND METHODS OF DEPLOYMENT

(71) Applicants: Cook Medical Technologies LLC, Bloomington, IN (US); The Cleveland Clinic Foundation, Cleveland, OH (US)

(72) Inventors: Roy K. Greenberg, Bratenahl, OH (US); Karl J. West, Geneva, OH (US); Timothy A. Resch, Lund (SE); Blayne A. Roeder, Bloomington, IN (US)

(73) Assignees: Cook Medical Technologies LLC, Bloomington, IN (US); The Cleveland Clinic Foundation, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 18/185,928

(22) Filed: Mar. 17, 2023

(65) Prior Publication Data

US 2023/0293284 A1     Sep. 21, 2023

Related U.S. Application Data

(63) Continuation of application No. 16/938,232, filed on Jul. 24, 2020, now Pat. No. 11,607,304, which is a
(Continued)

(51) Int. Cl.
*A61F 2/07*     (2013.01)
*A61F 2/06*     (2013.01)
(Continued)

(52) U.S. Cl.
CPC ............ *A61F 2/07* (2013.01); *A61F 2/06* (2013.01); *A61F 2/82* (2013.01); *A61F 2/86* (2013.01);
(Continued)

(58) Field of Classification Search
CPC ...... A61F 2/06; A61F 2/07; A61F 2/82; A61F 2/86; A61F 2/89; A61F 2/95; A61F 2/954;
(Continued)

(56) References Cited

U.S. PATENT DOCUMENTS 5,387,235 A    2/1995    Chuter
5,425,765 A    6/1995    Tiefenbrun et al.
(Continued)

FOREIGN PATENT DOCUMENTS

WO      WO 99/11198 A1     3/1999
WO   WO 2000/0025847      5/2000
(Continued)

OTHER PUBLICATIONS

Partial European Search Report, dated Dec. 14, 2012, pp. 1-6, European Patent Application No. 12164809.1, European Patent Office, The Netherlands.
(Continued)

*Primary Examiner* — Ryan J. Severson
(74) *Attorney, Agent, or Firm* — Crowell & Moring LLP

(57) ABSTRACT

A branched and fenestrated prosthesis may include a main tubular graft body including a proximal end opening, a distal end opening, a lumen, and a sidewall. A branch may extend from the sidewall and may include a first end opening, a second end opening, and a lumen. A fenestration may be disposed in the sidewall and positioned distal of the second
(Continued)

end opening of the branch. The branched and fenestrated prosthesis may include a plurality of branches and a plurality of fenestrations.

20 Claims, 38 Drawing Sheets

Related U.S. Application Data continuation of application No. 15/888,710, filed on Feb. 5, 2018, now Pat. No. 10,722,342, which is a continuation of application No. 14/873,799, filed on Oct. 2, 2015, now Pat. No. 9,883,938, which is a continuation of application No. 13/457,092, filed on Apr. 26, 2012, now Pat. No. 9,149,382.

(60) Provisional application No. 61/581,475, filed on Dec. 29, 2011, provisional application No. 61/526,061, filed on Aug. 22, 2011, provisional application No. 61/480,091, filed on Apr. 28, 2011.

(51) Int. Cl.
| | |
|---|---|
| A61F 2/82 | (2013.01) |
| A61F 2/86 | (2013.01) |
| A61F 2/95 | (2013.01) |
| A61F 2/954 | (2013.01) |
| A61F 2/962 | (2013.01) |
| A61F 2/89 | (2013.01) |
| A61F 2/966 | (2013.01) |

(52) U.S. Cl.
CPC .......... *A61F 2/95* (2013.01); *A61F 2/954* (2013.01); *A61F 2/962* (2013.01); *A61F 2002/061* (2013.01); *A61F 2002/072* (2013.01); *A61F 2002/075* (2013.01); *A61F 2002/821* (2013.01); *A61F 2002/826* (2013.01); *A61F 2/89* (2013.01); *A61F 2002/9665* (2013.01); *A61F 2220/0075* (2013.01); *A61F 2230/0091* (2013.01); *A61F 2250/0007* (2013.01); *A61F 2250/0017* (2013.01); *A61F 2250/0018* (2013.01); *A61F 2250/0039* (2013.01)

(58) Field of Classification Search
CPC .......... A61F 2/962; A61F 2002/061; A61F 2002/072; A61F 2002/9665; A61F 2220/0075; A61F 2250/0039
See application file for complete search history.

(56) References Cited

U.S. PATENT DOCUMENTS

| | | | |
|---|---|---|---|
| 5,445,600 A | 8/1995 | Abdulla | |
| 5,609,627 A | 3/1997 | Goicoechea et al. | |
| 5,628,783 A | 5/1997 | Quiachon et al. | |
| 5,676,696 A | 10/1997 | Marcade | |
| 5,676,697 A | 10/1997 | McDonald | |
| 5,720,776 A | 2/1998 | Chuter et al. | |
| 5,746,766 A | 5/1998 | Edoga | |
| 5,776,142 A | 7/1998 | Gunderson | |
| 5,824,055 A | 10/1998 | Spiridigliozzi et al. | |
| 5,948,017 A | 9/1999 | Taheri | |
| 5,984,955 A | 11/1999 | Wisselink | |
| 6,019,788 A | 2/2000 | Butters et al. | |
| 6,099,548 A | 8/2000 | Taheri | |
| 6,106,549 A | 8/2000 | Taheri | |
| 6,143,002 A | 11/2000 | Vietmeier | |
| 6,187,033 B1 | 2/2001 | Schmitt et al. | |
| 6,206,931 B1 | 3/2001 | Cook et al. | |
| 6,210,429 B1 | 4/2001 | Vardi et al. | |
| 6,287,315 B1 | 9/2001 | Wijeratne et al. | |
| 6,478,813 B1 | 11/2002 | Keith et al. | |
| 6,478,817 B2 | 11/2002 | Schmitt et al. | |
| 6,524,335 B1 | 2/2003 | Hartley et al. | |
| 6,576,009 B2 | 6/2003 | Ryan et al. | |
| 6,645,242 B1 | 11/2003 | Quinn | |
| 6,663,666 B1 | 12/2003 | Quiachon et al. | |
| 6,695,875 B2 | 2/2004 | Stelter et al. | |
| 6,723,116 B2 | 4/2004 | Taheri | |
| 6,793,672 B2 | 9/2004 | Khosravi et al. | |
| 6,814,752 B1 | 11/2004 | Chuter | |
| 6,827,726 B2 | 12/2004 | Parodi | |
| 6,827,735 B2 | 12/2004 | Greenberg | |
| 6,849,087 B1 | 2/2005 | Chuter | |
| 6,852,116 B2 | 2/2005 | Leonhardt et al. | |
| 6,918,925 B2 | 7/2005 | Tehrani | |
| 6,939,370 B2 | 9/2005 | Hartley et al. | |
| 6,974,471 B2 | 12/2005 | Van Schie et al. | |
| 7,014,653 B2 | 3/2006 | Ouriel et al. | |
| 7,105,020 B2 | 9/2006 | Greenberg et al. | |
| 7,108,715 B2 | 9/2006 | Lawrence-Brown et al. | |
| 7,144,421 B2 | 12/2006 | Carpenter et al. | |
| 7,169,176 B2 | 1/2007 | Lauterjung | |
| 7,232,459 B2 | 6/2007 | Greenberg et al. | |
| 7,235,095 B2 | 6/2007 | Haverkost et al. | |
| 7,238,198 B2 | 7/2007 | Hartley et al. | |
| 7,294,147 B2 | 11/2007 | Hartley | |
| 7,306,623 B2 | 12/2007 | Watson | |
| 7,407,509 B2 | 8/2008 | Greenberg et al. | |
| 7,413,573 B2 | 8/2008 | Hartley et al. | |
| 7,435,253 B1 | 10/2008 | Hartley et al. | |
| 7,445,610 B2 | 11/2008 | Adams et al. | |
| 7,537,606 B2 | 5/2009 | Hartley et al. | |
| 7,550,004 B2 | 6/2009 | Bahler et al. | |
| 7,645,298 B2 | 1/2010 | Hartley et al. | |
| 7,670,369 B2 | 3/2010 | Schaeffer | |
| 7,699,883 B2 | 4/2010 | Douglas | |
| 7,771,462 B1 | 8/2010 | Davidson et al. | |
| 7,806,917 B2 | 10/2010 | Xiao | |
| 7,828,837 B2 | 11/2010 | Khoury | |
| 7,833,259 B2 | 11/2010 | Boatman | |
| 7,862,604 B1 | 1/2011 | Marcade et al. | |
| 7,887,576 B2 | 2/2011 | Bahler et al. | |
| 7,914,572 B2 | 3/2011 | Hartley et al. | |
| 7,927,367 B2 | 4/2011 | Chuter | |
| 7,998,186 B2 | 8/2011 | Hartley | |
| 8,043,363 B2 | 10/2011 | Schaeffer | |
| 8,226,706 B2 | 7/2012 | Hartley et al. | |
| 8,394,136 B2 | 3/2013 | Hartley et al. | |
| 8,672,993 B2 | 3/2014 | Chuter et al. | |
| 8,758,425 B2 | 6/2014 | Greenberg et al. | |
| 8,771,336 B2 | 7/2014 | Roeder | |
| 8,795,349 B2 | 8/2014 | Huser et al. | |
| 8,808,351 B2 | 8/2014 | Osborne | |
| 8,808,355 B2 | 8/2014 | Barrand | |
| 8,870,939 B2 | 10/2014 | Roeder et al. | |
| 8,894,701 B2 | 11/2014 | Vad | |
| 8,906,086 B2 | 12/2014 | Roeder et al. | |
| 8,915,956 B2 | 12/2014 | Schaeffer et al. | |
| 8,992,593 B2 | 3/2015 | Chuter et al. | |
| 9,005,268 B2 | 4/2015 | Hartley et al. | |
| 9,005,271 B2 | 4/2015 | Ivancev et al. | |
| 9,011,517 B2 | 4/2015 | Hartley et al. | |
| 9,034,027 B2 | 5/2015 | Ivancev | |
| 9,060,887 B2 | 6/2015 | Hartley et al. | |
| 9,072,621 B2 | 7/2015 | Hartley et al. | |
| 9,078,780 B2 | 7/2015 | Schaeffer et al. | |
| 9,095,456 B2 | 8/2015 | Ivancev et al. | |
| 9,095,458 B2 | 8/2015 | Hartley et al. | |
| 9,095,461 B2 | 8/2015 | Schaeffer | |
| 9,101,455 B2 | 8/2015 | Roeder et al. | |
| 9,101,456 B2 | 8/2015 | Hartley et al. | |
| 9,107,741 B2 | 8/2015 | Bui et al. | |
| 9,149,355 B2 | 10/2015 | Hartley | |
| 9,149,382 B2 | 10/2015 | Greenberg et al. | |
| 9,155,611 B2 | 10/2015 | Sun | |
| 9,277,984 B2 | 3/2016 | Huser et al. | |
| 9,351,822 B2 | 5/2016 | Roeder | |
| 9,439,793 B2 | 9/2016 | Roeder | |

(56) References Cited

U.S. PATENT DOCUMENTS

| | | |
|---|---|---|
| 9,724,187 B2 * | 8/2017 | Ivancev .................. A61F 2/95 |
| 9,883,938 B2 | 2/2018 | Greenberg |
| 10,105,245 B2 * | 10/2018 | Ondersma ............... A61F 2/856 |
| 10,137,018 B2 * | 11/2018 | Samuels .................. A61F 2/07 |
| 10,722,342 B2 * | 7/2020 | Greenberg ............... A61F 2/86 |
| 11,607,304 B2 * | 3/2023 | Greenberg ............... A61F 2/95 |
| 2001/0012943 A1 | 8/2001 | Shaolian et al. |
| 2001/0012962 A1 | 8/2001 | Schmitt et al. |
| 2001/0049534 A1 | 12/2001 | Lachat |
| 2002/0045930 A1 | 4/2002 | Burg et al. |
| 2003/0088305 A1 | 5/2003 | Van Schie et al. |
| 2003/0120332 A1 | 6/2003 | Hartley |
| 2003/0199967 A1 | 10/2003 | Hartley et al. |
| 2003/0233140 A1 | 12/2003 | Hartley et al. |
| 2004/0073289 A1 | 4/2004 | Hartley |
| 2004/0098079 A1 | 5/2004 | Hartley et al. |
| 2004/0098084 A1 | 5/2004 | Hartley et al. |
| 2004/0106972 A1 | 6/2004 | Deaton |
| 2004/0106978 A1 | 6/2004 | Greenberg et al. |
| 2004/0215327 A1 | 10/2004 | Doig et al. |
| 2005/0102018 A1 | 5/2005 | Carpenter et al. |
| 2005/0102021 A1 | 5/2005 | Osborne |
| 2005/0131518 A1 | 6/2005 | Hartley et al. |
| 2005/0149166 A1 | 7/2005 | Schaeffer et al. |
| 2005/0171597 A1 | 8/2005 | Boatman et al. |
| 2005/0171598 A1 | 8/2005 | Schaeffer |
| 2005/0182476 A1 | 8/2005 | Hartley et al. |
| 2005/0222668 A1 | 10/2005 | Schaeffer et al. |
| 2005/0222669 A1 | 10/2005 | Purdy |
| 2005/0222672 A1 | 10/2005 | Shmulewitz |
| 2005/0273155 A1 | 12/2005 | Bahler et al. |
| 2006/0004433 A1 | 1/2006 | Greenberg et al. |
| 2006/0058864 A1 | 3/2006 | Schaeffer et al. |
| 2006/0089704 A1 | 4/2006 | Douglas |
| 2006/0184228 A1 | 8/2006 | Khoury |
| 2006/0229707 A1 | 10/2006 | Khoury |
| 2007/0043425 A1 | 2/2007 | Hartley et al. |
| 2007/0083215 A1 | 4/2007 | Hamer et al. |
| 2007/0142896 A1 | 6/2007 | Anderson et al. |
| 2007/0219614 A1 | 9/2007 | Hartley |
| 2007/0219621 A1 | 9/2007 | Hartley et al. |
| 2007/0233220 A1 | 10/2007 | Greenan |
| 2007/0244547 A1 | 10/2007 | Greenan |
| 2007/0250154 A1 | 10/2007 | Greenberg et al. |
| 2007/0299499 A1 | 12/2007 | Hartley et al. |
| 2008/0114438 A1 | 5/2008 | Hartley et al. |
| 2008/0255581 A1 | 10/2008 | Bourang et al. |
| 2008/0294234 A1 | 11/2008 | Hartley et al. |
| 2009/0030502 A1 | 1/2009 | Sun et al. |
| 2009/0048663 A1 | 2/2009 | Greenberg |
| 2009/0099648 A1 | 4/2009 | Yu |
| 2009/0125098 A1 | 5/2009 | Chuter |
| 2009/0171438 A1 | 7/2009 | Chuter et al. |
| 2009/0182405 A1 | 7/2009 | Arnault de la Menardiere et al. |
| 2010/0023110 A1 | 1/2010 | Schaeffer |
| 2010/0063576 A1 | 3/2010 | Schaeffer et al. |
| 2010/0249899 A1 | 9/2010 | Chuter et al. |
| 2010/0268327 A1 | 10/2010 | Bruszewski et al. |
| 2011/0054594 A1 | 3/2011 | Mayberry et al. |
| 2011/0270376 A1 | 11/2011 | Hartley |
| 2012/0041535 A1 | 2/2012 | Huser et al. |
| 2012/0046728 A1 | 2/2012 | Huser et al. |
| 2012/0130472 A1 | 5/2012 | Shaw |
| 2012/0290069 A1 | 11/2012 | Ivancev et al. |
| 2012/0323303 A1 | 12/2012 | Ivancev |
| 2013/0013053 A1 | 1/2013 | Hartley et al. |
| 2013/0046371 A1 | 2/2013 | Greenberg et al. |
| 2013/0079870 A1 | 3/2013 | Roeder et al. |
| 2013/0138199 A1 | 5/2013 | Ivancev et al. |
| 2015/0034217 A1 | 2/2015 | Vad |
| 2015/0073534 A1 | 3/2015 | Roeder et al. |
| 2015/0112420 A1 | 4/2015 | Hartley et al. |
| 2015/0148890 A1 | 5/2015 | Hartley et al. |
| 2015/0230916 A1 | 8/2015 | Ivancev et al. |
| 2015/0305852 A1 | 10/2015 | Hartley et al. |
| 2015/0327983 A1 | 11/2015 | Roeder et al. |
| 2015/0374487 A1 | 12/2015 | Greenberg et al. |
| 2016/0022411 A1 | 1/2016 | Greenberg et al. |
| 2016/0106564 A1 | 4/2016 | Roeder et al. |
| 2016/0184081 A1 | 6/2016 | Huser et al. |
| 2018/0153680 A1 | 6/2018 | Greenberg |
| 2020/0352703 A1 * | 11/2020 | Greenberg ............... A61F 2/86 |

FOREIGN PATENT DOCUMENTS

| | | |
|---|---|---|
| WO | WO 2004/002365 A1 | 1/2004 |
| WO | WO 2004/002370 A1 | 1/2004 |
| WO | WO 2004/017867 A1 | 3/2004 |
| WO | WO 2004/017868 A1 | 3/2004 |
| WO | WO 2004/028399 A2 | 4/2004 |
| WO | WO 2005/034808 A1 | 4/2005 |
| WO | WO 2005/034810 A1 | 4/2005 |
| WO | WO 2008/007397 A1 | 1/2008 |
| WO | WO 2010/127040 A1 | 11/2010 |
| WO | WO 2011/047004 A1 | 4/2011 |
| WO | WO 2011/116308 A1 | 9/2011 |

OTHER PUBLICATIONS

Extended European Search Report, dated Apr. 16, 2013, pp. 1-14, European Patent Application No. 12164809.1, European Patent Office, The Netherlands.

International Search Report and Written Opinion of the International Searching Authority for PCT/US2010/052446, mailed Jan. 17, 2011 (13 pages).

Extended European Search Report, dated Mar. 5, 2014 for corresponding European Patent Application No. 13275292.4 (5 pages).

Communication pursuant to Article 94(3) EPC, dated Mar. 11, 2015 for corresponding European Patent Application No. 12164809.1 (7 pages).

European Search Report for EP Application No. 16162345.9, dated Jun. 6, 2016, 9 pages.

Examination for EP Application No. 16162345.9, dated Mar. 16, 2017, 7 pages.

Examination Report for European Patent Application No. 16162345.9 dated Jan. 15, 2018, 7 pages.

Extended European Search Report for European Patent Application No. 19190356.6, dated Nov. 27, 2019, 6 pages.

* cited by examiner

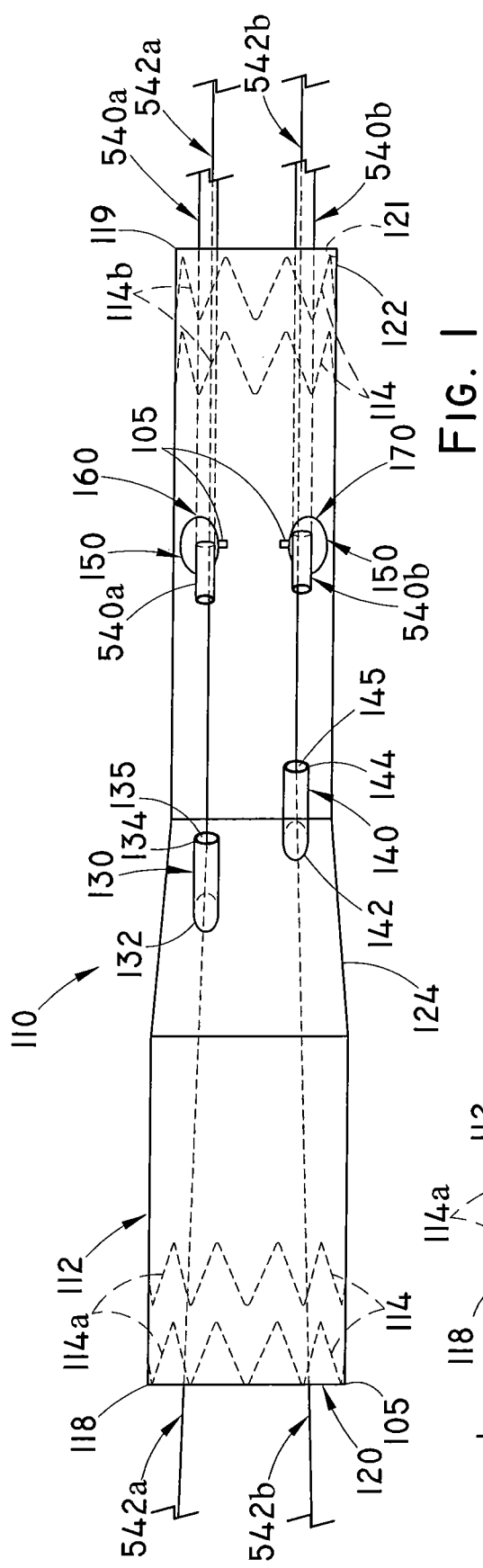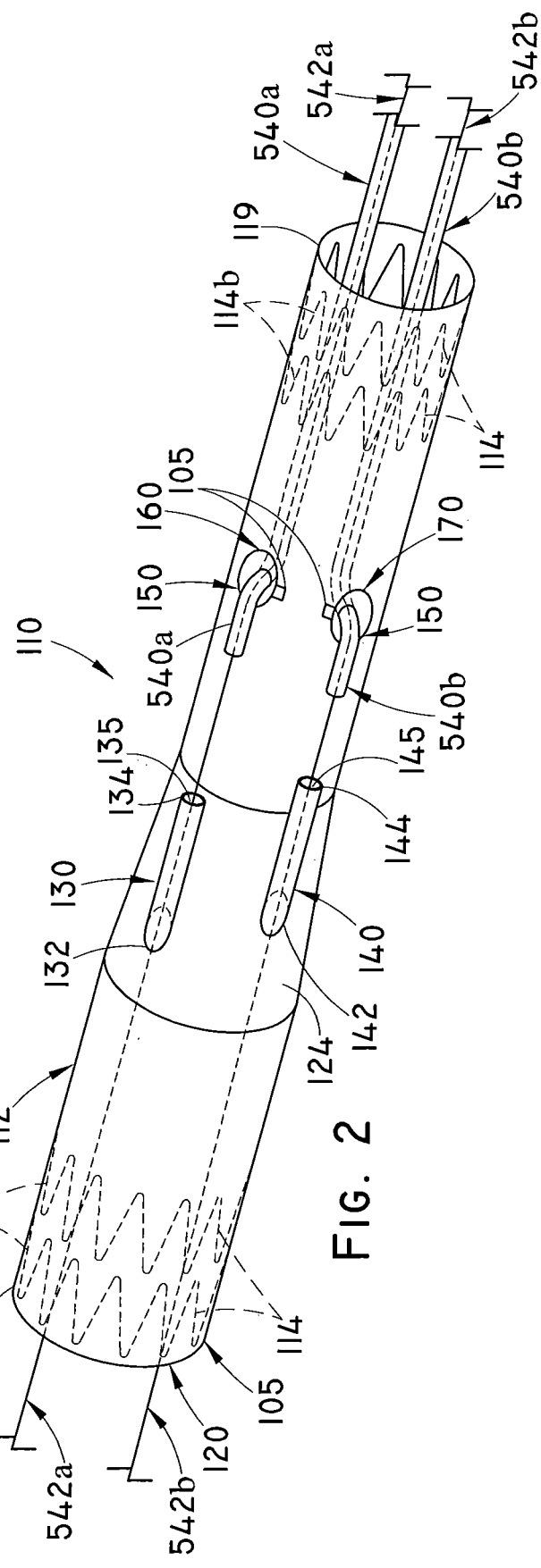

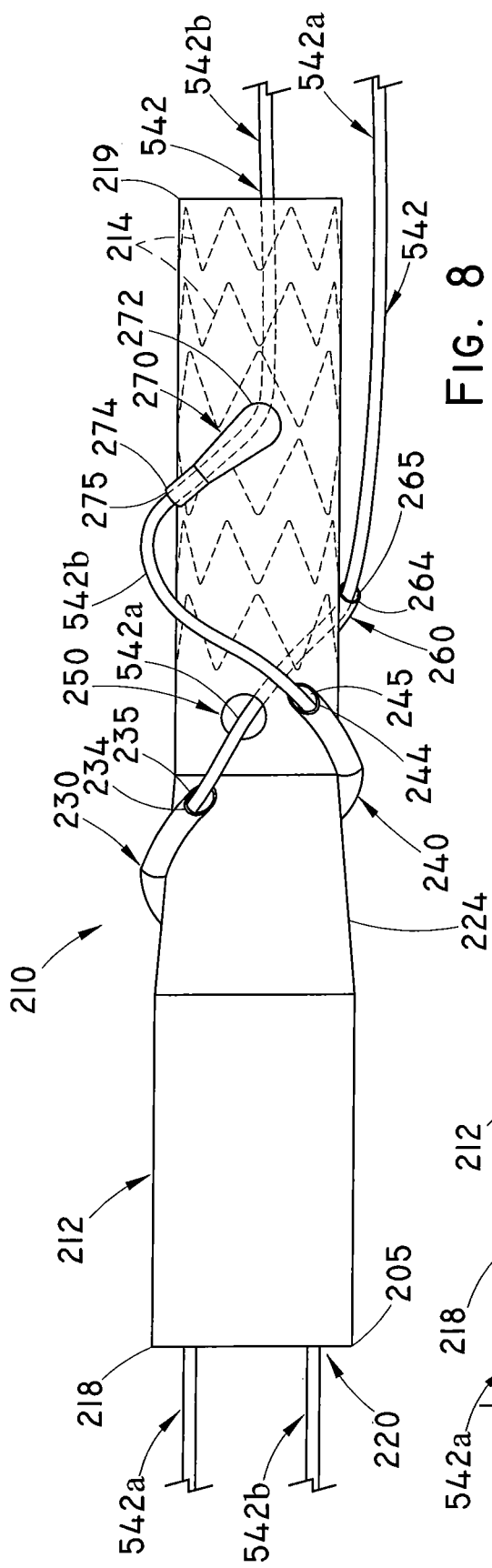
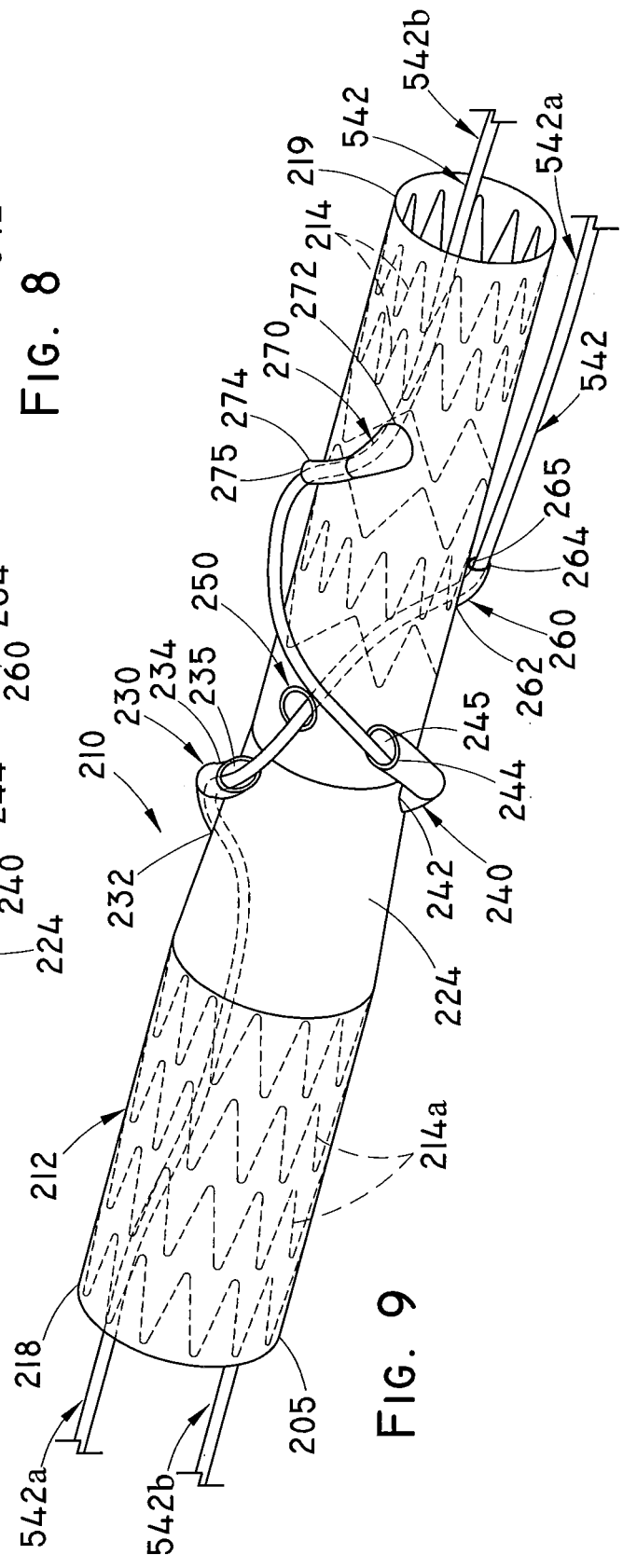
FIG. 8
FIG. 9

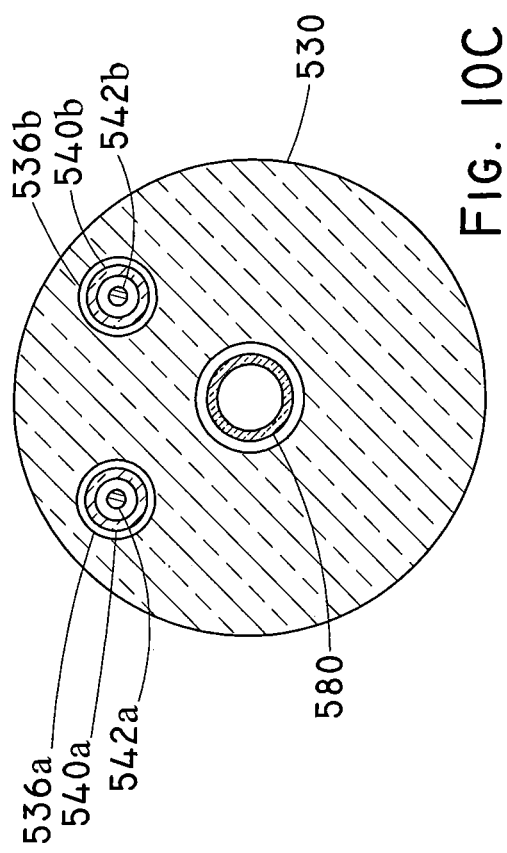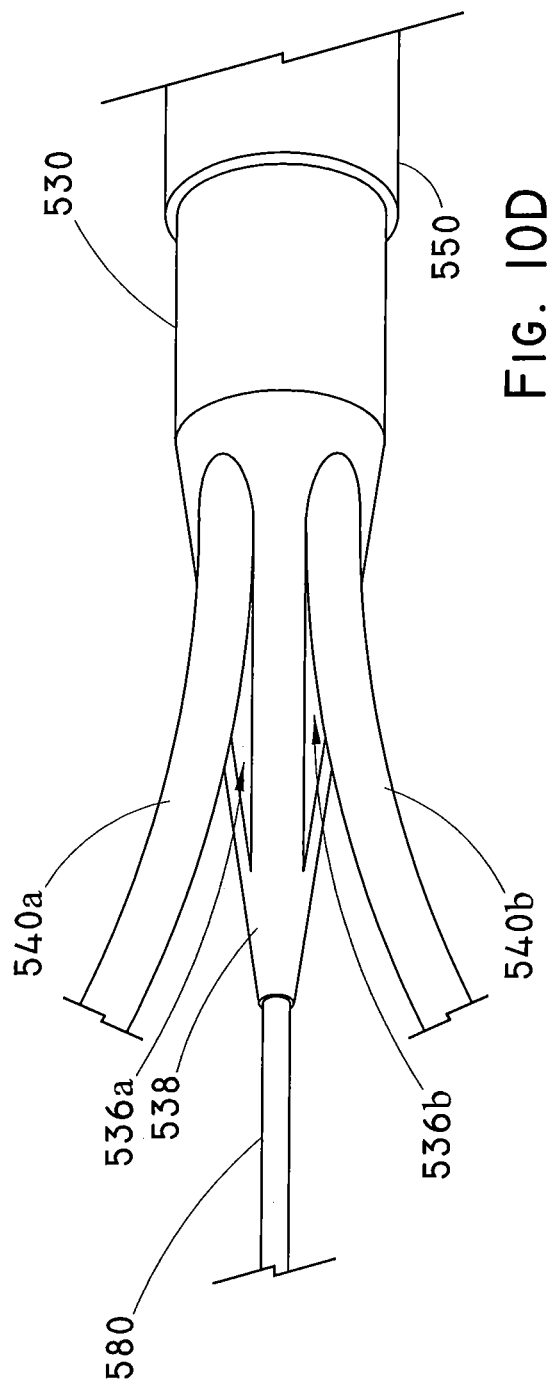

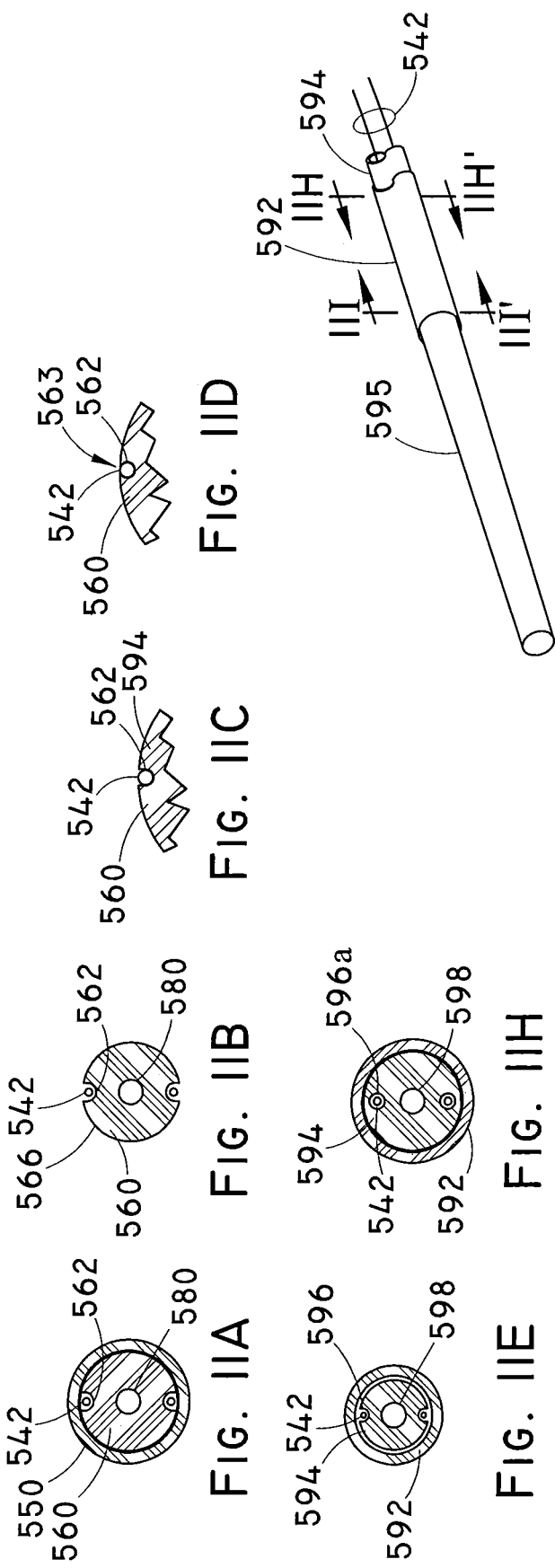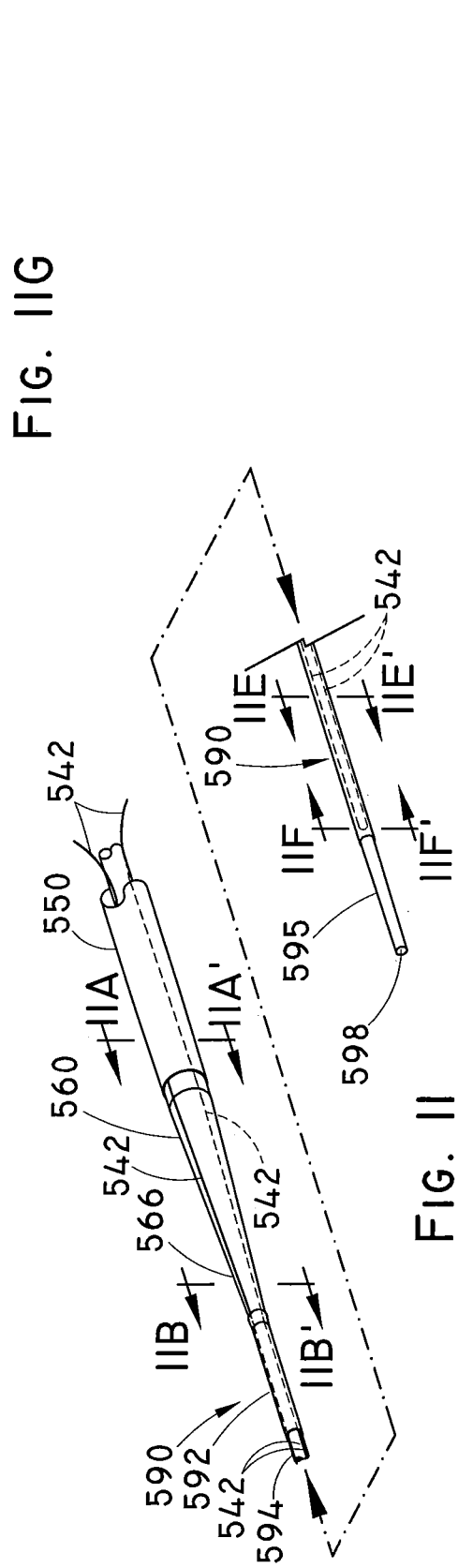

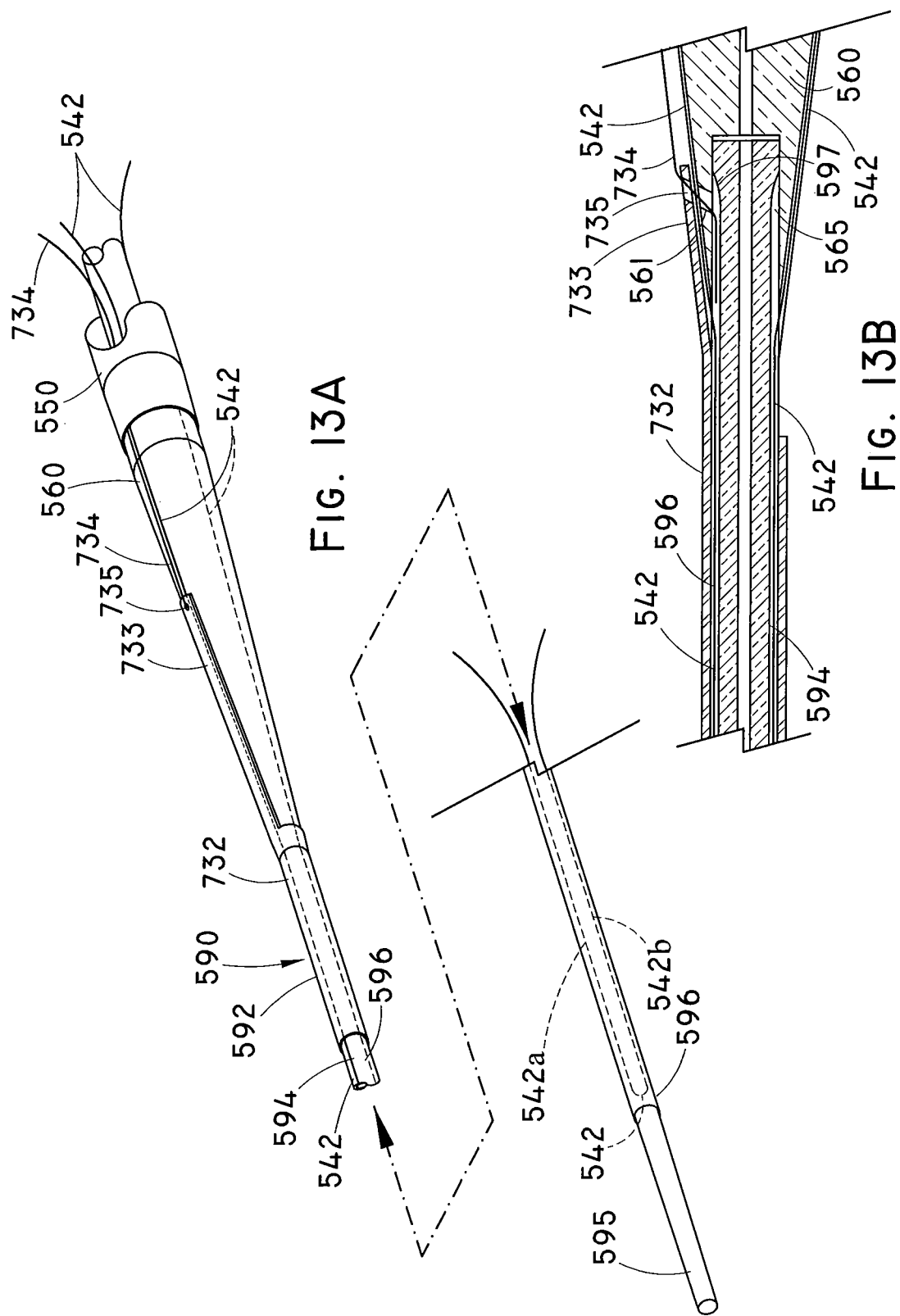

ENDOLUMINAL PROSTHESIS HAVING MULTIPLE BRANCHES OR FENESTRATIONS AND METHODS OF DEPLOYMENT

CROSS-REFERENCE TO RELATED APPLICATIONS

The patent application is a continuation of U.S. application Ser. No. 16/938,232, filed Jul. 24, 2020, which is a continuation of U.S. application Ser. No. 15/888,710, filed Feb. 5, 2018, now U.S. Pat. No. 10,722,342, which is a continuation of U.S. application Ser. No. 14/873,799, filed Oct. 2, 2015, now U.S. Pat. No. 9,883,938, which is a continuation of application Ser. No. 13/457,092, filed Apr. 26, 2012, now U.S. Pat. No. 9,149,382, which claims priority and the benefit of provisional U.S. Patent Application Ser. No. 61/480,091, filed Apr. 28, 2011, provisional U.S. Patent Application Ser. No. 61/526,061, filed Aug. 22, 2011, and provisional U.S. Patent Application Ser. No. 61/581,475, filed Dec. 29, 2011, all of which are incorporated herein by reference in their entireties.

TECHNICAL FIELD

This disclosure relates to endoluminal medical devices for implantation within the human or animal body for treatment of endovascular disease.

BACKGROUND

The present disclosure relates generally to medical devices. More particularly, it relates to an endoluminal prosthesis having multiple branches or fenestrations and systems and methods for facilitating deployment of such an endoluminal prosthesis.

Using stent grafts to treat aneurysms is common in the medical field. Stent grafts are deployed by accessing a vasculature with a small incision in the skin and guiding a delivery system to the target area. This intraluminal delivery is less invasive and generally preferred over more intrusive forms of surgery. Multiple stent grafts may be implanted using intraluminal delivery to provide a system of interconnected stent grafts. Interconnected stent grafts can be made of fenestrated stent grafts and smaller side branch grafts, including bifurcated components.

Sometimes aneurysms engulf a vessel and its branch vessels, such as the aorta and the renal arteries or the aortic arch and the branch arteries. In such instances, a fenestrated graft can be implanted in the main vessel while smaller branch grafts can be deployed in the branch arteries. The main vessel grafts have fenestrations that correspond with the openings of the branch vessels. The smaller branch grafts are joined with the main vessel graft at the fenestrations. Due to the torsion and rigors of the endovascular system, this juncture can be subject to significant stress.

Moreover, when a condition such as an aneurysm has engulfed a main vessel and multiple branch vessels, it may be relatively time consuming to deliver the smaller branch grafts needed in addition to the main graft. For example, insertion of wire guides and delivery devices may be time consuming and/or difficult to perform when multiple smaller branch grafts are deployed to cannulate multiple corresponding branch vessels.

SUMMARY

The present embodiments provide an endoluminal prosthesis having multiple branches or fenestrations and systems and methods for facilitating deployment of such an endoluminal prosthesis.

In one example, a system for facilitating deployment of an endoluminal prosthesis may include a main tubular graft body of a biocompatible material. The main tubular graft body may include a proximal end opening, a distal end opening, a lumen extending longitudinally between the proximal end opening and the distal end opening, and a sidewall. A branch may extend from the sidewall of the main tubular graft body. The branch may include a first end opening, a second end opening, and a lumen extending between the first end opening and the second end opening of the branch. A fenestration may be disposed in the sidewall and positioned distal of the second end opening of the branch. The system may include a wire segment including a proximal portion positioned proximal of the proximal end opening of the main tubular graft body and a distal portion positioned distal of the distal end opening of the main tubular graft body. The wire segment may extend through the fenestration and through the lumen of the branch in a preloaded configuration.

In another example, a system for treating a damaged body vessel may include a delivery device, an endoluminal prosthesis, and a wire segment. The delivery device may include a cannula including a guide wire lumen extending longitudinally within the cannula. The delivery device may include a catheter including a lumen extending longitudinally within the catheter. The cannula may be received within the lumen of the catheter. The delivery device may include an auxiliary sheath received within the lumen of the catheter and including a lumen extending longitudinally within the auxiliary sheath. The delivery device may include a length extending module extending from a proximal end of the cannula. The length extending module may be releasably coupled to the cannula. The prosthesis may be positioned on the cannula of the delivery device. The prosthesis may include a main tubular graft body including an open proximal end, an open distal end, a lumen extending longitudinally within the main tubular graft body and in fluid communication with each of the open proximal end and the open distal end, and a sidewall. The cannula of the delivery device may be received within the lumen of the main tubular graft body and each of the open proximal end and the open distal end. The prosthesis may include a first fenestration in the sidewall and a second fenestration in the sidewall. The second fenestration may be positioned distal of the first fenestration. The wire segment may extend within the lumen of the auxiliary sheath and through each of the first fenestration and the second fenestration of the prosthesis. A proximal end of the wire segment may be positioned near a proximal end of the length extending module. A distal end of the wire segment may be positioned distal of the distal end of the main tubular graft body.

In another example, a method of treating a damaged body vessel may include introducing a prosthesis endoluminally into the body vessel on a delivery device. The delivery device may include a tubular cannula. A dilator tip may be positioned at a proximal end of the cannula. A length extending module may extend from a proximal end of the dilator tip. A catheter may surround a portion of the cannula and include a lumen extending longitudinally within the catheter. The method may include severing an auxiliary guide wire to separate a first wire segment of the auxiliary guide wire from a second wire segment of the auxiliary guide wire. The method may include removing the length extending module from the dilator tip. The method may include tracking a first introducer in a distal to proximal longitudinal direction over the first wire segment and through a preloaded auxiliary sheath positioned within the lumen of the catheter to deploy a first delivery component in a fenestration of the prosthesis. The method may include tracking a second introducer in a proximal to distal longitudinal direction over the first wire segment to deploy a second delivery component in a branch of the prosthesis.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

FIG. 1 is a side view of one embodiment of an endoluminal prosthesis in a preloaded configuration.

FIG. 2 is a perspective view of the endoluminal prosthesis of FIG. 1.

FIG. 8 is a side view of another embodiment of an endoluminal prosthesis in a preloaded configuration.

FIG. 9 is a perspective view of the endoluminal prosthesis of FIG. 8.

FIG. 10C is a transverse cross-sectional view of the delivery device taken along line 10C-10C' of FIG. 10A.

FIG. 10D is a partial perspective view of the proximal end of a pusher catheter of the delivery device of FIG. 10A.

FIG. 11 is a perspective view of a proximal portion of the delivery device of FIG. 10A.

FIG. 11A is a transverse cross-sectional view of the delivery device taken along line 11A-11A' of FIG. 11.

FIG. 11B is a transverse cross-sectional view of the delivery device taken along line 11B-11B' of FIG. 11.

FIG. 11C depicts one embodiment of a longitudinal groove of a delivery device.

FIG. 11D depicts another embodiment of a longitudinal groove of a delivery device.

FIG. 11E is a transverse cross-sectional view of the delivery device taken along line 11E-11E' of FIG. 11.

FIG. 11G is a partial perspective view of a proximal portion of one embodiment of a length extending module of a delivery device.

FIG. 11H is a transverse cross-sectional view of the delivery device taken along line 11H-11H' of FIG. 11G.

FIG. 13A is a partial perspective view of one embodiment of a delivery device having a nose cone dilator and a length extending module.

FIG. 13B is a partial longitudinal cross-sectional view of the connection arrangement between the nose cone dilator and the length extending module of FIG. 13A.

DETAILED DESCRIPTION OF THE DRAWINGS AND THE PRESENTLY PREFERRED EMBODIMENTS

Figure 3:
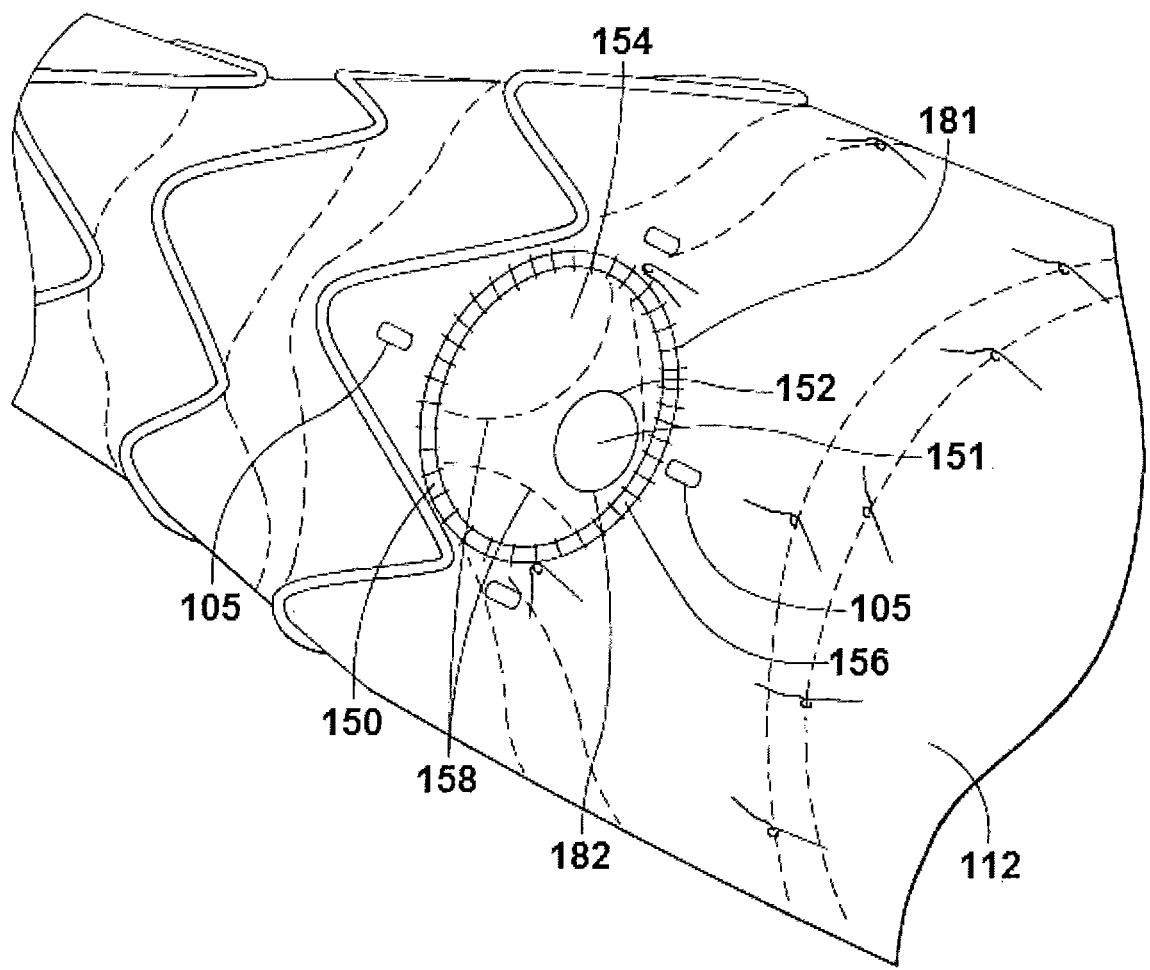
FIG. 3 depicts one embodiment of a pivot fenestration.

The present disclosure relates to an endoluminal prosthesis having multiple branches or fenestrations and systems and methods for facilitating deployment of such an endoluminal prosthesis. A side branch prosthesis may be deployed within each of the branches and/or fenestrations of the endoluminal prosthesis to enable fluid to flow from the endoluminal prosthesis into the branch vessels. The fenestrations may be configured as pivot fenestrations that are capable of pivoting as needed to accommodate the dynamic geometry of the branch vessels, such as the aortic branches. For example, in various aspects shown and described in more detail below, one or more pivot fenestrations of an endoluminal prosthesis may lie outside the surface plane of the body of the prosthesis. The pivot fenestration may allow a side branch prosthesis (e.g., a stent, a graft, or a stent-graft) deployed in the pivot fenestration to pivot into a variety of orientations to facilitate meeting and sealing of the side branch prosthesis with the branch vessel. The orientation of the pivot fenestrations may dynamically change over time to conform to changing anatomy.

In the present disclosure, the term "proximal" refers to a direction that is generally closest to the heart during a medical procedure, while the term "distal" refers to a direction that is farthest from the heart during a medical procedure.

The term "fenestration" refers to an opening provided through a surface of a prosthesis from the interior of the prosthesis to the exterior of the prosthesis. A fenestration may have a variety of geometries including circular, semicircular, oval, oblong, or other geometries.

FIGS. 1-2 depict one embodiment of a prosthesis 110, which may be configured as a stent graft. The prosthesis 110 may include a graft 112 which forms a main body of the prosthesis 110. The graft 112 may include a generally tubular body of a biocompatible material. The graft 112 may have a proximal end 118, a distal end 119, and a lumen 120 extending longitudinally within the graft 112 between the proximal end 118 and the distal end 119. The lumen 120 may be configured to enable a body fluid (e.g., blood) to flow from the proximal end 118 to the distal end 119 of the graft 112.

Many different types of graft materials may be used for the graft 112. The biocompatible material of the graft 112 may be substantially non-toxic in the in vivo environment of its intended use, and may be substantially unrejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE (ePTFE), and polyurethanes. In addition, materials that are not inherently biocompatible may be subjected to surface modifications to render the materials biocompatible. Examples of surface modifications include, for example, graft polymerization of biocompatible polymers on the surface, coating of the surface with a crosslinked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible.

In addition to the polyesters, fluorinated polymers, and polyurethanes described above, fibers suitable for making textile grafts include, for example, polyethylene, polypropylene, polyaramids, polyacrylonitrile, nylon, and cellulose. Bioremodelable materials also may be used singly or in combination with the aforementioned polymer materials.

The textile may be made of one or more polymers that do not require treatment or modification to be biocompatible. The graft 112 may be constructed from woven multifilament polyester such as, for example and without limitation, Dacron™, commercially available from E. I. DuPont de Nemours and Co., Wilmington, Delaware. Dacron™ is known to be sufficiently biologically inert, non-biodegradable, and durable to permit safe insertion inside the human body. The graft 112 also may be made from natural or organic materials, for example and without limitation, a biological scaffold or bioremodelable material, such as small intestine submucosa ("SIS"), commercially available from Cook Medical Inc., Bloomington, Indiana. The graft 112 may be formed from a single layer or multiple layers of material. In embodiments employing a plurality of layers of material, the layers may remain separate, or may be attached to one another through a secondary process such as sintering, curing, adhesives, sutures, or the like.

The prosthesis 110 may include at least one stent 114 coupled to the graft 112. In the embodiment of FIGS. 1-2, a plurality of internal stents 114a are coupled to an inner surface 121 of the graft 112 along a proximal region of the graft, while a plurality of external stents 114b are coupled to an outer surface 122 of the graft along a distal region of the graft. While one exemplary arrangement is shown in FIGS. 1-2, it will be appreciated that each of the stents 114 may be coupled to inner and/or outer surfaces of the graft 112. An internal stent 114a may be configured as a sealing stent and may be placed at or near the proximal end 118 of the graft 112 to seal the graft at the proximal end to the wall of a body vessel (e.g., a blood vessel) into which the prosthesis 110 may be placed. Additionally, or alternatively, depending on the location where the prosthesis 110 is placed or a particular need, a sealing stent may be placed at either or both the proximal end 118 and/or the distal end 119 of the graft 112.

Stents may add rigidity, expansion force, and/or support to the prosthesis. A stent may be used to obtain and maintain the patency of a body passageway while maintaining the integrity of the passageway. The stents 114 may be made from numerous metals and alloys. For example, the stents 114 may be made from a metallic material selected from stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, such as nitinol, or other suitable materials known in the art. In one example, the stents 114 may include a shape-memory material such as nitinol. Moreover, the structure of the stents 114 may be formed in a variety of ways to provide a suitable intraluminal support structure. For example, one or more stents may be made from a woven wire structure, a laser-cut cannula, individual interconnected rings, or another pattern or design.

In one example, shown in FIGS. 1-2, the stents 114 may be configured in the form of one or more "Z-stents" or Gianturco stents, each of which may include a series of substantially straight segments interconnected by a series of bent segments. The bent segments may include acute bends or apices. The Gianturco stents are arranged in a zigzag configuration in which the straight segments are set at angles relative to one another and are connected by the bent segments. However, as noted above, the stents 114 may be configured in any suitable configuration, and one or more stents may be provided.

The prosthesis 110 may include a plurality of openings. Each opening may be configured as a branch, a fenestration, or any other type of opening formed in the graft 112. The lumen 120 of the graft 112 may be in communication with a point external of the graft through the opening. In one embodiment, the prosthesis 110 may include four openings including two branches and two fenestrations as shown in FIGS. 1-2. For example, the prosthesis 110 may include a first branch 130 having a proximal region 132, a distal region 134, and a lumen 135 extending therebetween. The first branch 130 may extend radially outward from the graft 112, as shown in FIGS. 1-2. The proximal region 132 of the first branch 130 may be configured as a proximal end opening, which may be in fluid communication with a fenestration in the graft 112. In this manner, the lumen 135 of the first branch 130 may be in fluid communication with the lumen 120 of the graft 112 through the fenestration. The lumen of any other branch described herein may be in fluid communication with the lumen of the graft through a fenestration in a similar manner. The prosthesis 110 may include a second branch 140 having a proximal region 142, a distal region 144, and a lumen 145 extending therebetween. The second branch 140 may extend radially outward from the graft 112, as shown in FIGS. 1-2.

The prosthesis 110 may include one or more fenestrations 150. The fenestrations 150 may be configured as pivot fenestrations, which may be pivotable in any direction away from an axis perpendicular to a longitudinal axis of the graft 112. Exemplary pivot fenestrations may include those described in U.S. patent application Ser. No. 13/213,349, filed Aug. 19, 2011 or U.S. Provisional Patent Application No. 61/375,815, filed Aug. 21, 2010, which are incorporated by reference herein in their entirety. For example, the prosthesis 110 may include a first fenestration 160 and a second fenestration 170, which may be configured as pivot fenestrations as shown in FIGS. 1-2. The first and second fenestrations 160, 170 may have features that are identical to one another. Accordingly, unless otherwise specified, the discussion herein related to the first fenestration 160 may be applicable to the second fenestration 170, and vice versa.

FIG. 3 is a close-up view of one example of a pivot fenestration 150. The pivot fenestration 150 may include a fenestration 151 with a diameter. The pivot fenestration 150 may include a first, inner perimeter 152 surrounding the fenestration 151 and having a diameter, a band 154 of flexible material attached to and surrounding the first perimeter 152, and a second, outer perimeter 156 attached to and surrounding the band 154. The band 154 may have a first diameter that is substantially the same as the diameter of the first perimeter 152 and a second diameter that is substantially the same as the diameter of the second perimeter 156. The pivot fenestration 150 may extend from a sidewall of the graft 112 such that the diameter of the band 154 may decrease in a direction away from the surface of the graft 112 from the second perimeter 156 to the first perimeter 152. The band 154 may include a flexible frame 158.

In one embodiment, as shown in FIGS. 1-2, the prosthesis 110 may include a first fenestration 160 and a second fenestration 170, each configured generally as described above with reference to the pivot fenestration 150. For example, the first fenestration 160 may include a fenestration 161, a first, inner perimeter 162, a band 164 of flexible material, and a second, outer perimeter 166. The band 164 may include a flexible frame 168. The second fenestration 170 may include a fenestration 171, a first, inner perimeter 172, a band 174 of flexible material, and a second, outer perimeter 176. The band 174 may include a flexible frame 178.

In one embodiment, the graft 112 may include a tapered portion 124 as shown in FIGS. 1-2. The outer diameter of the tubular body may decrease along the tapered portion 124 in a proximal to distal longitudinal direction such that an outer diameter at the proximal end 118 is greater than an outer diameter at the distal end 119 of the graft 112. The proximal regions 132 and 142 of the first and second branches 130, 140, may be disposed proximate, or within, the tapered portion 124. The fenestrations 160, 170 may be disposed distal to the tapered portion 124. The tapered portion 124 may enable the distal regions 134 of the first branch 130 and/or the distal region 144 of the second branch 140 to extend radially outward relative to the graft 112 without substantially increasing the overall outer diameter of the prosthesis 10 relative to the outer diameter at the proximal end 118 of the graft.

The proximal regions 132, 142 of the first and second branches 130, 140, respectively, may be disposed around a circumference of the graft 112 at a predetermined distance relative to one another. For example, the proximal regions 132, 142 of the first and second branches 130, 140, respectively, may be disposed between about 0 and about 310 degrees apart relative to one another, and more preferably, about 30 degrees apart. Additionally, or alternatively, the proximal regions 132, 142 of the first and second branches 130, 140, respectively, may be disposed at a predetermined distance from one another along a longitudinal axis L of the graft 112. The proximal region 132 may be proximal to the proximal region 142 as shown in FIGS. 1-2. Alternatively, the proximal region 132 may be distal to the proximal region 142 or the proximal regions 132 and 142 may be disposed in close proximity to one another along the longitudinal axis L.

The first and second branches 130, 140 may extend generally longitudinally in a distal direction along the graft 112 of the prosthesis 110 as shown in FIGS. 1-2. Alternatively, the first and second branches 130, 140 may include desired helical shapes to facilitate insertion of various components (e.g., side branch prostheses) into the branches as described herein. Additionally, the helical shapes may reduce torsion imposed by blood flow at the juncture between the graft 112 and the branch vessels. Various exemplary helical branches that extend from a main body of a prosthesis, which may be used in conjunction with the present embodiments, are provided in U.S. Pat. No. 7,407,509 to Greenberg et al., which is hereby incorporated by reference in its entirety.

The first and second fenestrations 160, 170, respectively, may be disposed around a circumference of the graft 112 at a predetermined distance relative to one another. For example, the first and second fenestrations 160, 170 may be disposed between about 50 and about 310 degrees apart relative to one another, and more preferably, about 150 degrees apart. Additionally, or alternatively, the first and second fenestrations 160, 170, respectively, may be disposed in close proximity to one another along the longitudinal axis L of the graft 112 as shown in FIGS. 1-2. Alternatively, the first and second fenestrations 160 and 170 may be disposed at a predetermined distance from one another along the longitudinal axis L. For example, the first fenestration 160 may be proximal to the second fenestration 170, or vice versa.

Referring to FIG. 3, the pivot fenestration 150 may include an inner perimeter 152 surrounding the fenestration 151, a band 154 surrounding the inner perimeter 152, and an outer perimeter 156 surrounding the band. The diameter of the outer perimeter 156 may be greater than the diameter of the band 154 and the diameter of the inner perimeter 152. In one example, the inner perimeter 152, the band 154, and the outer perimeter 156 would be substantially concentric with one another if they were in the same plane, for example, the surface plane of the graft 112. The outer perimeter 156 may lie in the same plane as the graft 112. In other words, the outer perimeter 156 may be substantially flush, even, or aligned with the tubular body of the graft 112. The inner perimeter 152, the band 154, and the outer perimeter 156 may form a hemispherical shape, resembling a dome, or a frustoconical cone extending from the surface of the graft 112. The fenestration 151 may be provided at the peak or top of the hemispherical shape or extension. The outer perimeter 156 may be affixed to the graft 112 by any attachment method including, for example, suturing circumferentially about an aperture disposed through the graft. Although both the inner perimeter 152 and the outer perimeter 156 are shown in FIG. 3 as being substantially circular, the perimeters may be oval, oblong, or any other desired geometric shape.

The pivot fenestration 150 may be located within the lumen 120 of the graft 112 or may extend externally of the graft. In the first aspect, the pivot fenestration 50 may be said to be concave, relative to the outer surface 122 of the graft 112. In the second aspect, the pivot fenestration 150 may be said to be convex, relative to the outer surface 122 of the graft 112. FIG. 3 shows the pivot fenestration 150 located internal to the graft 112. In other words, the pivot fenestration 150 lies within the lumen 120 of the graft 112. As such, the pivot fenestration 150 shown in FIG. 3 may be said to be concave, relative to the outer surface 122 of the graft 112.

The band 154 may be made of the same or a different biocompatible material as the graft 112. For example, the biocompatible material of the band 154 may have a greater pliability than the biocompatible material of the graft 112. The band 154 may be sufficiently flexible to enable the fenestration 151 to move relative to the graft 112. In other words, the band 154 may be sufficiently flexible to enable the inner perimeter 152 surrounding the fenestration 151 to move relative to the graft 112. Such movement may enable a prosthesis (e.g., a side branch prosthesis) disposed in the fenestration 151 to be positioned in various orientations with respect to the longitudinal axis L of the graft 12. For example, a prosthesis may be oriented upwardly, downwardly, laterally, diagonally, and the like with respect to the graft 112. In some aspects, the band 154 may have up to about 180 degrees of freedom of movement relative to the surface plane of the graft 112. Accordingly, the pivot fenestration 150 may enable the prosthesis 110 to be used with a variety of patients, due to its ability to adapt to the variance in the positioning of the diseased branch vessels. For example, if a branch vessel is or becomes offset longitudinally or transversely from the pivot fenestration 150, the pivot fenestration may pivot the side branch prosthesis in the necessary direction and to the necessary degree to maintain the side branch prosthesis in place in the branch vessel. In one embodiment, the fenestrations 160, 170 of the prosthesis 110 may be configured as pivot fenestrations as shown in FIGS. 1-2. This configuration may allow for variability in the positions of a patient's left renal artery 878 and right renal artery 877 when the prosthesis 110 is used to treat a thoracoabdominal aneurysm as described below.

Figure 5:
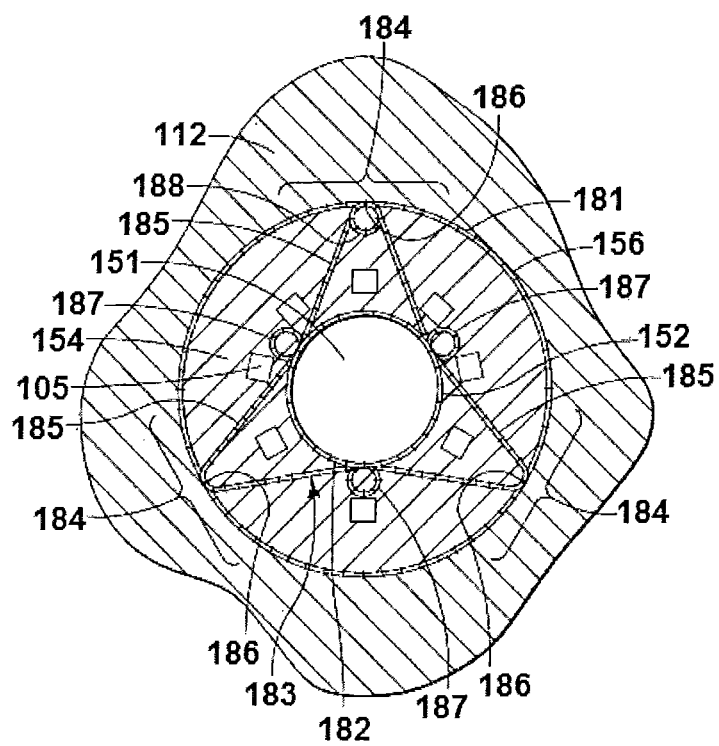
FIG. 5 is an interior view of one embodiment of a pivot fenestration.

In one embodiment, the pivot fenestration 150 may include a reinforcement frame as shown in FIGS. 3 and 5. The reinforcement frame may be sutured or otherwise attached to the graft 112. For example, a reinforcement frame 181 may be positioned about the outer perimeter 156.

Additionally, or alternatively, a reinforcement frame 182 may be positioned about the inner perimeter 152. The reinforcement frames 181, 182 may be rings. In one preferred aspect, the reinforcement frames 181, 182 may be wires that are sutured about the respective perimeters to reinforce the pivot fenestration 150. The reinforcement frames 181, 182 may be made of any suitable material. One preferred material is a superelastic or shape memory material such as nitinol. In another preferred embodiment, the reinforcement frames 181, 182 may be made of radiopaque or other imagable material. In another embodiment, the reinforcement frames 181, 182 may be solid rings. Alternatively, the reinforcement frames 181, 182 may be wires looped about themselves into rings with unattached ends such that the rings may be expanded or contracted in diameter. Suitable frames are disclosed in U.S. Patent Application Publication No. 2005/0102021 by Osborne, which is hereby incorporated by reference in its entirety.

Figure 4:
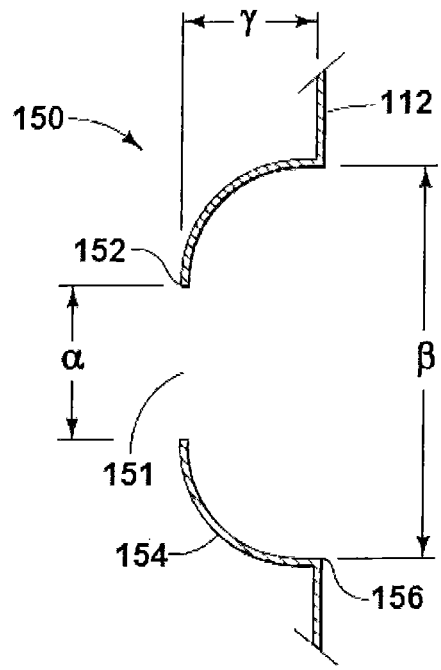
FIG. 4 is a partial, cross sectional view of a portion of one embodiment of a prosthesis having a pivot fenestration.

FIG. 4 shows a partial, cross-sectional view of a portion of the prosthesis 110, having a pivot fenestration 150. The band 154 may be tapered such that the diameter decreases throughout its depth $\gamma$. The depth $\gamma$ may be determined based on the amount of movement desired for the pivot fenestration 150 during use and the ability to cannulate the targeted branch vessel. As the depth $\gamma$ decreases, the amount of second biocompatible material used for the band 154 also may decrease, which may limit the range of motion of the pivot fenestration 150. Furthermore, the depth $\gamma$ may be large enough to enable cannulation of the targeted branch vessel. The depth $\gamma$ may range from about 3 to about 10 mm, and preferably is about 6 mm. The inner perimeter 152 may have a diameter $\alpha$ that is smaller than the diameter $\beta$ of the outer perimeter 156. The diameter $\alpha$ of the inner perimeter 152 may be determined based on the average size of the targeted branch vessel. In one aspect, the prosthesis 110 may be used to repair a diseased renal artery. Accordingly, the diameter $\alpha$ of the inner perimeter 152 may be based on the average diameter of the openings to the renal arteries, or about 6 mm.

The diameter $\beta$ of the outer perimeter 156 may be determined based on the desired amount of movement and the desired patency of the prosthesis 110. As the diameter $\beta$ of the outer perimeter 156 changes, the range of motion provided by the pivot fenestration 150 also changes. For example, as the diameter $\beta$ of the outer perimeter 156 decreases, the range of motion also decreases. Additionally, the diameter $\beta$ of the outer perimeter 156 may be sized to prevent interference with circumferentially adjacent struts of a stent 114, that may be aligned with the pivot fenestration 150 along the longitudinal axis L of the graft 112. Hence, in one example, the diameter $\beta$ of the outer perimeter 156 may be at most about 15 mm to accommodate the stent 114. The diameters $\alpha$ and $\beta$ combined with the depth $\gamma$ may provide the band 154 with sufficient surface area for the pivot fenestration 150 to pivot during deployment of a secondary prosthesis into the fenestration 151 after deployment of the prosthesis 110 within the patient's body. The pivot fenestration 150 also may pivot after deployment of the secondary prosthesis therein based on dynamic changes to the patient's anatomy (i.e., movement).

Figure 6:
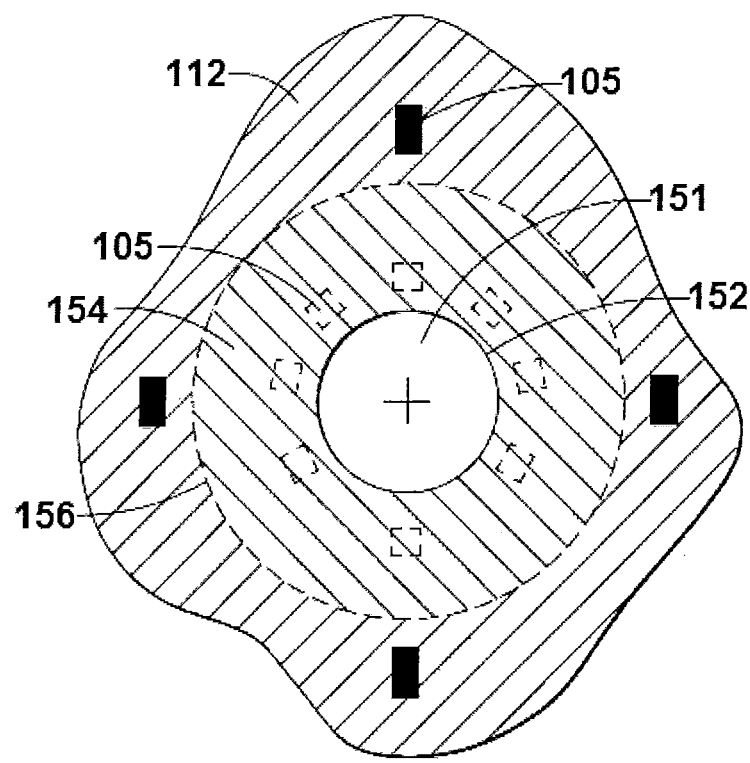
FIG. 6 is an exterior view of the pivot fenestration of FIG. 5.

FIGS. 5-6 show an internal view and an external view, respectively, of a pivot fenestration 150 in an aspect in which the pivot fenestration is disposed within the lumen 120 of the graft 112. FIG. 5 shows the fenestration 151, the inner perimeter 152, the band 154, and the outer perimeter 156. The reinforcement frame 181 may be positioned about the outer perimeter 156, and the reinforcement frame 182 may be positioned about the inner perimeter 152. The reinforcement frames 181, 182 may be affixed to the outer perimeter 156 and the inner perimeter 152, respectively as described above. Markers 105 may be placed around the inner perimeter 152 to facilitate proper placement and alignment of a side branch prosthesis and the fenestration 151.

As shown in FIG. 5, the band 154 may be provided with a flexible frame 183. The flexible frame 183 may provide structural support to the band 154 to prevent the pivot fenestration 150 from everting or inverting (depending on the initial configuration) once the prosthesis 110 is deployed with the diseased vessel. The flexible frame 183 may be positioned on the band 154 either on the interior or exterior surface of the band. In one example, the flexible frame 183 may be positioned on the interior surface of the band 154 as shown in FIGS. 5-6. The flexible frame 183 may include a continuous wire formed into a plurality of support units 184. Each support unit 184 may have a generally undulating shape including straight struts 185 interconnected by outwardly facing apices or bends 186. The number of support units 184 may range from about 2 support units to about 10 support units. In a preferred embodiment, the flexible frame 183 has three support units 184.

In one example, the outwardly facing apices 186 of the flexible frame 183 may abut or connect to the reinforcing frame 181 of the outer perimeter 156 of the pivot fenestration 150 as shown in FIGS. 5-6. The outwardly facing apices 186 may be, for example, sewn or sutured to the reinforcing frame 181. The flexible frame 183 may be bent to form a plurality of loops 187. The loops 187 may be positioned in the troughs formed between adjacent support units 184. Each loop 187 may abut and/or connect to the reinforcing frame 182 of the inner perimeter 152 of the pivot fenestration 150. The loops 187 may be, for example, sewn or sutured to the reinforcing frame 182. A loop 188 may be positioned within an apex 186 of a support unit 184. Other configurations for the flexible frame 183 including, but not limited to, spirals also may be suitable. The flexible frame 183 may be heat set into the desired configuration prior to attachment to the band 154. The flexible frame 183 may be made of an elastic or superelastic material such as, for example and without limitation, nitinol.

Figure 7:
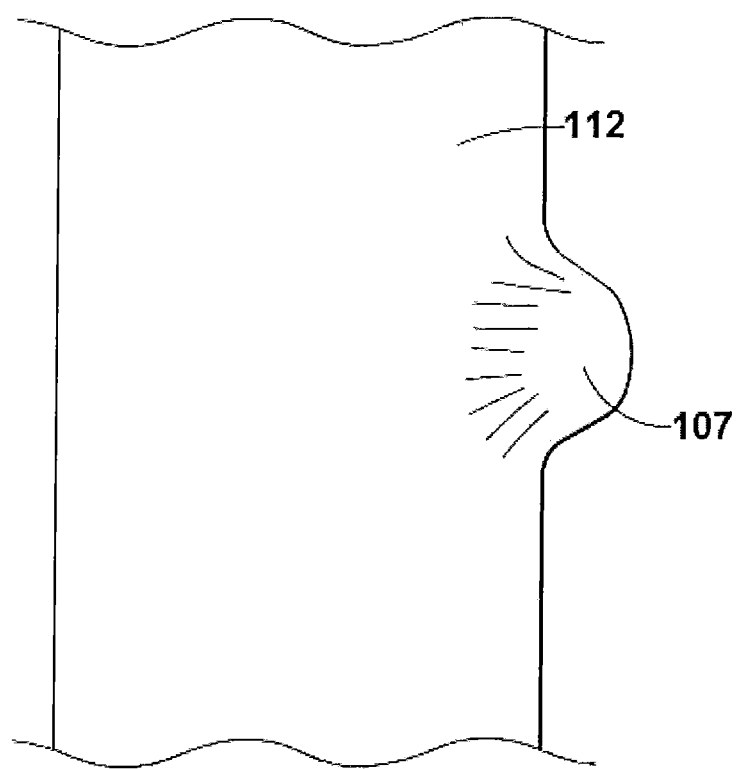
FIG. 7 depicts a prosthesis having a protrusion of graft material to form one embodiment of a pivot fenestration.

The band 154 of the pivot fenestration 150 may be formed from a protrusion 190 having a bubble like configuration as shown in FIG. 7. The protrusion may be formed using processes such as those described in U.S. Patent Application Publication No. 2010/0063576 by Schaeffer et al. which is hereby incorporated by reference in its entirety. The protrusion 190 may be integrally formed with the body of the graft 112 and may include a second biocompatible graft material. The protrusion 190 may be created during the weaving process used to create the graft material of the graft 112. The graft material may be woven in weaves including, but not limited to, plain weaves, basket weaves, rep or rib weaves, twill weaves (e.g., straight twill, reverse twill, herringbone twill), satin weaves, and double weaves (e.g., double-width, tubular double weave, reversed double weave). Desirably, the weave may include a tubular double layer weave. The fabric may be woven on a table loom, a floor loom, a jacquard loom, a counterbalance loom, a jack loom, or an upright loom. Desirably, the fabric may be woven on a floor loom. The fabric may have any configuration possible, but preferably has warp and weft yarns. In one aspect, both the warp yarns and the weft yarns are textile yarns.

To create the protrusion 190, the number of warp yarns used while weaving the graft material of the graft 112 may be increased in the region where the protrusion 190 is desired. While the additional warp yarns are woven into the graft 112, the number of weft yarns may be kept constant. By increasing the number of warp yarns while holding the number of weft yarns constant, the second biocompatible graft material expands outwardly in the radial direction. The number of warp yarns may be increased until a pre-determined diameter has been reached. Once the desired depth for the protrusion 190 is reached, the number of warp yarns introduced into the weaving apparatus may be decreased until the number of warp yarns is equal to the number of weft yarns used to form the remainder of the graft 112. A fenestration may be created through the protrusion 190 by any suitable means. For example, the fenestration may be created by applying heat to the center of the protrusion 190. Reinforcing frames may be added about the fenestration and adjacent to and surrounding the protrusion 190 to form the inner and outer perimeters 152 and 156, respectively, of the pivot fenestration 150. Further, a flexible frame 183 may be attached to the protrusion 190 to maintain the protrusion in a desired extended configuration.

The prosthesis 110 may have a compressed, reduced diameter delivery state in which the prosthesis may be advanced to a target location within a vessel, duct, or other anatomical site, such as the thoracoabdominal aorta as described below with reference to FIGS. 14A-15G. The prosthesis 110 may have an expanded state, as shown in FIGS. 1-2, in which the prosthesis may be configured to apply a radially outward force upon the vessel, duct, or other target location. In the expanded state, fluid flow may be allowed through the lumen 120 of the graft 112.

The prosthesis 110 may include one or more radiopaque markers 105 to provide radiographic visualization of the position of the endoluminal prosthesis 110 when placed in the vessel or duct of a patient. A plurality of radiopaque markers 105, which according to one example may be provided in the form of gold beads, may be coupled to the graft 112, the stents 114, the branches 130, 140, and/or the fenestrations 160, 170 to facilitate imaging of various desired locations along the length of the endoluminal prosthesis 110. The radiopaque markers 105 may be positioned at the proximal end 118 and/or the distal end 119 of the graft 112. The radiopaque markers also may be positioned proximate the first branch 130 and/or the second branch 140 and/or proximate to the first fenestration 160 and/or the second fenestration 170 to facilitate imaging of those portions of the prosthesis 110.

FIGS. 8-9 depict another embodiment of a prosthesis 210, which may be configured as a stent graft. The prosthesis 210 may include a graft 212 including a generally tubular body of a biocompatible material. The graft 212 may have a proximal end 218, a distal end 219, and a lumen 220 extending therebetween. The graft 212 may include a fenestration 250 disposed in the graft 212 at a location between the proximal end 218 and the distal end 219. The fenestration 250 may be configured as a self-sealing fenestration as further described below.

The graft 212 may include four openings each configured as a branch as shown in FIGS. 8-9. For example, the graft 212 may include a first branch 230 having a proximal region 232, a distal region 234, and a lumen 235 extending therebetween. The first branch 230 may extend radially outward from the graft 212 as shown in FIGS. 8-9. The proximal region 232 of the first branch 230 may be disposed at a location proximal to the fenestration 250 as best shown in FIG. 9.

The graft 212 may include a second branch 240 having a proximal region 242, a distal region 244, and a lumen 245 extending therebetween. The second branch 240 may extend radially outward from the graft 212 as shown in FIGS. 8-9. The proximal region 242 of the second branch 240 may be disposed at a location proximal to the fenestration 250 as best shown in FIG. 9.

The graft 212 may include a third branch 260 having a proximal region 262, a distal region 264, and a lumen 265 extending therebetween. The third branch 260 may extend radially outward from the graft 212 as shown in FIGS. 8-9. The proximal region 262 of the third branch 260 may be disposed at a location distal to the fenestration 250 as best shown in FIG. 9.

The graft 212 may include a fourth branch 270 having a proximal region 272, a distal region 274, and a lumen 275 extending therebetween. The fourth branch 270 may extend radially outward from the graft 212 as shown in FIGS. 8-9. The proximal region 272 of the fourth branch 270 may be disposed at a location distal to the fenestration 250 as shown in FIGS. 8-9.

In one embodiment, the distal region 234 of the first branch 230, the distal region 244 of the second branch 240, and the distal region 264 of the third branch 260 each may extend in a distal direction with respect to the graft 212 toward the distal end 219 of the graft 212 as shown in FIG. 8. The distal region 274 of the fourth branch 270 may extend in a proximal direction with respect to the graft 212 toward the proximal end 218 of the graft 212. Such orientations of the distal regions of the four branches 230, 240, 260, and 270 may facilitate insertion of four corresponding side branch prostheses. For example, in the exemplary method of FIGS. 18A-18L shown and described below, side branch prostheses 830, 840 and 820 may be delivered in a proximal to distal direction with respect to the graft 212 for the branches 230, 240, and 260, respectively, while another side branch prosthesis 850 may be delivered in a distal to proximal direction with respect to the graft 212 for the branch 270.

In one embodiment, the graft 212 may have a tapered portion 224 as shown in FIGS. 8-9. The tapered portion 224 may be configured generally as described above with reference to the tapered portion 124 of the prosthesis 110. The proximal regions 232, 242 of the first and second branches 230, 240, respectively, may be disposed proximal to, or within, the tapered portion 224. The fenestration 250 and the proximal regions 262, 272 of the third and fourth branches 260, 270, respectively, may be disposed distal to the tapered portion 224. Alternatively, the fenestration 250 may be disposed within the tapered portion 224, or at any suitable location distal to the distal region 234 of the first branch 230 for purposes described below. The tapered portion 234 may enable the distal regions of one or more of the branches 230, 240, 260, and/or 270 to extend radially outward relative to the graft 212 without substantially increasing the overall outer diameter of the prosthesis 210 relative to an outer diameter at the proximal end 218 of the graft 212.

The proximal regions 232, 242 of the first and second branches 230, 240, respectively, may be disposed around a circumference of the graft 212 at a predetermined distance relative to one another. For example, the proximal regions 232, 242 of the first and second branches 230, 240, respectively, may be disposed between about 50 and about 310 degrees apart relative to one another, and more preferably, about 180 degrees apart. Additionally, or alternatively, the proximal regions 232, 242 of the first and second branches 230, 240, respectively, may be disposed in close proximity to one another along a longitudinal axis L of the graft 212, as shown in FIG. 8. Alternatively, the proximal region 232 of the first branch 230 may be disposed proximal to the proximal region 242 of the second branch 240, or vice versa.

The proximal regions 262, 272 of the third and fourth branches 260, 270, respectively, may be disposed around a circumference of the graft 212 at a predetermined distance relative to one another. For example, the proximal regions 262, 272 of the third and fourth branches 260, 270, respectively, may be disposed between about 50 and about 310 degrees apart relative to one another, and more preferably, about 180 degrees apart. Additionally, or alternatively, the proximal region 262 of the third branch 260 may be disposed proximal to the proximal region 272 of the fourth branch 270, as shown in FIG. 8, or vice versa. Alternatively, the proximal regions 262, 272 of the third and fourth branches 260, 270, respectively, may be disposed in close proximity to one another along a longitudinal axis L of the graft 212.

Any of the four branches 230, 240, 260, and 270 may include desired helical shapes to facilitate insertion of various components described herein. Additionally, the helical shapes may reduce torsion imposed by blood flow at the juncture between the graft 212 and the branch vessels. The helical shapes depicted herein are for illustrative purposes only and are not intended to be limiting. Various exemplary helical branches that extend from a main graft, which may be used in conjunction with the present embodiments, are provided in U.S. Pat. No. 7,407,509 to Greenberg et al., which is hereby incorporated by reference in its entirety.

The prosthesis 210 may include at least one stent coupled to the graft 212. For example, a plurality of stents 214a may be coupled to an inner surface of the graft 212 along a proximal region of the graft 212, while a plurality of stents 214b may be coupled to an outer surface of the graft 212 along a distal region of the graft 212 as shown in FIGS. 8-9. While one exemplary arrangement is shown in FIGS. 8-9, it will be appreciated that any of the stents 214 may be coupled to inner and/or outer surfaces of the graft 212. The stents 214 may be configured generally as described above with reference to the stents 114 of the prosthesis 110.

The graft 212 may have a compressed, reduced diameter delivery state in which the graft may be advanced to a target location within a vessel, duct or other anatomical site, such as the thoracoabdominal aorta as shown below in FIGS. 14A-14F and 18A-18L. The graft 212 may have an expanded state, as shown in FIGS. 8-9, in which the graft may be configured to apply a radially outward force upon the vessel, duct or other target location. In the expanded state, fluid flow may be allowed through the lumen 220 of the graft 212.

The prosthesis 210 may include one or more radiopaque markers 205 to provide radiographic visualization of the position of the endoluminal prosthesis 210 when placed in the vessel or duct of a patient. A plurality of radiopaque markers 205, which according to one example may be provided in the form of gold beads, may be coupled to the graft 212 and/or the stents 214 to facilitate imaging of various desired locations along the length of the prosthesis 210.

In any of the embodiments described herein, at least one fenestration may be configured as a self-sealing fenestration. For example, the fenestration 250 of the prosthesis 210 may be configured as a self-sealing fenestration to allow various delivery components (e.g., a guide wire, a catheter, a sheath, or an introducer) to be passed through the graft 212 as further described below without leakage through the graft upon removal of the wire. In other examples, any of the fenestrations described herein may be configured as self-sealing fenestrations. The self-sealing fenestration may include a resilient flap of material that may cover the fenestration via a spring force upon removal of the wire. One suitable exemplary self-sealing fenestration is described and shown in U.S. Patent Application Publication No. 2007/0250154 by Greenberg et al., which is hereby incorporated by reference in its entirety.

Figure 10A:
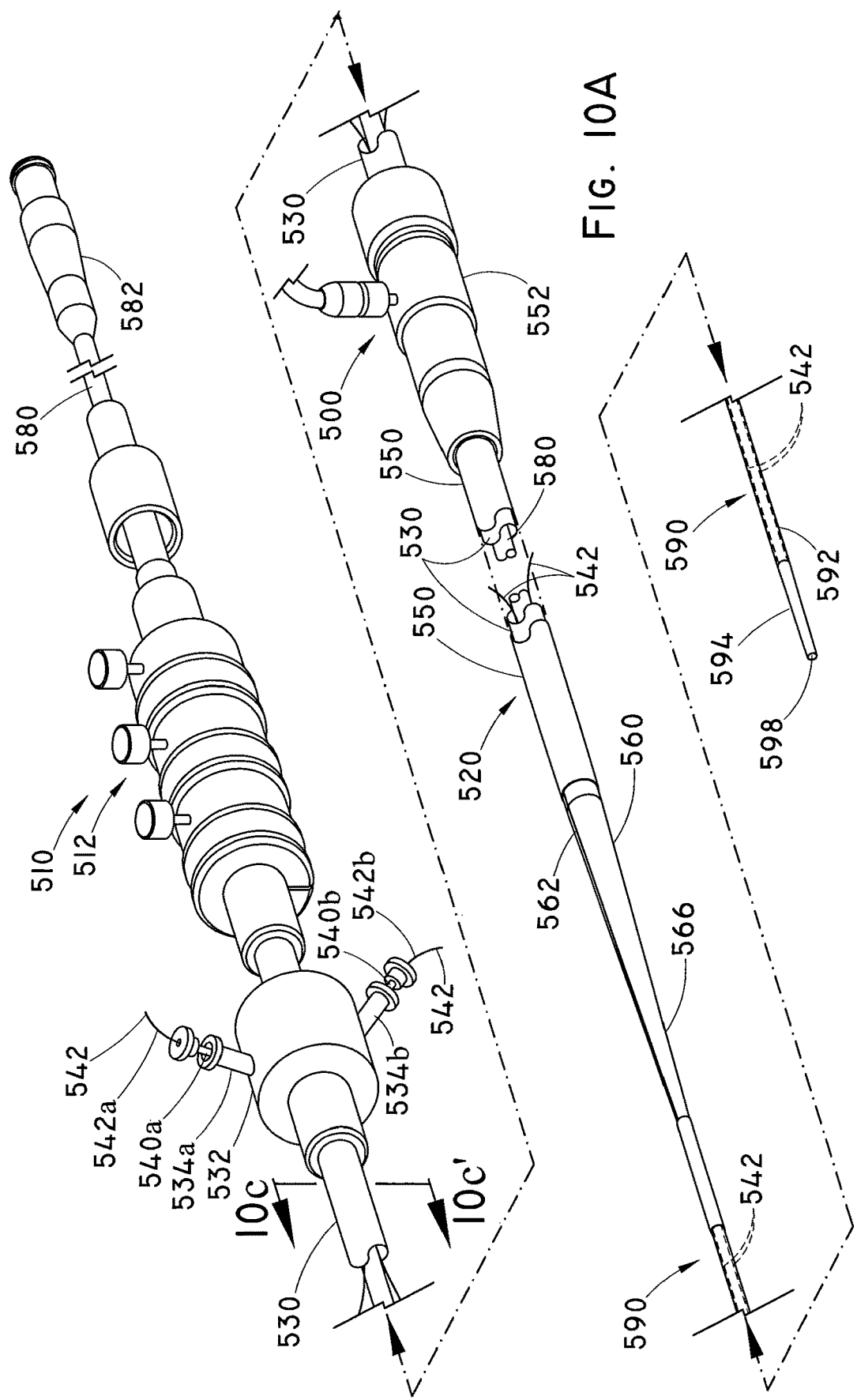
FIG. 10A is a perspective view of one embodiment of a delivery device.
Figure 10B:
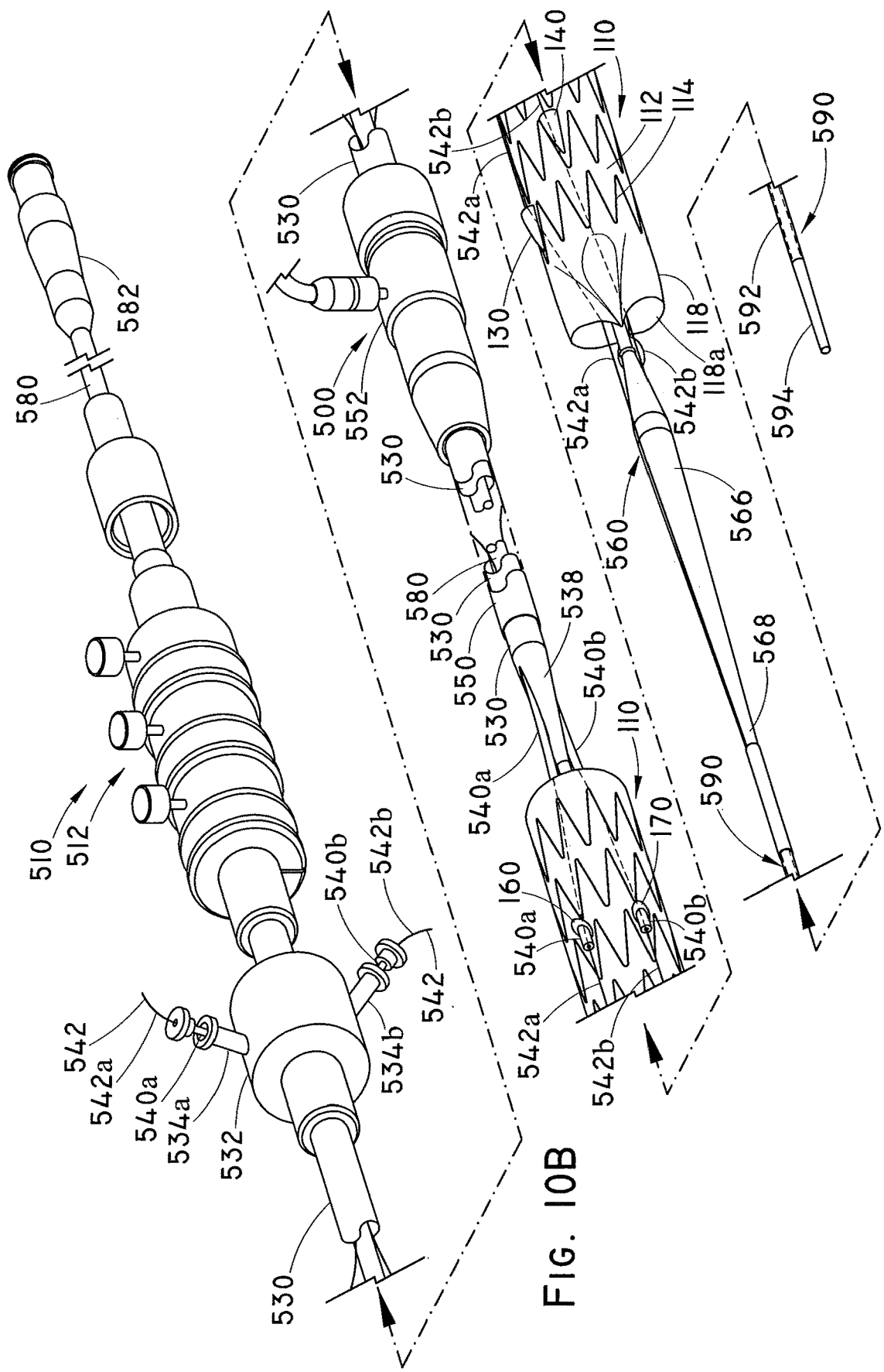
FIG. 10B is a perspective view of the delivery device of FIG. 10A with a sheath retracted to expose an endoluminal prosthesis retained on the delivery device.

An endoluminal prosthesis (e.g., the prosthesis 110, shown in FIGS. 1-2, or the prosthesis 210, shown in FIGS. 8-9) may be delivered into a patient's thoracoabdominal aorta using a suitable delivery device or introducer. FIG. 10A shows one example of a delivery device 500 in a condition for introduction of an endoluminal prosthesis into a patient, and FIG. 10B shows the delivery device of FIG. 10A with the sheath withdrawn to show the prosthesis. It is unlikely that the particular configuration shown in FIG. 10B would actually occur in use because, by the time that the sheath has been withdrawn to expose the prosthesis, the length extending module should have been withdrawn as is discussed below. Although FIG. 10B shows the delivery device 500 with the prosthesis 110 loaded thereon, the delivery device 500 may be used to deliver the prosthesis 210 in a similar manner. In other examples, the delivery device 500 may be used to deliver a prosthesis having any other suitable configuration.

The delivery device 500 may include a handle portion 510 and an introduction portion 520. The handle portion 510 is intended to remain outside of the patient in use, and the introduction portion 520 is intended to be introduced into the patient via a puncture in an artery such as the femoral artery. A catheter, such as the pusher catheter 530, may extend proximally from a trigger wire release region 512 of the handle 510. A pusher catheter hub 532 may be positioned near the distal end of the pusher catheter 530 and configured to receive one or more auxiliary sheaths 540 and/or auxiliary guide wires 542 as further described below. A sheath 550 and a sheath hub 552 may extend over at least a portion of the pusher catheter 530. The sheath 550 may extend proximally to a nose cone dilator 560. The sheath 550 may be retracted relative to the pusher catheter 530 to expose a prosthesis retained below the sheath as further described below. A guide wire cannula 580 may extend from a connector 582 (e.g., a Luer lock hub) positioned at the distal end of the delivery device 500, through the handle 510 and the pusher catheter 530 to extend to the nose cone dilator 560. The guide wire cannula 580 may be received within a main lumen of the pusher catheter 530. The guide wire cannula 580 may extend at least partially through the nose cone dilator 560. The guide wire cannula 580 may be tracked over a guide wire in a conventional manner to guide the delivery device through the vasculature of the patient. The connector 582 may be used to introduce liquids such as contrast media to enable tracking of the progress of an operation.

The nose cone dilator 560 may be positioned at the proximal end of the guide wire cannula 580 and may include one or more longitudinal grooves 562 on an outside longitudinal surface of the nose cone dilator. The grooves 562 are shown in greater detail in FIGS. 11A-11D. One or more auxiliary guide wires 542 may be received within the grooves 562 as further described below. The length of the nose cone dilator may be reduced relative to conventional delivery devices. Such a reduced length may reduce the length of the auxiliary guide wire 542 that is exposed on the outside longitudinal surface of the nose cone dilator 560 during delivery of a prosthesis. A length extending module (LEM) 590 may be releasably mounted to the proximal end of the nose cone dilator 560. The LEM 590 may be configured to carry an auxiliary guide wire beyond the site of placement of a prosthesis to establish through-and-through access during deployment of the prosthesis as further described below. The LEM 590 may include an outer sheath 592 surrounding a dilator 594 as shown in FIGS. 10A-10B and 11. In one example, the outer sheath 592 may have a size of about 8 Fr. The dilator 594 of the LEM 590 may include one or more longitudinal grooves 596. The longitudinal grooves 596 may extend generally longitudinally along the dilator 594 as further described below. One or more auxiliary guide wires 542 may be received within the longitudinal grooves 596 also as further described below. The LEM 590 also may include a guide wire lumen 598, which may be in fluid communication with the guide wire cannula 580 to enable the delivery device 500 to be tracked over a guide wire in a conventional manner. The releasable mounting between the LEM 590 and the nose cone dilator 560 may be achieved by any of the examples described below in reference to FIGS. 12A-13B. In other examples, the releasable mounting may be achieved by any other suitable means without departing from the scope of this disclosure. For example, the LEM 590 may be releasably attached to the nose cone dilator 560 as described in World Intellectual Property Organization Publication No. 2011/116308, which is incorporated by reference herein in its entirety.

The pusher catheter hub 532 may include one or more side ports 534. In one example, the pusher catheter hub 532 may be configured as a tri-port hub. To that end, the pusher catheter hub 532 may include a central port, a first side port 534a, and a second side port 534b as shown in FIGS. 10A-10B. The guide wire cannula 580 may be received within the central port of the pusher catheter hub 532. Each side port 534 may extend outward from the pusher catheter hub 532. Each side port 534 also may extend distally relative to the pusher catheter hub 532 as shown in FIGS. 10A-10B. An auxiliary guide wire 542 and/or an auxiliary sheath 540 may be received within each side port 534 as further described below. The side ports 534 may be positioned circumferentially apart around the pusher catheter hub 532. In one example, the first side port 534a may be positioned on a top side of the pusher catheter hub 532, and the second side port 534b may be positioned on a bottom side of the pusher catheter hub generally opposite the first side port with respect to the circumference of the pusher catheter hub. This configuration is illustrative, and the side ports 534 may be positioned at any circumferential positions on the pusher catheter hub 532.

Each side port 534 of the pusher catheter hub 532 may be in fluid communication with an auxiliary lumen of the pusher catheter 530. To that end, the pusher catheter 530 may have one or more auxiliary lumens 536 extending generally longitudinally within the pusher catheter. FIG. 10C shows a transverse cross-sectional view of the delivery device 500 taken along line 10C-10C' of FIG. 10A. In this example, the pusher catheter 530 may include a first auxiliary lumen 536a and a second auxiliary lumen 536b. The auxiliary lumens 536 may be positioned in the annular region of the pusher catheter 530 between the guide wire cannula 580 and the exterior surface of the pusher catheter. In one example, the first auxiliary lumen 536a and the second auxiliary lumen 536b may be positioned adjacent one another and near the top of the pusher catheter 530 as shown in FIG. 10C. In other examples, the auxiliary lumens 536 may be positioned generally opposite one another with respect to the circumference of the pusher catheter 530, or in any other orientation relative to one another. In one example, the auxiliary lumens 536 may have a size of about 6 Fr.

Each auxiliary lumen 536 may extend from the pusher catheter hub 532 to the proximal end of the pusher catheter 530. FIG. 10D shows the proximal end of the pusher catheter 530. The proximal end of the pusher catheter 530 may include a tapered transition 538. The diameter of the tapered transition 538 may taper from the diameter of the pusher catheter 530 to the diameter of the guide wire cannula 580. Each auxiliary lumen 536 may extend through the tapered transition 538 to provide a continuous pathway between the corresponding side port 534 and the proximal end of the pusher catheter 530. In other examples, the proximal end of the pusher catheter 530 may be blunt as opposed to tapered. In these examples, each auxiliary lumen 536 may extend through the blunt proximal end to provide a continuous pathway between the corresponding side port 534 and the proximal end of the pusher catheter 530.

An auxiliary sheath 540 may be received within each of the side ports 534 and each of the auxiliary lumens 536 as shown in FIGS. 10A-10D. For example, a first auxiliary sheath 540a may extend through the first side port 534a and into the first auxiliary lumen 536a. The first auxiliary sheath 540a may extend proximally within the first auxiliary lumen 536a and exit the proximal end of the pusher catheter 530. A second auxiliary sheath 540b may extend through the second side port 534b and into the second auxiliary lumen 536b. The second auxiliary sheath 540b may extend proximally within the second auxiliary lumen 536b and exit the proximal end of the pusher catheter 530. The auxiliary sheaths 540 may further extend proximally into the prosthesis loaded on the delivery device as described below.

One or more auxiliary guide wires 542 may be received within the side ports 534 and the auxiliary lumens 536. The one or more auxiliary guide wires 542 also may be received within the auxiliary sheaths 540. For example, an auxiliary guide wire 542 may extend within the first auxiliary sheath 540a and through the first side port 534a. The auxiliary guide wire 542 may extend proximally within the first auxiliary lumen 536a and exit the proximal end of the pusher catheter 530. The auxiliary guide wire 542 may extend further proximally into the prosthesis and along the LEM 590 as described below. The auxiliary guide wire 542 may extend distally from the LEM 590 and into the second auxiliary sheath 540b. The auxiliary guide wire 542 may extend within the second auxiliary sheath 542b and into the second auxiliary lumen 536b. The auxiliary guide wire 542 may extend distally within the second auxiliary lumen 536b and through the side port 534b to exit the pusher catheter 530.

FIG. 10B depicts the prosthesis 110 releasably retained on the delivery device 500. The prosthesis 110, or another prosthesis, may be positioned on the delivery device 500 distal of the nose cone dilator 560. The prosthesis 110 may be retained in a compressed condition within the sheath 550. Upon retraction of the sheath 550, the prosthesis 110 may expand to a partially expanded configuration as shown in FIG. 10B. In the partially expanded configuration, the proximal end 118 of the prosthesis 110 may be retained by one or more releasable trigger wires (not shown) to form one or more lobes of graft material 118a at the proximal end of the prosthesis. Access through the open lobes of graft material 118a may be achieved to track an access catheter over one or more auxiliary guide wires as described below.

In one example, one or more auxiliary sheaths 540 may be received within the prosthesis 110. The auxiliary sheaths may be preloaded in the prosthesis 110 prior to delivery of the prosthesis within the vasculature of the patient. For example, the first auxiliary sheath 540a may exit the proximal end of the pusher catheter 530 as described above and enter the distal end 119 of the prosthesis 110 as shown in FIGS. 1-2 and 10B. The first auxiliary sheath 540a may extend proximally within the lumen 120 of the prosthesis 110 and through the first fenestration 160. The proximal end of the first auxiliary sheath 540a may be positioned external of the prosthesis 110 near the first fenestration 160. In other words, the proximal end of the first auxiliary sheath 540a may be positioned generally adjacent the outer surface 122 of the graft 112 of the prosthesis 110 near the first fenestration 160. In one example, the first auxiliary sheath 540a may extend about 5 cm beyond the first fenestration 160 of the prosthesis 110.

Similarly, the second auxiliary sheath 540b may exit the proximal end of the pusher catheter 530 as described above and enter the distal end 119 of the prosthesis 110. The second auxiliary sheath 540b may extend proximally within the lumen 120 of the prosthesis 110 and through the second fenestration 170. The proximal end of the second auxiliary sheath 540b may be positioned external of the prosthesis 110 near the second fenestration 170. In other words, the proximal end of the second auxiliary sheath 540b may be positioned generally adjacent the outer surface 122 of the graft 112 of the prosthesis 110 near the second fenestration 170. In one example, the second auxiliary sheath 540b may extend about 5 cm beyond the second fenestration 170 of the prosthesis 110. The first and second auxiliary sheaths 540a, 540b may aid in cannulating the respective first and second fenestrations 160, 170 with branch prostheses upon deployment of the prosthesis 110 as further described below. Preloading the auxiliary sheaths within the prosthesis 110 prior to deployment of the prosthesis may reduce the amount of time required to deploy the prosthesis by obviating the need to cannulate each of the fenestrations with a sheath after the prosthesis has been introduced within the body of the patient. Preloading the auxiliary sheaths also may reduce the amount of catheter manipulation required during a deployment procedure.

In one example, the auxiliary guide wire 542 may be received within the prosthesis 110, or another prosthesis, and the delivery device 500 in a preloaded configuration as further described below. The auxiliary guide wire 542 may be preloaded in the prosthesis 110 prior to delivery of the prosthesis within the vasculature of the patient. A first portion 542a of the auxiliary guide wire 542 (i.e., a first wire segment), which may be received within the first auxiliary sheath 540a preloaded in the prosthesis 110, may pass through an end opening at the distal end 119 of the prosthesis and extend proximally within the lumen 120 of the prosthesis as shown in FIGS. 1-2 and 10B. The first portion 542a of the auxiliary guide wire 542 may pass through the first fenestration 160 to exit the prosthesis 110 and extend proximally external to the prosthesis. The first portion 542a of the auxiliary guide wire 542 may exit the proximal end of the first auxiliary sheath 540a and extend further proximally external to the prosthesis 110. The first portion 542a of the auxiliary guide wire 542 may pass through an end opening at the distal region 134 of the first branch 130 and extend proximally within the lumen 135 of the first branch. The first portion 542a of the auxiliary guide wire 542 may pass through an end opening at the proximal region 132 of the first branch 130 and extend proximally within the lumen 120 of the prosthesis 110 to exit an end opening at the proximal end 118 of the prosthesis. The first portion 542a of the auxiliary guide wire 542 may extend further proximally to engage the LEM 590 as further described below.

A second portion 542b of the auxiliary guide wire 542 (i.e., a second wire segment) may pass through the end opening at the proximal end 118 of the prosthesis 110 and extend distally within the lumen 120 of the prosthesis 110. The second portion 542b of the auxiliary guide wire 542 may pass through an end opening at the proximal region 142 of the second branch 140 and extend distally within the lumen 145 of the second branch. The second portion 542b of the auxiliary guide wire 542 may pass through an end opening at the distal region 144 of the second branch 140 to exit the prosthesis 110 and extend distally external to the prosthesis. The second portion 542a of the auxiliary guide wire 542 may enter the proximal end of the second auxiliary sheath 540b and extend distally external to the prosthesis within the second auxiliary sheath. The second portion 542b of the auxiliary guide wire 542 may pass through the second fenestration 170 and extend distally within the lumen 120 of the prosthesis 110 to exit the end opening at the distal end 119 of the prosthesis. In this manner, the single auxiliary guide wire 542 may pass through each of the first and second branches 130, 140 and the first and second fenestrations 160, 170. The auxiliary guide wire 542 may not penetrate the graft 112 (i.e., the sidewall of the main tubular graft body) at any location other than the branches and/or the fenestrations. This may reduce the potential for leakage through the graft 112 after removal of the auxiliary guide wire 542 as described below. The auxiliary guide wire 542 may aid in cannulating each of the first and second branches 130, 140 and the first and second fenestrations 160, 170 with branch prostheses upon deployment of the prosthesis 110 as further described below. In other examples, the auxiliary guide wire 542 may include two or more auxiliary guide wires. For example, the first portion 542a and the second portion 542b of the auxiliary guide wire may be configured as separate auxiliary guide wires. In other words, the first portion 542a of the auxiliary guide wire 542 may be configured as a first wire segment, and the second portion 542b of the auxiliary guide wire may be configured as a second wire segment. The first and second wire segments may be joined to one another or separate from one another (i.e., unattached).

In another example, the auxiliary guide wire 542 may be received within the prosthesis 210 and the delivery device 500 in a preloaded configuration as further described below. The auxiliary guide wire 542 may be preloaded in the prosthesis 210 prior to delivery of the prosthesis within the vasculature of the patient as shown in FIGS. 8-9. The first portion 542a of the auxiliary guide wire 542 (i.e., the first wire segment) may extend along an outer surface of the distal end 219 of the graft 212. The first portion 542a of the auxiliary guide wire 542 may pass through an end opening at the distal region 264 of the third branch 260 and extend proximally within the lumen 265 of the third branch. The first portion 542a of the auxiliary guide wire 542 may pass through an end opening at the proximal region 262 of the third branch 260 and extend proximally within the lumen 220 of the prosthesis 210 a relatively short distance. The first portion 542a of the auxiliary guide wire 542 may pass through the fenestration 250 to exit the prosthesis 210 and extend proximally external to the prosthesis. The first portion 542a of the auxiliary guide wire 542 may pass through an end opening at the distal region 234 of the first branch 230 and extend proximally within the lumen 235 of the first branch. The first portion 542a of the auxiliary guide wire 542 may pass through an end opening at the proximal region 232 of the first branch 230 and extend proximally within the lumen 220 of the prosthesis 210 to exit an end opening at the proximal end 218 of the prosthesis. The first portion 542a of the auxiliary guide wire 542 may extend further proximally to engage the LEM 590 as further described below.

The second portion 542b of the auxiliary guide wire 542 (i.e., the second wire segment) may pass through the end opening at the proximal end 218 of the prosthesis 210 and extend distally within the lumen 220 of the prosthesis 210. The second portion 542b of the auxiliary guide wire 542 may pass through an end opening at the proximal region 242 of the second branch 240 and extend distally within the lumen 245 of the second branch. The second portion 542b of the auxiliary guide wire 542 may pass through an end opening at the distal region 244 of the second branch 240 to exit the prosthesis 210 and extend distally external to the prosthesis. The second portion 542a of the auxiliary guide wire 542 may pass through an end opening at the distal region 274 of the fourth branch 270 and extend proximally within the lumen 275 of the fourth branch (i.e., distally relative to the graft 212). The second portion 542b of the auxiliary guide wire 542 may pass through an end opening at the proximal region 272 of the fourth branch 279 and extend distally within the lumen 220 of the prosthesis 210 to exit the end opening at the distal end 119 of the prosthesis. In this manner, the single auxiliary guide wire 542 may pass through each of the first, second, third, and fourth branches 230, 240, 260, 270. The auxiliary guide wire 542 may not penetrate the graft 212 (i.e., the sidewall of the main tubular graft body) at any location other than the branches and/or the fenestrations. This may reduce the potential for leakage through the graft 212 after removal of the auxiliary guide wire 542 as described below. The auxiliary guide wire 542 may aid in cannulating each of the first, second, third, and fourth branches 230, 240, 260, 270 with branch prostheses upon deployment of the prosthesis 210 as further described below. In other examples, the auxiliary guide wire 542 may include two or more auxiliary guide wires as described above.

FIG. 11 shows a proximal portion of the delivery device 500. FIG. 11A is a cross-sectional view of the nose cone dilator 560 taken along line 11A-11A' of FIG. 11. The nose cone dilator 560 may be surrounded by the sheath 550. One or more longitudinal grooves 562 may extend generally longitudinally along an outer surface of the nose cone dilator 560. In one example, two longitudinal grooves 562 may be diametrically opposite one another with respect to the outer surface of the nose cone dilator 560 as shown in FIG. 11A. In other examples, any number of longitudinal grooves may be positioned in any arrangement on the nose cone dilator 560. The auxiliary guide wire 542 may be received within the longitudinal grooves 562 as further described below. FIG. 11B is a cross-sectional view of the tapered tip 566 of the nose cone dilator 560 taken along line 11B-11B' of FIG. 11. The longitudinal grooves 562 may extend generally longitudinally along the outer surface of the tapered tip 566 of the nose cone dilator 560 as described above in reference to the longitudinal grooves extending along the nose cone dilator generally. The longitudinal grooves 562 may be configured as generally U-shaped grooves formed in the surface of the nose cone dilator 560 as shown in FIG. 11C. Alternatively, the longitudinal grooves 562 may be configured as a substantially closed tube except for a narrow, elongated opening 563 as shown in FIG. 11D.

In one example, the tapered tip 566 of the nose cone dilator 560 may include substantially closed longitudinal grooves 562 as shown in FIG. 11D. With the auxiliary guide wire 542 retained in the substantially closed groove, as further described below, the probability of the auxiliary guide wire coming out of the groove unintentionally during deployment of the prosthesis may be reduced. This may reduce the probability of the auxiliary guide wire 542 becoming entangled with other portions of the delivery device 500. The nose cone dilator 560 may be formed from a polyurethane material which exhibits a degree of elasticity or flexibility so that the nose cone dilator may be deflected to enlarge the opening 563 of the longitudinal groove 562 to enable removal of the auxiliary guide wire 542 from the longitudinal groove. During delivery of the prosthesis, as further described below, a sheath and/or a dilator may be advanced over the auxiliary guide wire 543 from the proximal end and/or the distal end of the delivery device 500. The dilator may draw the auxiliary guide wire 542 out of the substantially closed longitudinal groove 562.

FIG. 11E is a cross-sectional view of the LEM 590 taken along line 11E-11E' of FIG. 11. The dilator 594 of the LEM 590 may be surrounded by the sheath 592 of the LEM. One or more longitudinal grooves 596 may extend generally longitudinally along an outer surface of the dilator 594 of the LEM 590. The longitudinal grooves 596 of the LEM 590 may generally align with the longitudinal grooves 562 of the nose cone dilator 560. To that end, in one example, two longitudinal grooves 596 may be diametrically opposite one another with respect to the outer surface of the LEM 590 as shown in FIG. 11E. In other examples, any number of longitudinal grooves may be positioned in any arrangement on the LEM 590. The longitudinal grooves 596 of the LEM 590 may be configured substantially as described above with reference to the longitudinal grooves 562 of the nose cone dilator 560.

Figure 11F:
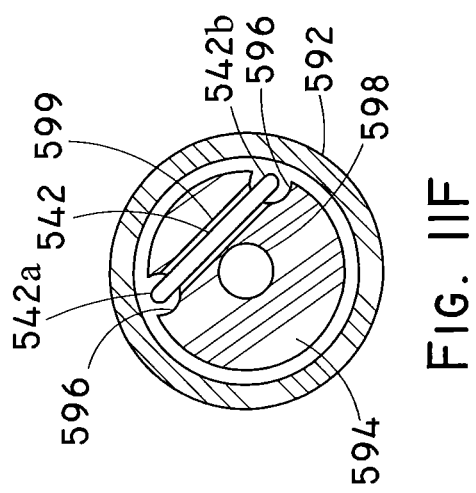
FIG. 11F is a transverse cross-sectional view of the delivery device taken along line 11F-11F' of FIG. 11.

FIG. 11F shows a transverse cross-sectional view taken along line 11F-11F' of FIG. 11. Near the proximal end 595 of the dilator 594 of the LEM 590, a cross aperture 599 may extend through the dilator between two longitudinal grooves 596. The cross aperture 599 may provide a pathway connecting the two longitudinal grooves 596 through the dilator 594. In other words, the cross aperture 599 may extend through the dilator in a transverse direction with respect to the longitudinal axis of the dilator to connect the two longitudinal grooves 596. This may enable the auxiliary guide wire 542 to cross over from one longitudinal groove 596 to another longitudinal groove at the cross aperture 599. By crossing over from one longitudinal groove 596 to another longitudinal groove, the auxiliary guide wire 542 may be capable of extending proximally along the length of the LEM 590 within one longitudinal groove, crossing over to another longitudinal groove at the cross aperture 599, and extending distally along the length of the LEM within the other longitudinal groove.

In one example, the auxiliary guide wire 542 may extend proximally along the delivery device 500 from a point near the distal end of the delivery device to a point near the proximal end of the delivery device and then distally back to the point near the proximal end of the delivery device. For example, the first portion 542a of the auxiliary guide wire 542 may extend through the first side port 534a of the pusher catheter hub 532 and proximally within the pusher catheter 530 and the first auxiliary sheath 540a as described above. The first portion 542a of the auxiliary guide wire 542 may exit the pusher catheter 530 and engage the prosthesis (e.g., the prosthesis 110 or the prosthesis 210) as described above. For example, the first portion 542a of the auxiliary guide wire 542 may extend further proximally within the lumen 120 of the prosthesis 110 and the first auxiliary sheath 540a. The first portion 542a of the auxiliary guide wire 542 may exit the prosthesis 110 through the first fenestration 160, exit the first auxiliary sheath 540a, and reenter the prosthesis 110 through the first branch 130. The first portion 542a of the auxiliary guide wire 542 may extend further proximally to exit the proximal end 118 of the prosthesis 110 and extend further proximally within one of the longitudinal grooves 562 of the nose cone dilator 560. The first portion 542a of the auxiliary guide wire 542 may extend proximally within a corresponding one of the longitudinal grooves 596 of the LEM 590 to the cross aperture 599. At the cross aperture 599, the auxiliary guide wire 542 may cross over from one longitudinal groove 596 to another longitudinal groove 596.

The second portion 542b of the auxiliary guide wire 542 may extend distally from the cross aperture 599 within the longitudinal groove 596 of the LEM 590 and then the longitudinal groove 562 of the nose cone dilator 560. The second portion 542b of the auxiliary guide wire 542 may engage the prosthesis (e.g., the prosthesis 110 or the prosthesis 210) as described above. For example, the second portion 542b of the auxiliary guide wire 542 may enter the lumen 120 of the prosthesis 110, extend further distally within the prosthesis, exit the prosthesis through the second branch 140, and extend distally external of the prosthesis. The second portion 542b of the auxiliary guide wire 542 may enter the second auxiliary sheath 540b, reenter the prosthesis 110 through the second fenestration 170, and extend further distally out through the distal end 119 of the prosthesis. The second portion 542b of the auxiliary guide wire 542 may enter the pusher catheter 530 and extend further distally within the pusher catheter 530 and the second auxiliary sheath 540b, and exit the pusher catheter through the side port 534b of the pusher catheter hub 532. In this manner, the single auxiliary guide wire 542 may extend from the pusher catheter hub 532 to a point near the proximal end of the LEM 590 and back to the pusher catheter hub. In other examples, two separate auxiliary guide wires may be substituted for the first and second portions, respectively, of the auxiliary guide wire 542.

Using a single auxiliary guide wire 542 may aid in retaining the LEM 590 in engagement with the nose cone dilator 560 as described below. Using a single auxiliary guide wire 542 also may eliminate the presence of guide wire ends near the proximal end of the delivery device. This may enhance the safety of the delivery device by eliminating potentially sharp guide wire ends that may otherwise be present near the proximal tip of the device. The auxiliary guide wire 542 also may pass through each of the first and second branches 130, 140 and the first and second fenestrations 160, 170 of the prosthesis 110 to aid in cannulating each of the first and second branches and the first and second fenestrations with branch prostheses upon deployment of the prosthesis 110 as further described below.

FIG. 11G shows a portion of the proximal end of another embodiment of the LEM 590. In this embodiment, the same reference numerals are used for features corresponding to those shown in FIGS. 11-11E. FIG. 11H shows a transverse cross-sectional view taken along line 11H-11H' of FIG. 11G. In this embodiment, the LEM 590 may include one or more longitudinal apertures 596a, as opposed to the longitudinal grooves 596 described above. For example, two longitudinal apertures 596a may extend generally longitudinally within the dilator 594 of the LEM 590 from the distal end of the dilator to a point near the proximal end of the dilator. The auxiliary guide wire 542 may be received within the longitudinal apertures 596a generally as described above with reference to the longitudinal grooves 596.

Figure 11I:
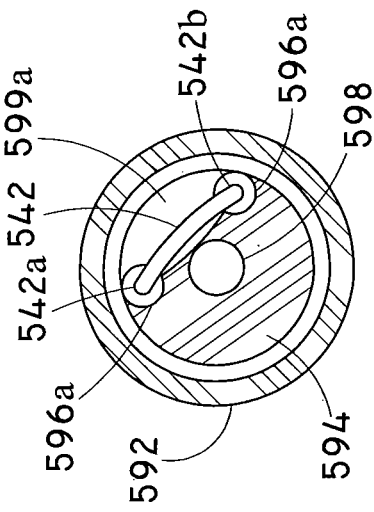
FIG. 11I is a transverse cross-sectional view of the delivery device taken along line 11I-11I' of FIG. 11G.

FIG. 11I is a transverse cross-sectional view of a proximal portion of one embodiment of the LEM 590 taken along line 11I-11I' of FIG. 11G. In this embodiment, the LEM 590 may include one or more longitudinal apertures 596a generally as described above in reference to FIGS. 11G-11H. Near the proximal end 595 of the dilator 594 of the LEM 590, a scallop 599a may be cut into the LEM to expose two longitudinal apertures 596a. The scallop 599a may provide a pathway connecting the two longitudinal apertures 596a through the dilator 594. This may enable the auxiliary guide wire 542 to cross over from one longitudinal aperture 596a to another longitudinal aperture at the scallop 599a. By crossing over from one longitudinal aperture 596a to another longitudinal aperture, the auxiliary guide wire 542 may be capable of extending proximally along the length of the LEM 590 within one longitudinal aperture, crossing over to another longitudinal aperture at the scallop 599a, and extending distally along the length of the LEM within the other longitudinal aperture.

Figure 12A:
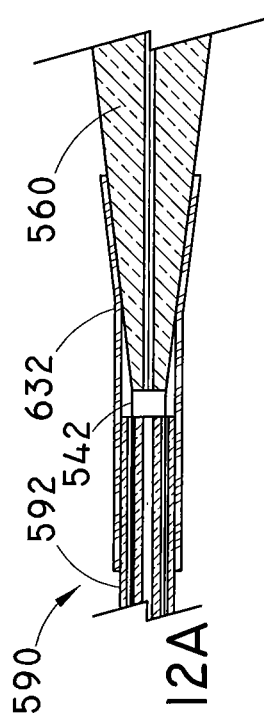
FIG. 12A depicts one embodiment of a connection arrangement between a nose cone dilator and a length extending module of a delivery device.

A friction fit between the tapered tip 566 of the dilator 560 and the LEM 590 may be achieved by a flexible sleeve 632 as shown in FIG. 12A. The flexible sleeve 632 may be affixed to the outer sheath 592 of the LEM 590 and may extend distally from the LEM to engage the proximal end 566 of the nose cone dilator 560. The flexible sleeve 632 and the nose cone dilator 560 may be retained in engagement by friction. When the LEM 590 is to be removed from the nose cone dilator 560 as described below, a pull on the LEM from the proximal end of the LEM may be sufficient to release the LEM from the nose cone dilator.

Figure 12B:
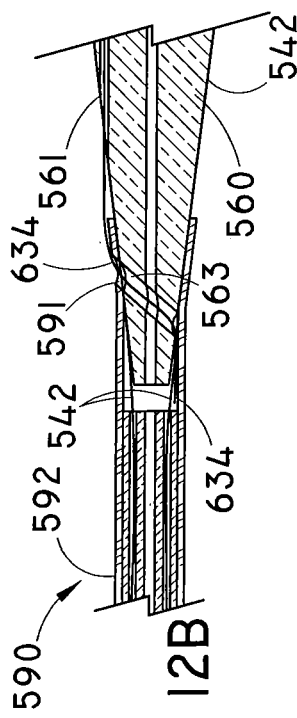
FIG. 12B depicts another embodiment of a connection arrangement between a nose cone dilator and a length extending module of a delivery device.

In an alternative embodiment, the LEM 590 and the nose cone dilator 560 may be retained in engagement by a trigger wire system as shown in FIG. 12B. In this embodiment, the delivery device 500 may include a trigger wire 634 which may extend within the nose cone dilator 560. The trigger wire 634 may exit the nose cone dilator 560 through an elongate aperture 561 in the nose cone dilator. The trigger wire 634 may extend along an outer surface of the outer sheath 592 of the LEM 590, through an aperture 591 in the outer sheath, and back into the nose cone dilator 560 through an aperture 563. In this manner, the trigger wire 634 may engage each of the nose cone dilator 560 and the sheath 592 of the LEM 590 to retain the LEM in place relative to the nose cone dilator. The trigger wire 634 may extend distally to a trigger wire release mechanism 512 on the handle 510 of the delivery device 500. When the trigger wire 634 is withdrawn by activation of the trigger wire release mechanism 512 during a deployment procedure, the outer sheath 592 may be removed from the nose cone dilator 560.

Figure 12C:
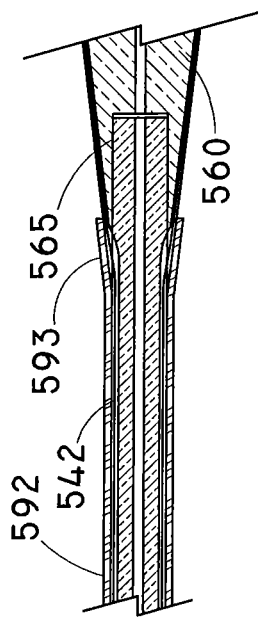
FIG. 12C depicts another embodiment of a connection arrangement between a nose cone dilator and a length extending module of a delivery device.

In yet another alternative embodiment, the LEM 590 and the nose cone dilator 560 may be retained in engagement as shown in FIG. 12C. In this embodiment, the distal end of the dilator 594 of the LEM 590 may be configured to fit within a proximal recess 565 formed in the proximal end of the nose cone dilator 560. The outer sheath 592 of the LEM 590 may include a slightly flared portion 593 near the distal end of the outer sheath. The flared portion 593 of the outer sheath 592 may fit over the proximal end of the nose cone dilator 560.

Thus, in this embodiment, the distal end of the dilator 594 of the LEM 590 may be received by and retained in the proximal recess 565 of the nose cone dilator 560 by the friction fit between the distal end of the dilator 594 of the LEM 590 in the proximal recess 565 and between the distal end of the sheath 592 of the LEM and the nose cone dilator. Additionally, opposite ends of the auxiliary guide wire 542 may be locked at the handle 510, and the auxiliary guide wire may cross over within the LEM 590 as described above. This may prevent the LEM 590 from moving in a proximal direction relative to the nose cone dilator 560.

Figure 12D:
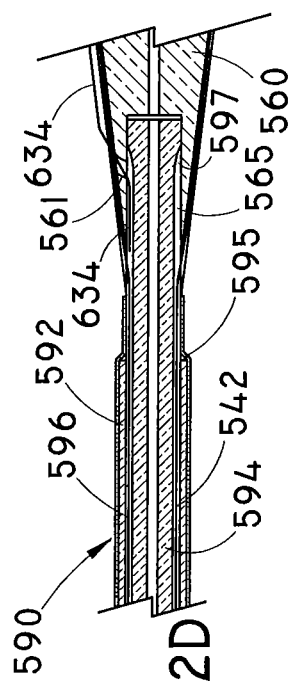
FIG. 12D depicts another embodiment of a connection arrangement between a nose cone dilator and a length extending module of a delivery device.

In still another alternative embodiment, the LEM 590 and the nose cone dilator 560 may be retained in engagement as shown in FIG. 12D. In this embodiment, the distal end of the dilator 594 of the LEM 590 may be configured to fit within the proximal recess 565 formed in the proximal end of the nose cone dilator 560 as described above with reference to FIG. 12C. The longitudinal grooves 596 of the dilator 594 of the LEM 590 may terminate at a point 597 proximal of the distal end of the dilator 594. A sleeve 595 may surround at least a portion of the nose cone dilator 560 and the outer sheath 592 of the LEM 590. The sleeve 595 may be shrink fitted and/or glued to the outer sheath 592 and the nose cone dilator 560. The sleeve 595 may retain the auxiliary guide wire 542 within the longitudinal grooves 596 of the dilator 594. A hole 561 may extend through the nose cone dilator 560 and into the proximal recess 565 as shown in FIG. 12D. A trigger wire 634 may extend from the handle 510 of the delivery device 500, through the hole 561, and into a longitudinal groove 596 just proximal of the end 597 of the groove.

Thus, in this embodiment, the distal end of the dilator 594 of the LEM 590 may be received by and retained in the proximal recess 565 of the nose cone dilator 560 by the friction fit between the distal end of the dilator 594 of the LEM 590 in the proximal recess 565. Additionally, the trigger wire 634 may be positioned against the end 597 of the longitudinal groove 596 to interfere with proximal movement of the LEM 590 relative to the nose cone dilator 560. Additionally, opposite ends of the auxiliary guide wire 542 may be locked at the handle 510, and the auxiliary guide wire may cross over within the LEM 590 as described above. This may prevent the LEM 590 from moving in a proximal direction relative to the nose cone dilator 560.

In another alternative embodiment, the LEM 590 and the nose cone dilator 560 may be retained in engagement as shown in FIGS. 13A-13B. In this embodiment, the distal end of the dilator 594 of the LEM 590 may be configured to fit within the proximal recess 565 formed in the proximal end of the nose cone dilator 560 as described above with reference to FIG. 12C. The longitudinal grooves 596 of the dilator 594 of the LEM 590 may terminate at the point 597 proximal of the distal end of the dilator 594 as described above with reference to FIG. 12D. A sleeve 732 may surround at least a portion of the outer sheath 592 of the LEM 590. The sleeve 732 may be shrink fitted and/or glued to the outer sheath 592 near the distal end of the outer sheath. The sleeve 732 may include an elongate tab 733 which may extend distally along the nose cone dilator 560 when the distal end of the dilator 594 of the LEM 590 is received within the proximal recess 565 in the nose cone dilator. A hole 735 may be formed near the distal end of the elongate tab 733. A corresponding hole 561 may extend through the nose cone dilator 560 and into the proximal recess 565 as shown in FIG. 13B. A trigger wire 734 may extend from the handle 510 of the delivery device 500, through the hole 735 and the corresponding hole 561, and into a longitudinal groove 596 just proximal of the end 597 of the groove.

Thus, in this embodiment, the distal end of the dilator 594 of the LEM 590 may be received by and retained in the proximal recess 565 of the nose cone dilator 560 by the friction fit between the distal end of the dilator 594 of the LEM 590 in the proximal recess 565. Additionally, the trigger wire 734 may be positioned against the end 597 of the longitudinal groove 596 to interfere with proximal movement of the LEM 590 relative to the nose cone dilator 560. Additionally, opposite ends of the auxiliary guide wire 542 may be locked at the handle 510, and the auxiliary guide wire may cross over within the LEM 590 as described above. This may prevent the LEM 590 from moving in a proximal direction relative to the nose cone dilator.

Figure 14A:
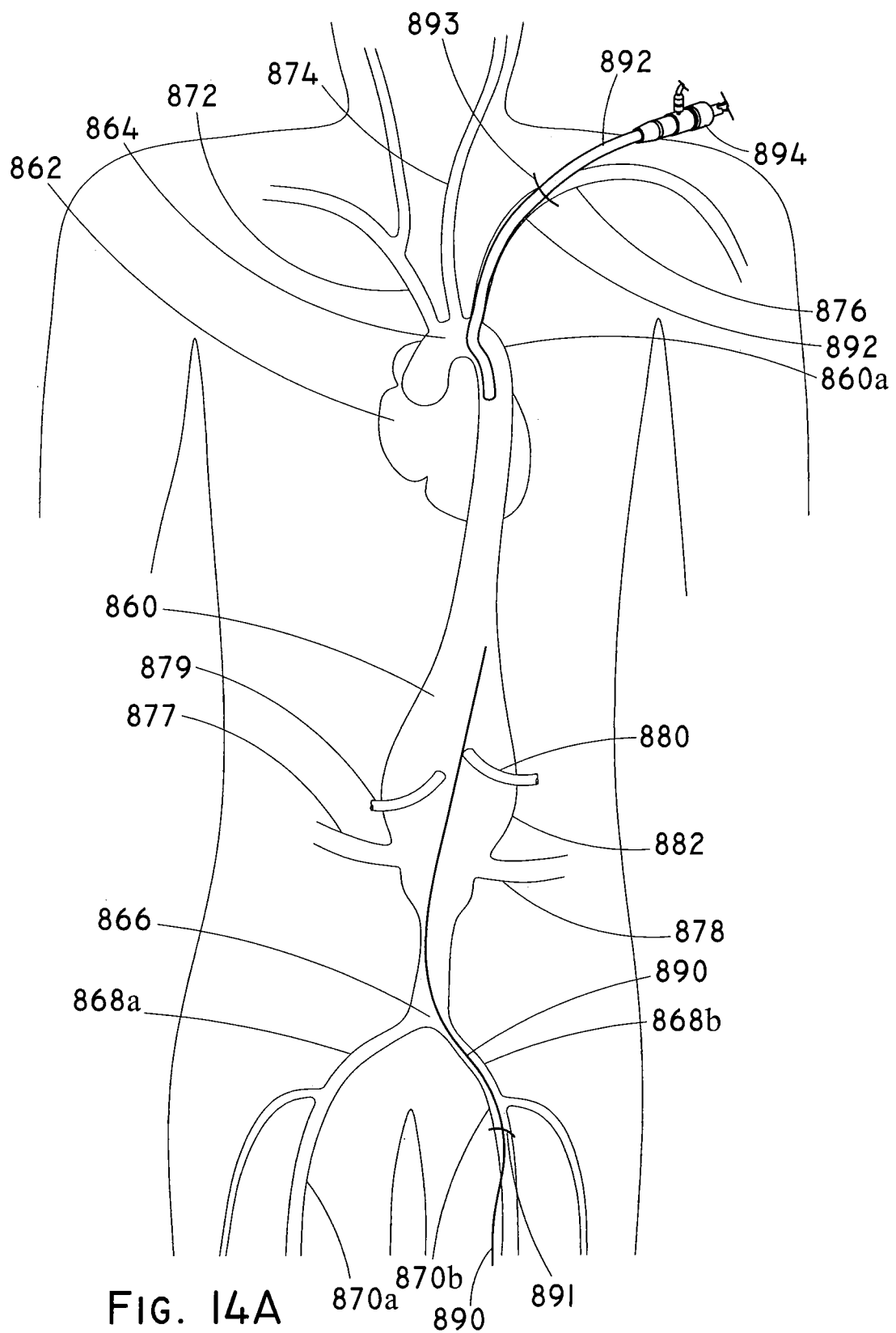
FIG. 14A illustrates an exemplary method step of introducing a guide wire and a brachial access sheath into the vasculature of a patient.

Referring now to FIGS. 14A-18L, exemplary method steps for using a prosthesis (e.g., the prosthesis 110, shown in FIGS. 1-2, or the prosthesis 210, shown in FIGS. 8-9) to treat a condition in the area of a patient's thoracoabdominal aorta and/or branch vessels are shown and described. FIGS. 14A-14F illustrate exemplary method steps for delivering the prosthesis to the patient's thoracoabdominal aorta. In a first step, the prosthesis may be provided with one or more auxiliary guide wires (e.g., the auxiliary guide wire 542) coupled to the graft in the preloaded configuration as described above. FIG. 14A shows a schematic view of a portion of the vasculature of a human body. The vasculature shown includes an aorta 860 extending from a heart 862 over a thoracic arch 864 to an aortic bifurcation 866. At the aortic bifurcation 866, iliac arteries 868a, 868b extend down to respective femoral arteries 870a, 870b. A brachiocephalic artery 872, a carotid artery 874, and a left subclavian artery 876 extend from the thoracic arch 864. Renal arteries 877, 878 extend from the aorta 860, and a superior mesenteric artery 879 and a celiac artery 880 extend from the aorta 860 just proximal of the renal arteries 877, 878. These four arteries can generally be referred to as the visceral arteries. The aorta 860 is depicted with an aneurism 882, which has occurred in the region of the visceral arteries. It may be desirable to deploy a prosthesis, such as a stent graft, into the aorta 860 to span the aneurism 882 while, at the same time, allowing catheterization and side arm deployment into the renal arteries 877, 878, the superior mesenteric artery 879, and the celiac artery 880.

In a first stage of the process, as shown in FIG. 14A, a guide wire 890 may be introduced through a femoral puncture 891 in the femoral artery 870b. The guide wire 890 may be advanced proximally through the femoral artery 870b into the iliac artery 868b and into the aorta 860. The guide wire 890 may be advanced proximally until the proximal end of the guide wire is positioned just proximal of the visceral arteries. A brachial access sheath 892 may be introduced through a brachial puncture 893 in the left subclavian artery 876. The brachial access sheath 892 may include a sheath hub 894. In one example, the brachial access sheath 892 may have a size of about 12 Fr. The brachial access sheath 892 may be advanced through the left subclavian artery 876 and into the descending aorta 860a. In any of the examples described herein, the access sheath 892 may be introduced through the right brachial artery, the left brachial artery, the axillary artery, or any other suitable access point. Such alternative access points are contemplated by and within the scope of this disclosure.

Figure 14B:
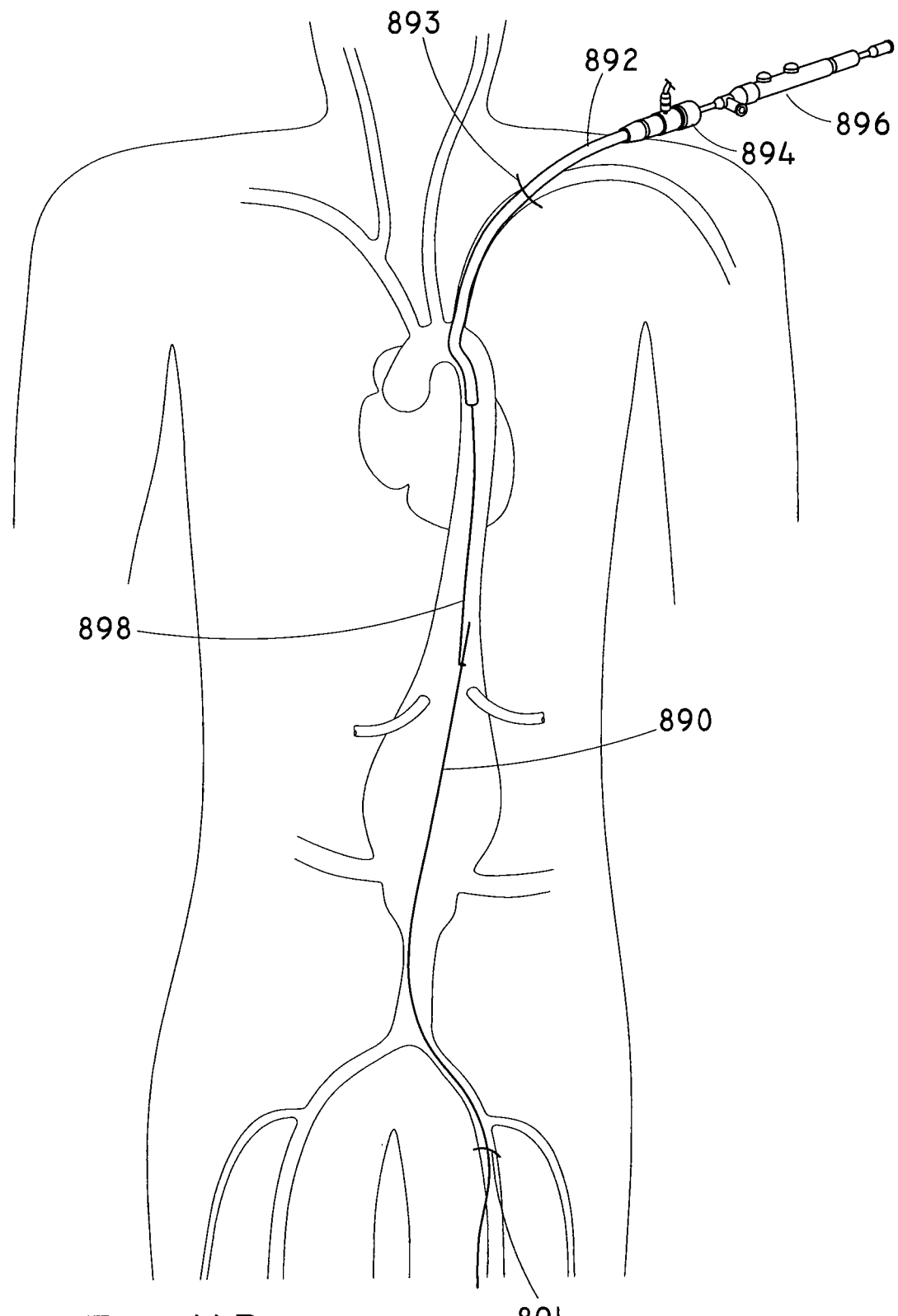
FIG. 14B illustrates an exemplary method step of engaging the guide wire with a grasper device and a snare.
Figure 14C:
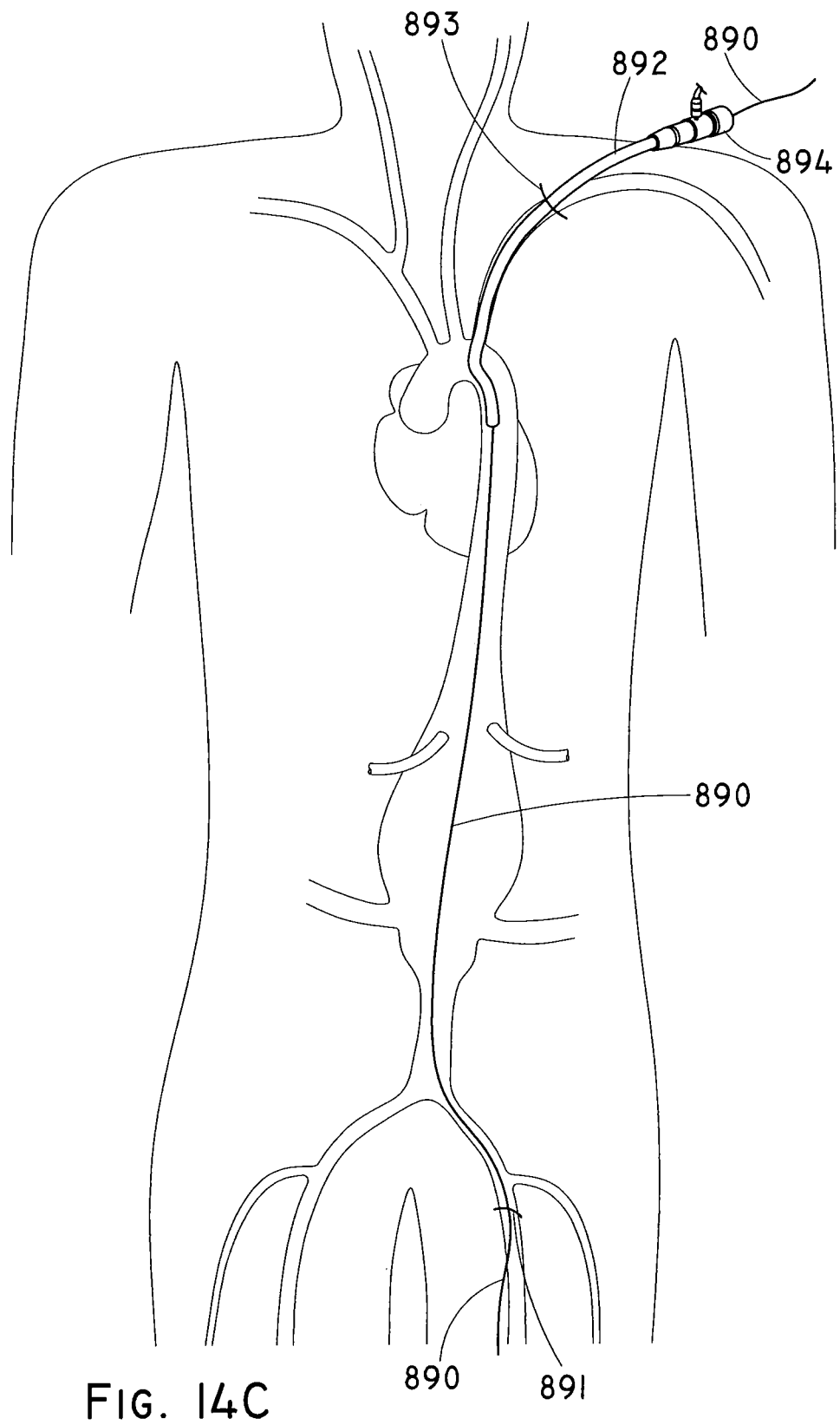
FIG. 14C shows the guide wire extending through the brachial access sheath.

As shown in FIG. 14B, a grasper device 896 with a snare 898 may be introduced through the sheath hub 894 and down the brachial access sheath 892. The snare 898 may engage the proximal end of the guide wire 890. The snare 898 may be used to draw the guide wire 890 through the brachial access sheath 892 as shown in FIG. 14C. The guide wire 890 may be drawn out through the sheath hub 894 of the brachial access sheath 892 to establish a femoral to subclavian through-and-through wire.

In an alternative embodiment, the grasper device 896 with the snare 898 may be introduced through the femoral puncture 891, and the guide wire 890 may be introduced through the brachial puncture 893. The snare 898 may be used to engage the guide wire 890 and draw the guide wire through the femoral puncture 891 to establish the femoral to subclavian through-and-through wire. This approach may be beneficial for treating a condition such as aortic dissection because it may be easier to keep the guide wire in the true lumen when the guide wire is introduced from the brachial puncture as opposed to the femoral puncture.

Figure 14D:
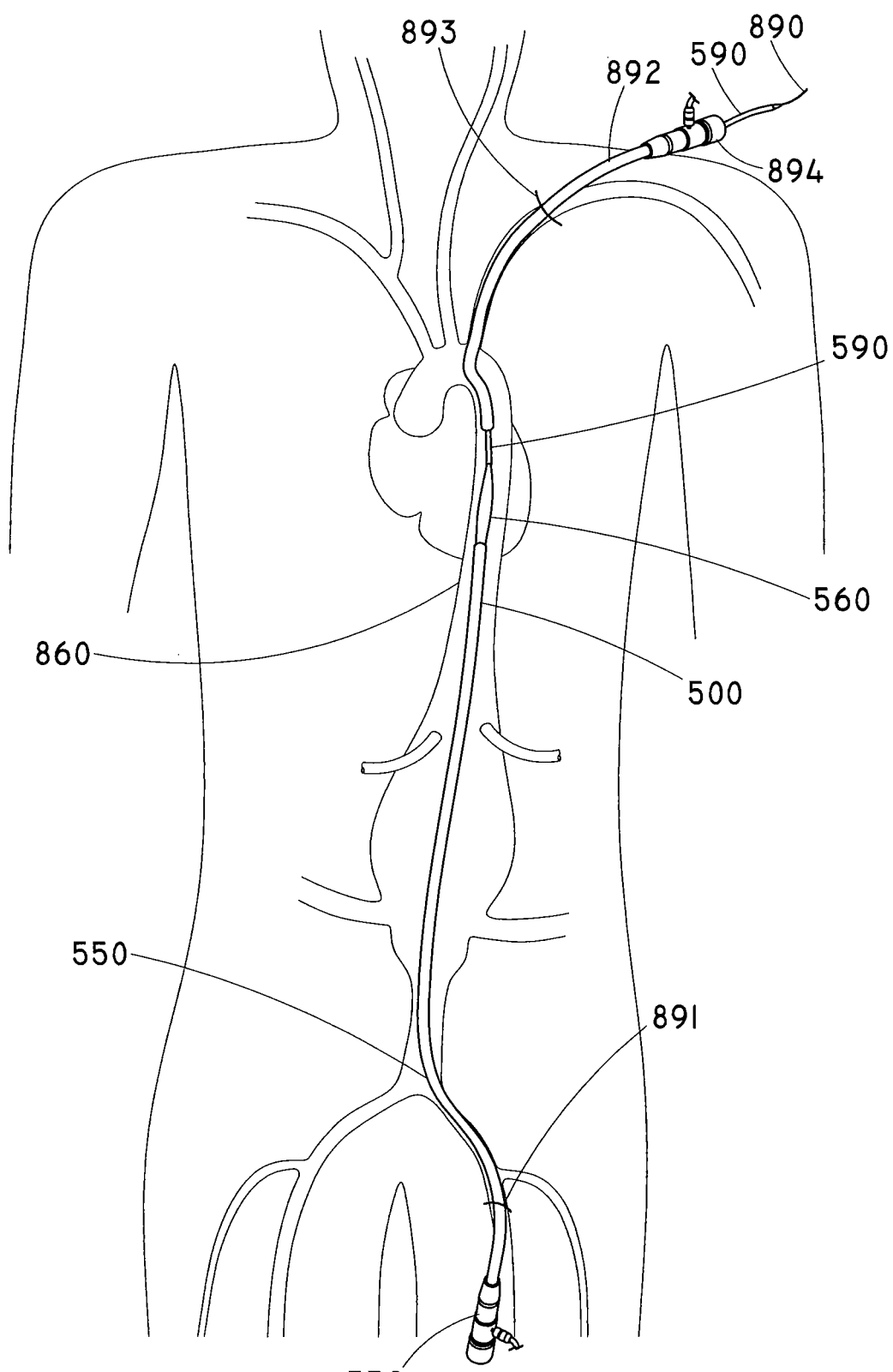
FIG. 14D illustrates an exemplary method step of tracking a delivery device over the guide wire.

The proximal end of the LEM 590 of the deployment device 500 may be introduced into the femoral artery 870b through the femoral puncture 891. The deployment device 500 may be tracked over the guide wire 890 until the proximal end of the LEM 590 emerges from the sheath hub 894 of the brachial access sheath 892 as shown in FIG. 14D. At this stage, the nose cone dilator 560 of the delivery device 500 may be positioned such that the prosthesis retained within the sheath 550 is in proximity to its desired final position within the aorta 860.

In a next stage, the ends of the auxiliary guide wire 542 may be released from the handle 510 of the delivery device 500. The auxiliary guide wire 542 may be separated slightly from the LEM 590 and severed to provide two separate guide wires. The auxiliary guide wire 542 may be severed near the cross aperture 599. In other words, the single auxiliary guide wire 542 may be severed between the first portion 542a and the second portion 542b so that the first and second portions of the auxiliary guide wire form two separate wires. In other examples, first and second wire segments may be used in place of the auxiliary guide wire 542.

Figure 14E:
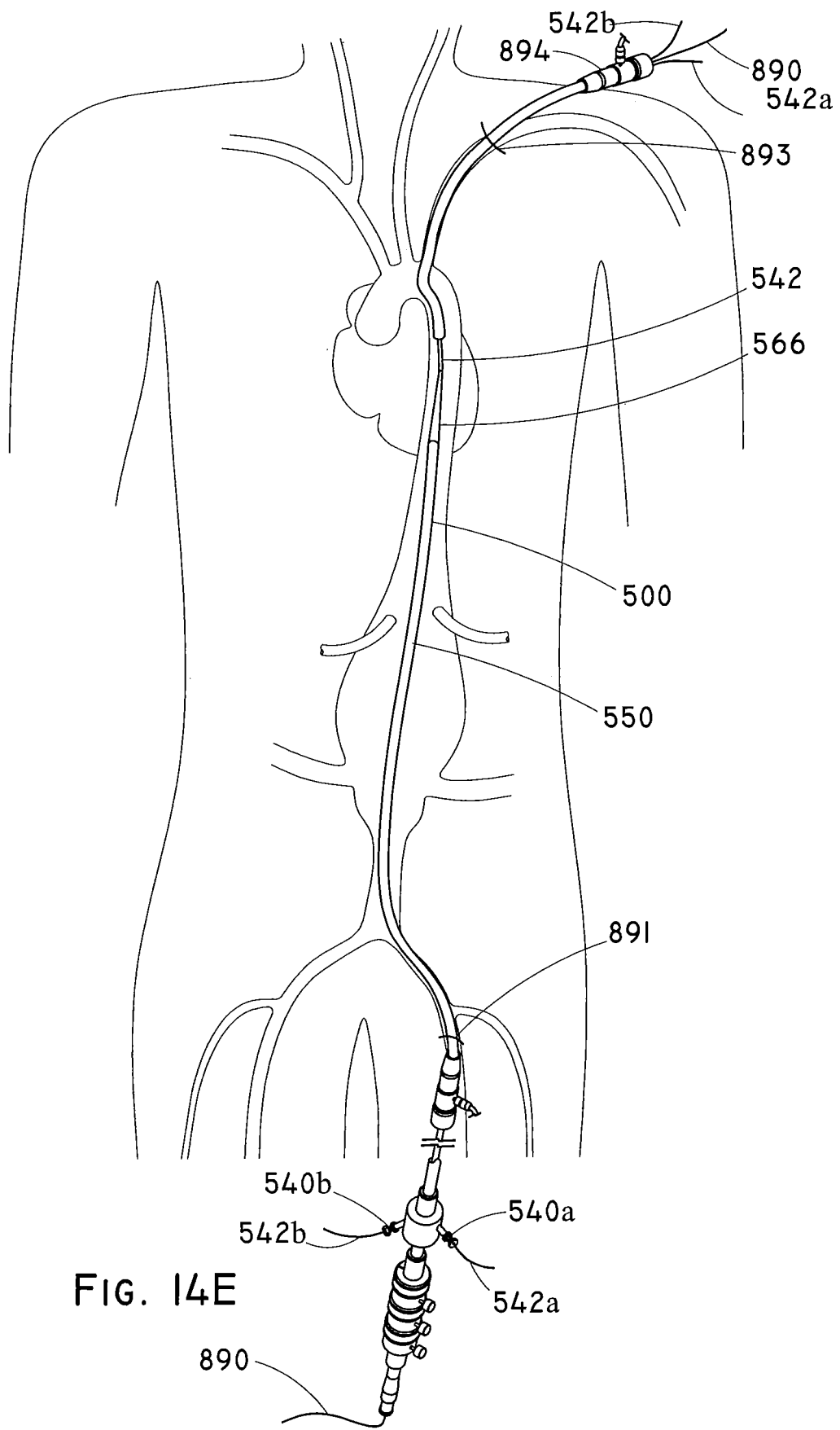
FIG. 14E shows the delivery device with a length extending module removed and auxiliary wire segments extending from the brachial access sheath.

The LEM 590 may be removed from selective engagement with the proximal end of the nose cone dilator 560. The LEM 590 may be removed from selective engagement with the nose cone dilator 560 by pulling the proximal end of the LEM 590 extending from the sheath hub 894 of the brachial access sheath 892. The LEM 590 may be removed through the sheath hub 894 of the brachial access sheath 892 such that the auxiliary guide wire 542 remains in place with each of the first and second portions 542a, 542b of the auxiliary guide wire extending out through the sheath hub 894 as shown in FIG. 14E. At this stage, the first portion 542a of the auxiliary guide wire 542 may provide through-and-through access from the femoral puncture 891 and the brachial puncture 893. Similarly, the second portion 142b of the auxiliary guide wire 142 may provide through-and-through access from the femoral puncture 891 and the brachial puncture 893.

Figure 14F:
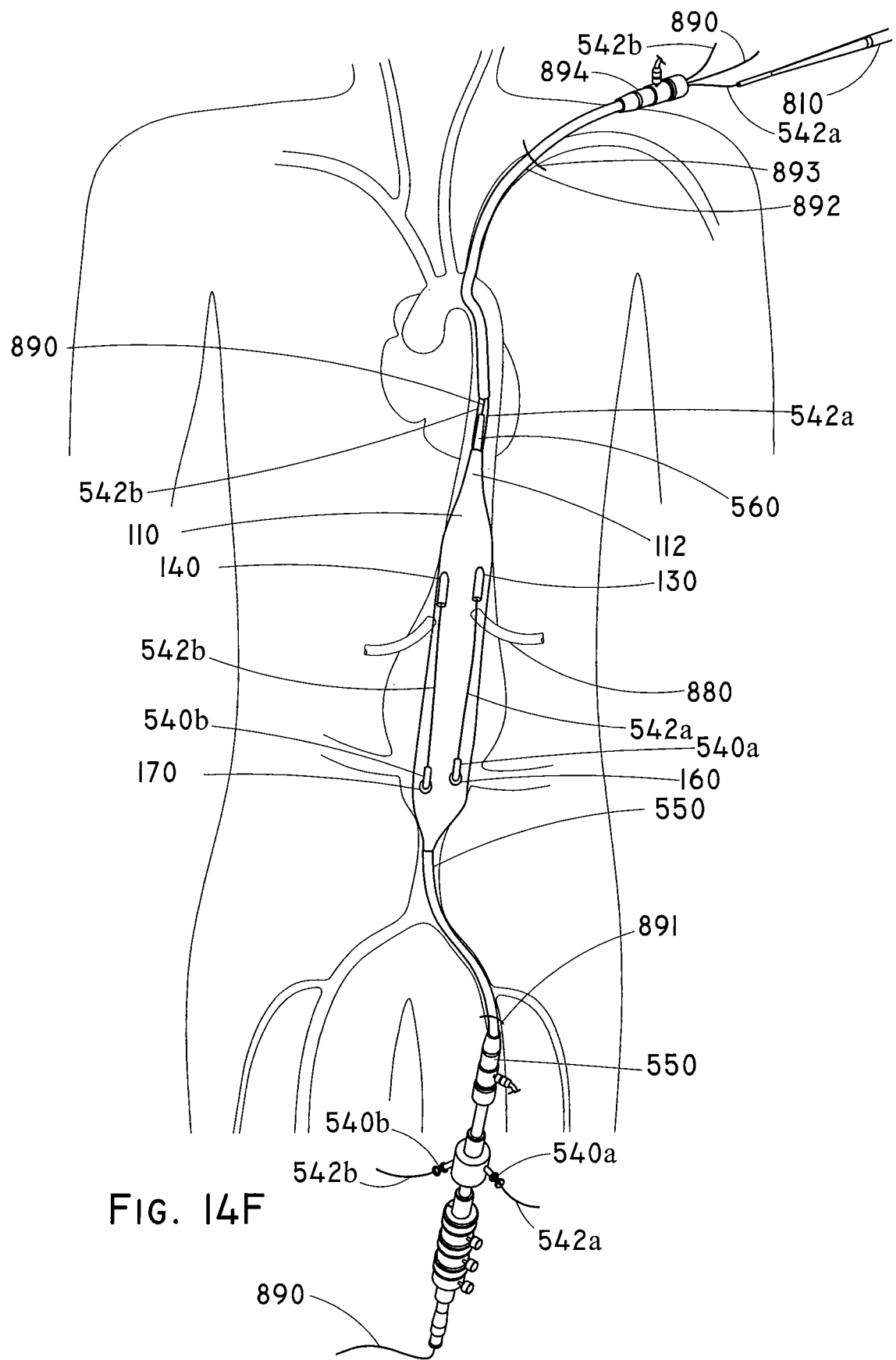
FIG. 14F illustrates an exemplary method step of retracting a sheath of the delivery device to expose an endoluminal prosthesis in an aorta of the patient.

In a next stage, the sheath hub 552 of the delivery device 500 may be retracted to partially withdraw the sheath 550 from the prosthesis as shown in FIG. 14F. Although FIG. 14F shows the delivery device 500 with the prosthesis 110 loaded thereon, the delivery device 500 may be used to deliver the prosthesis 210, or another prosthesis, in a similar manner. Upon partial withdrawal of the sheath 550, the prosthesis may at least partially expand from the reduced diameter delivery configuration. The prosthesis, or a portion of the prosthesis, may be retained in a partially expanded configuration to enable repositioning of the prosthesis within the aorta 860 prior to complete expansion of the prosthesis. In other words, the prosthesis, or a portion of the prosthesis, may be retained to prevent the prosthesis from expanding to a fully expanded configuration. In the partially expanded configuration, the retained portion of the prosthesis may have a diameter that is less than the diameter of the portion of the prosthesis in the fully expanded configuration. The prosthesis may be retained using any suitable method known in the art. In one example, the prosthesis may be retained by one or more diameter reducing ties. Each diameter reducing tie may include one or more filamentary strands extending at least partially circumferentially around the prosthesis. Each strand may engage a portion of the prosthesis and may be looped around a trigger wire to prevent expansion of the prosthesis. The diameter reducing ties may be configured generally as described in U.S. Patent Application Pub. Nos. 2004/0098084 by Hartley et al., 2006/0004433 by Greenberg et al., 2007/0043425 by Hartley et al., 2007/0142896 by Anderson et al., 2008/0114438 by Hartley et al., or 2008/0294234 by Hartley et al. In another example, the prosthesis may be retained by one or more filamentary strands circumscribing the prosthesis. The strands may be engaged by one or more trigger wires to maintain tension on the strands to retain the prosthesis from expanding. In any of these examples, the proximal end, the distal end, and/or any other portion of the prosthesis may be retained from expanding to the fully expanded configuration. Additionally, or alternatively, the proximal end of the prosthesis may be retained (e.g., by one or more trigger wires) to form the lobes of graft material as described above. Such retention of the proximal end of the prosthesis may enable repositioning of the prosthesis within the aorta 860 prior to complete expansion of the prosthesis. Additionally, or alternatively, the distal end of the prosthesis may be retained within the sheath to prevent expansion of the distal end of the prosthesis. Such retention of the distal end of the prosthesis may enable repositioning of the prosthesis within the aorta 860 prior to complete expansion of the prosthesis.

FIGS. 15A-15G illustrate exemplary method steps for deploying the prosthesis 110. The first portion 542a of the auxiliary guide wire 542 may provide clear access to the first branch 130 of the prosthesis 110 from the brachial puncture 893 and clear access to the first fenestration 160 of the prosthesis from the femoral puncture 891 as further described below. The second portion 542b of the auxiliary guide wire 542 may provide clear access to the second branch 140 of the prosthesis 110 from the brachial puncture 893 and clear access to the second fenestration 170 of the prosthesis from the femoral puncture 891 also as further described below.

Figure 15A:
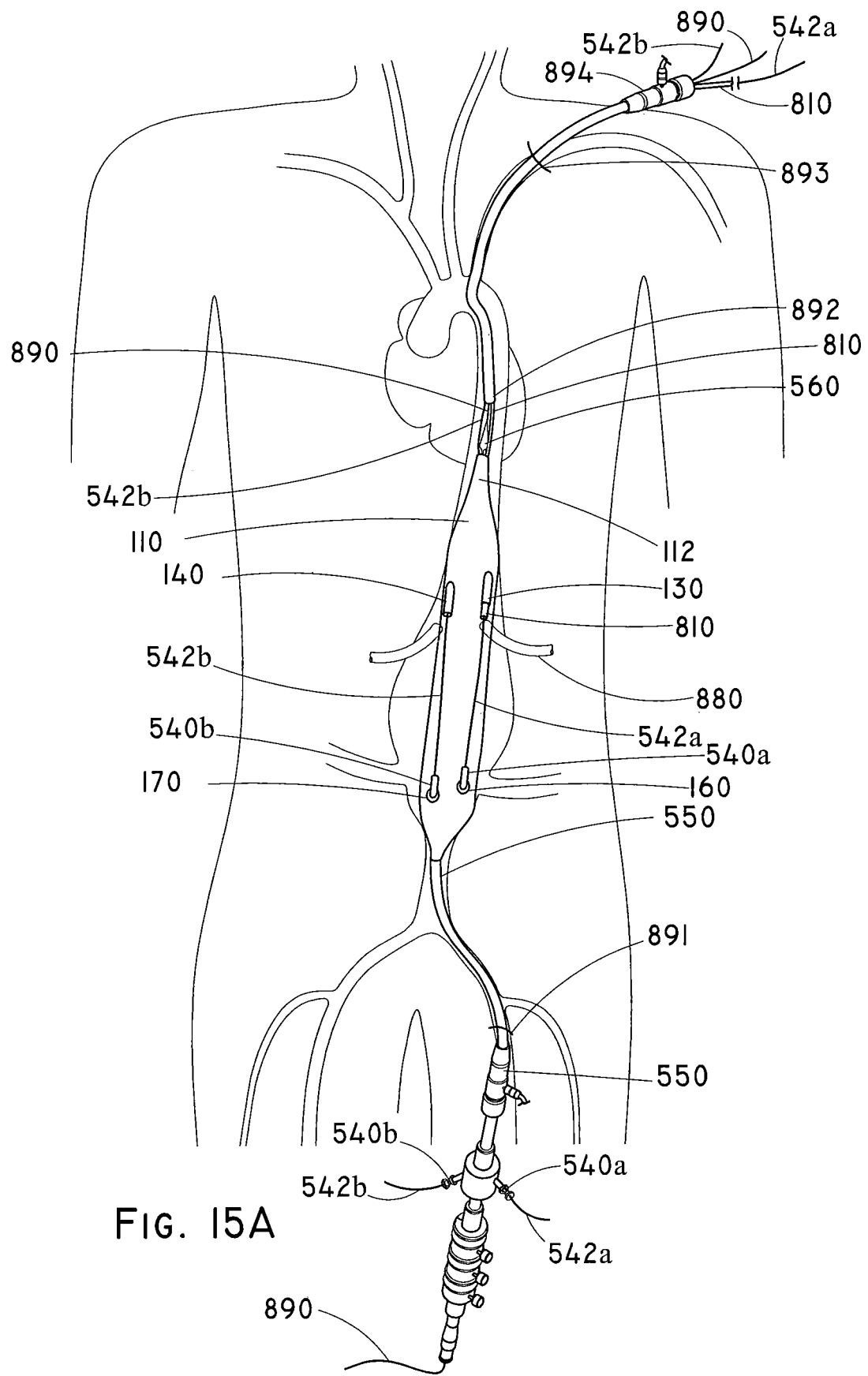
FIGS. 15A-15C illustrate exemplary method steps of the cannulation of each of a celiac artery and a left renal artery of the patient.

A sheath 810 may be advanced over the first portion 542a of the auxiliary guide wire 542, through the sheath hub 894, and through the brachial access sheath 892. The sheath 810 may be advanced from the brachial artery distally down the aorta 860. In one example, the sheath 810 may have a size ranging from about 6 Fr to about 7 Fr. In another example, the sheath 810 may have a size ranging from about 8 Fr to about 10 Fr. A dilator (not shown) may be positioned within the sheath 810 to aid in advancing the sheath 810 through the brachial access sheath 892. The sheath 810 may be advanced distally through the lumen 135 of the first branch 130 of the prosthesis 110, and disposed adjacent to the celiac artery 880 as shown in FIG. 15A. If a dilator is used, then after desired placement of the sheath 810, the dilator may be withdrawn proximally out of the patient's anatomy via the brachial artery, leaving the sheath 810 in place near the celiac artery 880.

Figure 15B:
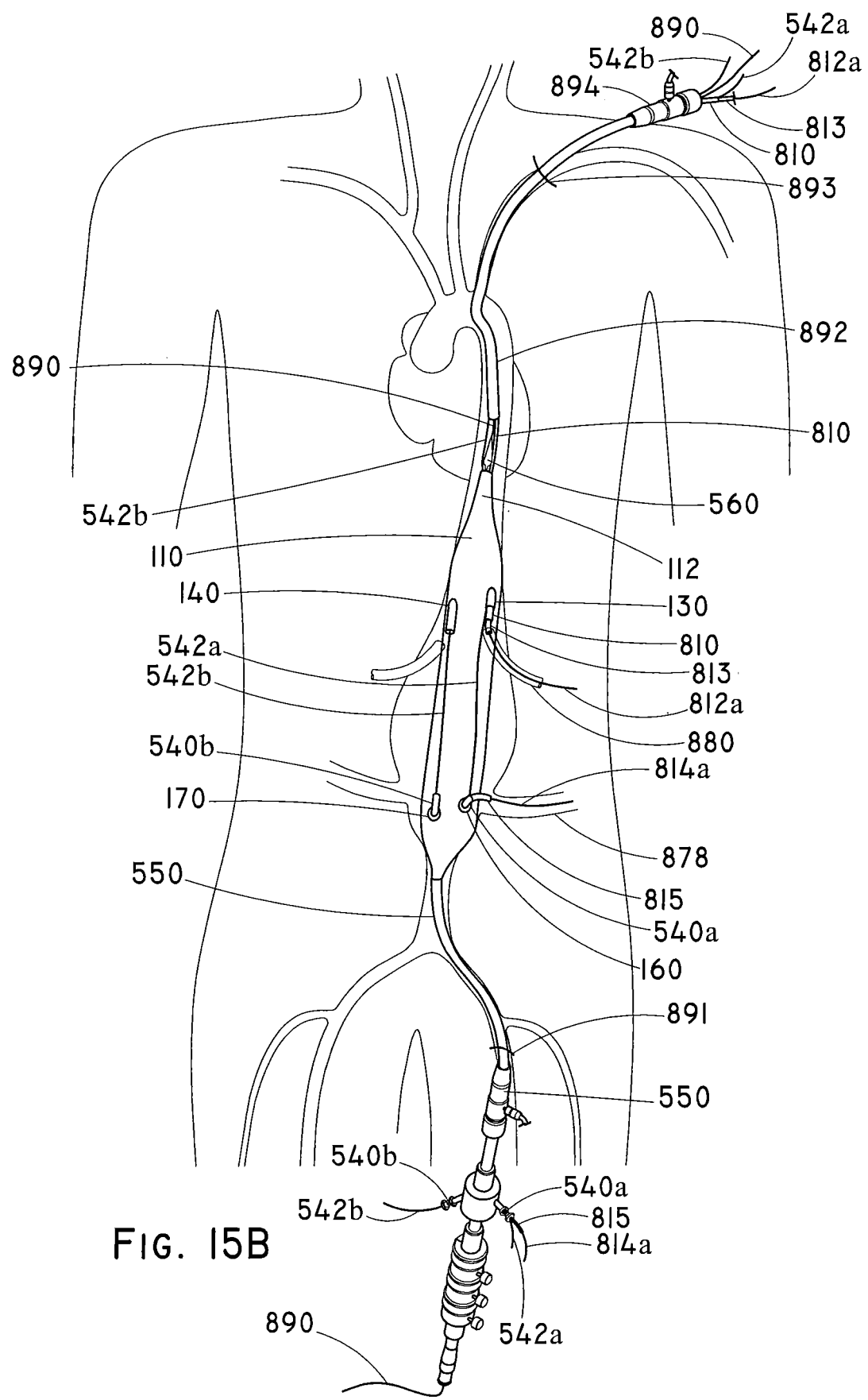
Figure 15C:
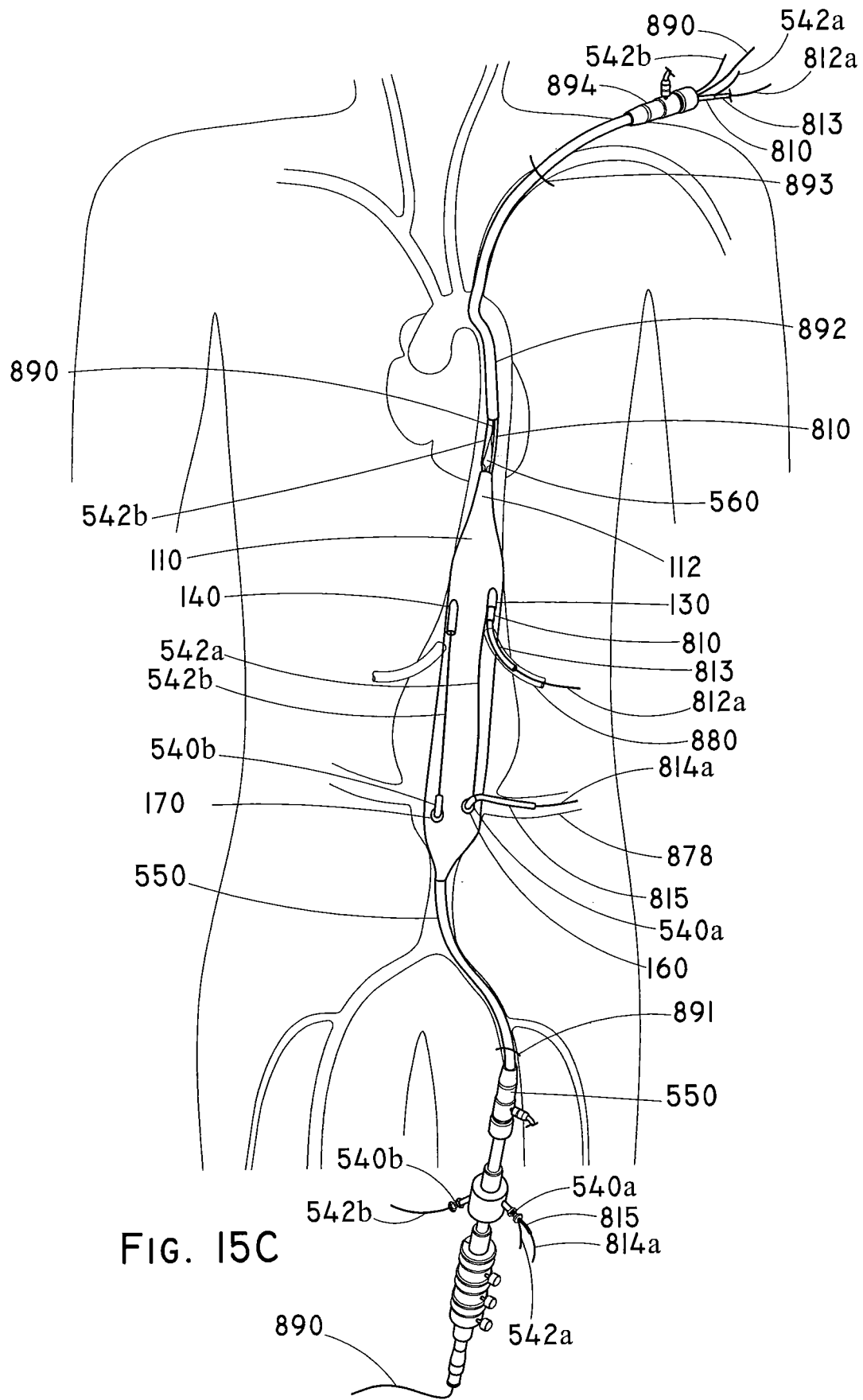

In a next stage, a wire guide 812a may be introduced via the sheath 810. The wire guide 812a may be advanced within the sheath 810, within the prosthesis 110, and out the first branch 130 to exit the sheath 810 and enter the celiac artery 880 as shown in FIG. 15B. The wire guide 812a may be received within a catheter 813, which may be introduced with the wire guide 812a via the sheath 810. The catheter 813 may aid in guiding the wire guide 812a into the celiac artery 880. To that end, the catheter 813 may be advanced such that a distal end of the catheter 813 is positioned proximate the ostium of the celiac artery 880 as shown in FIG. 15B. The wire guide 812a and the catheter 813 may be further advanced into the celiac artery 880 as shown in FIG. 15C.

A wire guide 814a may be introduced via the first auxiliary sheath 540a. The wire guide 814a may be introduced into the first auxiliary sheath 540a at the pusher catheter hub 532. Introduction of a sheath (e.g., the sheath 810) may be unnecessary because the wire guide 814a may be introduced directly into the first auxiliary sheath 540a, which may be preloaded into the prosthesis 110 as described above. The wire guide 814a may be advanced within the first auxiliary sheath 540a, through the side port 534a of the pusher catheter hub 532, and through the pusher catheter 530. The wire guide 814a may be advanced within the prosthesis 110 and out the first fenestration 160 to exit the first auxiliary sheath 540a and enter the left renal artery 878 as shown in FIG. 15B. The wire guide 814a may be received within a catheter 815, which may be introduced with the wire guide 814a via the first auxiliary sheath 540a. The catheter 815 may aid in guiding the wire guide 814a into the left renal artery 878. To that end, the catheter 815 may be advanced such that a proximal end of the catheter 815 is positioned proximate the ostium of the left renal artery 878 as shown in FIG. 15B. The wire guide 814a and the catheter 815 may be further advanced into the left renal artery 878 as shown in FIG. 15C.

In one example, the wire guide 812a and the catheter 813 may be introduced to cannulate the celiac artery 880 before the wire guide 814a and the catheter 815 are introduced to cannulate the left renal artery 878. In another example, the wire guide 814a and the catheter 815 may be introduced to cannulate the left renal artery 878 before the wire guide 812a and the catheter 813 are introduced to cannulate the celiac artery 880. In yet another example, the wire guide 812a and the catheter 813 and the wire guide 814a and the catheter 815 may be introduced substantially simultaneously to cannulate the celiac artery 880 and the left renal artery 878, respectively, at substantially the same time. In any of the examples described herein, the various visceral arteries may be cannulated in any suitable sequence, and side branch prostheses may be deployed into the various visceral arteries in any suitable sequence.

Figure 15D:
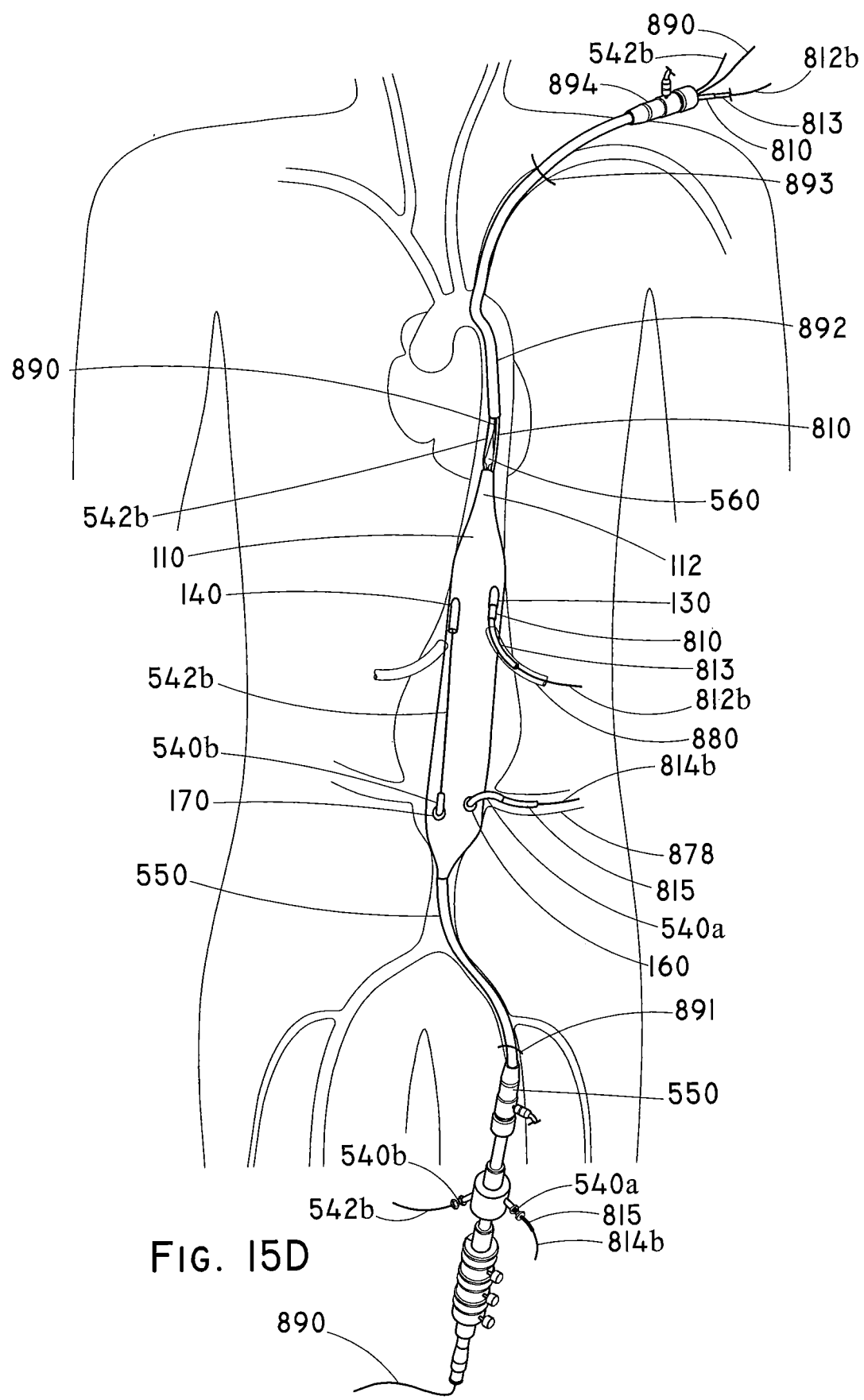
FIGS. 15D-15F illustrate exemplary method steps of deploying a side branch prosthesis in each of a branch and a fenestration of the endoluminal prosthesis of FIG. 1.

The wire guide 812a may be retracted proximally relative to the catheter 813 and the sheath 810 to remove the wire guide 812a from the patient's body. A wire guide 812b may be introduced through the catheter 813 and the sheath 810 in a distal direction from the brachial artery and ultimately into the celiac artery 880 as shown in FIG. 15D. In other words, the wire guide 812a may be replaced with the wire guide 812b. The wire guide 812b may have a stiffness that is greater than a stiffness of the wire guide 812a. The wire guide 814a may be retracted distally relative to the catheter 815 and the first auxiliary sheath 540a to remove the wire guide 814a from the patient's body. A wire guide 814b may be introduced through the catheter 815 and the first auxiliary sheath 540a in a proximal direction from the femoral artery and ultimately into the left renal artery 878 as shown in FIG. 15D. In other words, the wire guide 814a may be replaced with the wire guide 814b. The wire guide 814b may have a stiffness that is greater than a stiffness of the wire guide 814a.

The position of the first portion 542a of the auxiliary guide wire 542 in the first branch 130 and the first fenestration 160 may aid in cannulation of the celiac artery 880 and the left renal artery 878. For example, the first portion 542a of the auxiliary guide wire 542 may provide stability to the prosthesis 110 during introduction or movement of various components (e.g., sheaths, wire guides, or catheters) as described herein. With the catheter 813 and the wire guide 812b in place within the celiac artery 880 and the catheter 815 and the wire guide 814b in place within the left renal artery 878, the first portion 542a of the auxiliary guide wire 542 may be removed from the patient's body. The first portion 542a of the auxiliary guide wire 542 may be retracted distally away from the brachial artery and removed from the patient's body via the femoral artery. Alternatively, the first portion 542a of the auxiliary guide wire 542 may be retracted proximally away from the femoral artery and removed from the patient's body via the brachial artery.

Figure 15E:
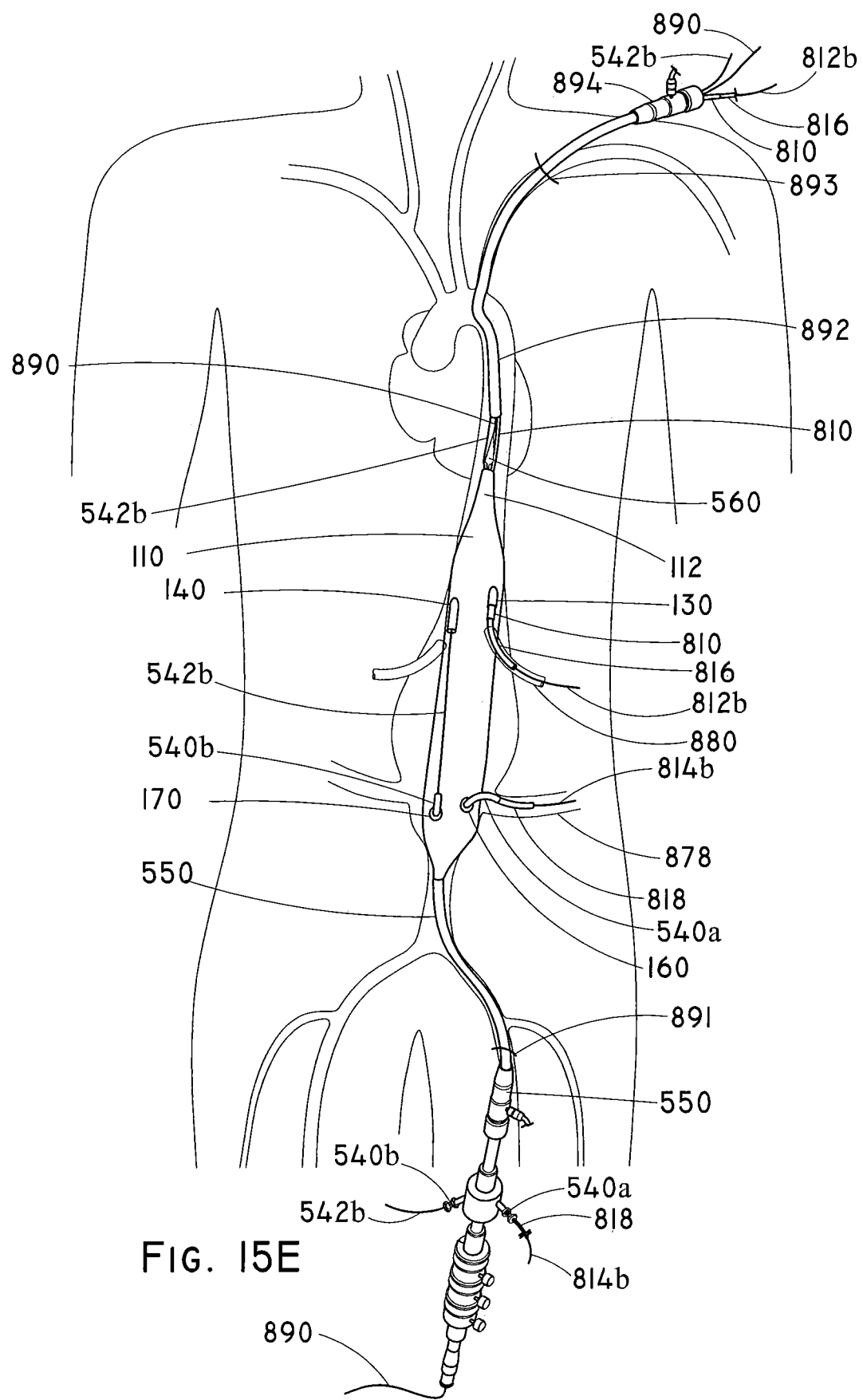

The catheter 813 may be retracted proximally relative to the sheath 810 and removed from the patient's body. The wire guide 812b may remain in place within the celiac artery 880 as shown in FIG. 15E. The first auxiliary sheath 540a may be advanced proximally over the catheter 815 and the wire guide 814b and into the left renal artery 878 as shown in FIG. 15D. With the first auxiliary sheath 540a in place within the left renal artery 878, the catheter 815 may be retracted distally relative to the first auxiliary sheath 540a and removed from the patient's body. The first auxiliary sheath 540a and the wire guide 814b may remain in place within the left renal artery 878 as shown in FIG. 15E. The position of the wire guide 812b in the celiac artery 880 may enable delivery of a side branch prosthesis into the celiac artery 880 using any suitable endovascular delivery technique. The position of the first auxiliary sheath 540a and the wire guide 814b in the left renal artery 878 may enable delivery of a side branch prosthesis into the left renal artery 878 using any suitable endovascular technique.

In a next stage, a side branch prosthesis 820 may be deployed in the celiac artery 880. The side branch prosthesis 820 (and the side branch prostheses 830, 840, 850 described below) may be formed of biocompatible materials and may be configured as covered stents. Alternatively, the side branch prostheses may be configured as bare stents. The covered or bare stents may be either self-expanding or balloon expandable. In one embodiment, a side branch prosthesis may have both self-expanding and balloon expandable components. For example, a side branch prosthesis may have an end for placement within a branch or fenestration of the prosthesis that is, upon deployment, either self-expanding or balloon expandable. By way of example and without limitation, the side branch prostheses may include the Fluency® Plus Vascular Stent Graft from Bard Peripheral Vascular, Helsingborg, Sweden, or the Jostent® Peripheral Stent Graft from Abbott Vascular, Abbott Park, Illinois.

Figure 15F:
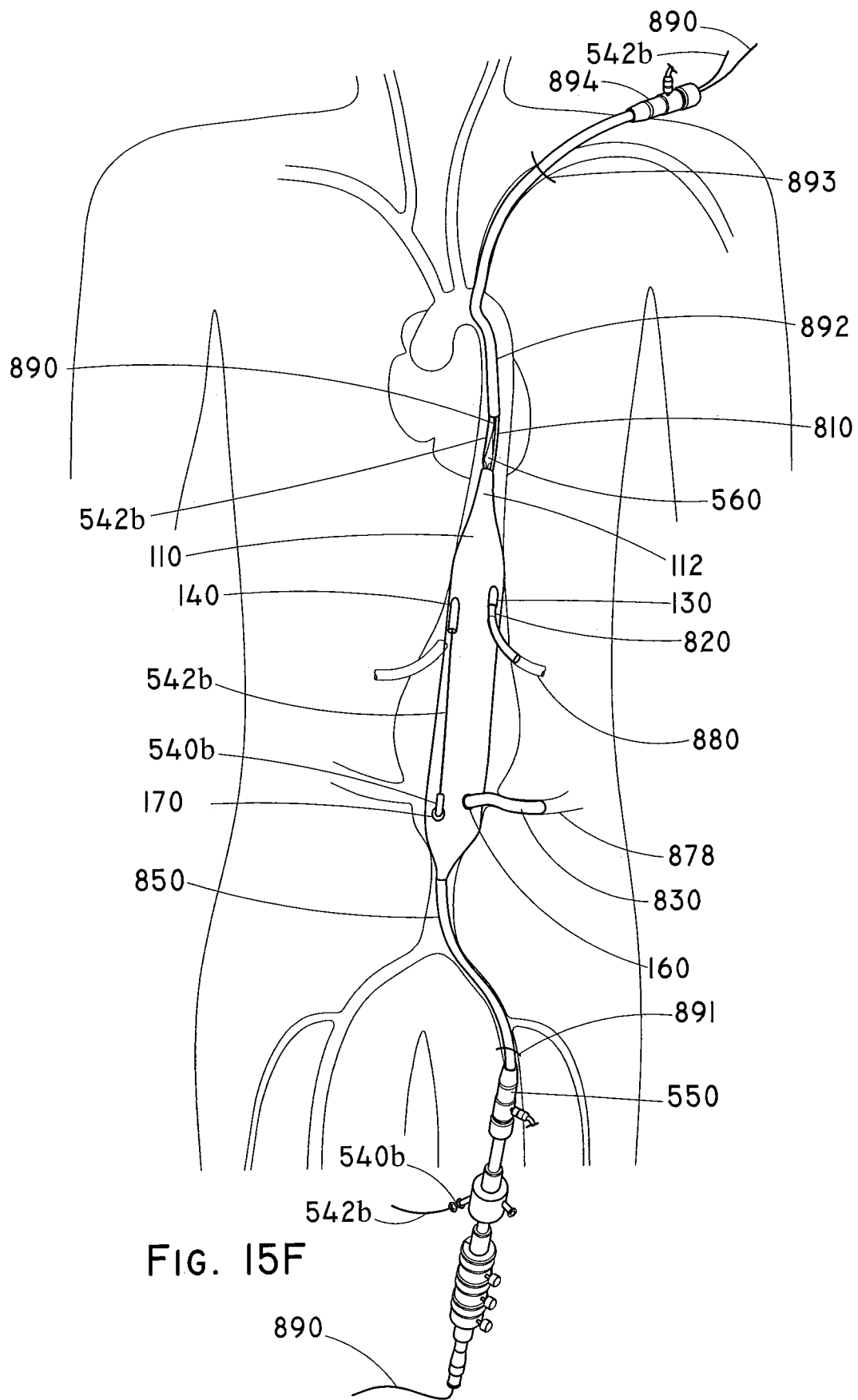

The side branch prosthesis 820 may be compressed into a delivery state and delivered using a suitable deployment system or introducer. For example, an introducer 816 may include a delivery catheter and an outer sheath. In another example, the outer sheath may be omitted from the introducer. The side branch prosthesis 820 may be radially compressed onto the delivery catheter of the introducer 816 and covered by the outer sheath. The introducer 816 may be introduced over the wire guide 812b and through the sheath 810 in a distal direction from the brachial artery and ultimately into the celiac artery 880 as shown in FIG. 15F. The side branch prosthesis 820 may be deployed from the introducer 816 (e.g., by retraction of the sheath of the introducer). Upon deployment, the side branch prosthesis 820 may extend from the first branch 130 of the prosthesis 110 into the celiac artery 880 as shown in FIG. 15F. The side branch prosthesis 820 and the first branch 130 of the prosthesis 110 may be mated such that there is a suitable tromboning connection, preferably with a 1.5 to 2 cm overlap and a 1 mm or less difference in diameter at the interconnection. Optionally, the devices may be expanded for about 30 seconds using a suitably sized balloon dilation catheter. At this time, the side branch prosthesis 820 may provide patent fluid flow through the prosthesis 110 into the celiac artery 880. The introducer 816, the wire guide 812b, and the sheath 810 then may be withdrawn proximally out of the patient's body via the brachial artery.

A side branch prosthesis 830 may be deployed in the left renal artery 878. The side branch prosthesis 830 may be compressed into a delivery state and delivered using a suitable deployment system or introducer. For example, the side branch prosthesis 830 may be delivered using an introducer 818, which may be configured generally as described above with reference to the introducer 816. The introducer 818 may be introduced over the wire guide 814b and through the first auxiliary sheath 540a in a proximal direction from the femoral artery and ultimately into the left renal artery 878 as shown in FIG. 15E. With the introducer 818 in place within the left renal artery 878, the first auxiliary sheath 540a may be retracted distally relative to the introducer 818 and removed from the left renal artery. The side branch prosthesis 830 may be deployed from the introducer 818. Upon deployment, the side branch prosthesis 830 may extend from the first fenestration 160 into the left renal artery 878 as shown in FIG. 15F. Upon deployment, the side branch prosthesis 830 and the first fenestration 160 may be mated. Optionally, the devices may be expanded for about 30 seconds using a suitably sized balloon dilation catheter. At this time, the side branch prosthesis 830 may provide patent fluid flow through the prosthesis 110 into the left renal artery 878. The introducer 818, the wire guide 814b, and the first auxiliary sheath 540a then may be withdrawn distally out of the patient's body via the femoral artery.

In one example, the side branch prosthesis 820 may be deployed in the celiac artery 880 before the side branch prosthesis 830 is deployed in the left renal artery 878. In another example, the side branch prosthesis 830 may be deployed in the left renal artery 878 before the side branch prosthesis 820 is deployed in the celiac artery 880. In yet another example, the side branch prosthesis 820 and the side branch prosthesis 830 may be deployed substantially simultaneously in the celiac artery 880 and the left renal artery 878, respectively, at substantially the same time.

Side branch prostheses may be deployed within the second branch 140 and the second fenestration 170 in the same manner as described above in reference to the first branch 130 and the first fenestration 160. For example, in a next stage, a first sheath, which may be configured as described above with reference to the sheath 810, may be advanced over the second portion 542b of the auxiliary guide wire 542, through the sheath hub 894, and through the brachial access sheath 892. In other examples, the sheath 810 may be substituted for the first sheath. The first sheath may be advanced from the brachial artery distally down the aorta 860. The first sheath may be advanced distally through the lumen 145 of the second branch 140, and disposed adjacent to the superior mesenteric artery 879.

In a next stage, a first wire guide, which may be configured as described above with reference to the wire guide 812a, may be introduced via the first sheath. The first wire guide may be advanced within the first sheath, within the prosthesis 110, and out the second branch 140 to exit the first sheath and enter the superior mesenteric artery 879. In other examples, the wire guide 812*a* may be substituted for the first wire guide. The first wire guide may be received within a first catheter, which may be configured as described above with reference to the catheter 813. The first catheter may be introduced with the first wire guide via the first sheath. The first catheter may be advanced such that a distal end of the first catheter is positioned proximate the ostium of the superior mesenteric artery 879. The first wire guide and the first catheter may be further advanced into the superior mesenteric artery 879.

A second wire guide, which may be configured as described above with reference to the wire guide 814*a*, may be introduced via the second auxiliary sheath 540*b*. The second wire guide may be introduced into the second auxiliary sheath 540*b* at the pusher catheter hub 532. Introduction of a sheath (e.g., the sheath 810) may be unnecessary because the second wire guide may be introduced directly into the second auxiliary sheath 540*b*, which may be preloaded into the prosthesis 110 as described above. The second wire guide may be advanced within the second auxiliary sheath 540*b*, through the side port 534*b* of the pusher catheter hub 532, and through the pusher catheter 530. The second wire guide may be advanced within the prosthesis 100 and out the second fenestration 170 to exit the second auxiliary sheath 540*b* and enter the right renal artery 877. In other examples, the wire guide 814*a* may be substituted for the second wire guide. The second wire guide may be received within a second catheter, which may be configured as described above with reference to the catheter 815. The second catheter may be introduced with the second wire guide via the second auxiliary sheath 540*b*. The second catheter may be advanced such that a proximal end of the second catheter is positioned proximate the ostium of the right renal artery 877. The second wire guide and the second catheter may be further advanced into the right renal artery 877.

In one example, the first wire guide and the first catheter may be introduced to cannulate the superior mesenteric artery 879 before the second wire guide and the second catheter are introduced to cannulate the right renal artery 877. In another example, the second wire guide and the second catheter may be introduced to cannulate the right renal artery 877 before the first wire guide and the first catheter are introduced to cannulate the superior mesenteric artery 879. In yet another example, the first wire guide and the first catheter and the second wire guide and the second catheter may be introduced substantially simultaneously to cannulate the superior mesenteric artery 879 and the right renal artery 877, respectively, at substantially the same time.

The first wire guide may be removed from the patient's body and replaced with a third wire guide, which may be configured as described above with reference to the wire guide 812*b*. The second wire guide may be removed from the patient's body and replaced with a fourth wire guide, which may be configured as described above with reference to the wire guide 814*b*. With the first catheter and the third wire guide in place within the superior mesenteric artery 879 and the second catheter and the fourth wire guide in place within the right renal artery 877, the second portion 542*b* of the auxiliary guide wire 542 may be removed from the patient's body.

The first catheter may be removed from the patient's body while the third wire guide may remain in place within the superior mesenteric artery 879. The second auxiliary sheath 540*b* may be advanced proximally over the second catheter and the fourth wire guide and into the right renal artery 877. The second catheter may be removed from the patient's body while the second auxiliary sheath 540*b* and the fourth wire guide may remain in place within the right renal artery 877. At this stage, the positions of the third wire guide in the superior mesenteric artery 879 and the second auxiliary sheath 540*b* and the fourth wire guide in the right renal artery 877 may enable delivery of a side branch prosthesis into each of the superior mesenteric artery 879 and the right renal artery 877 using any suitable endovascular technique.

Figure 15G:
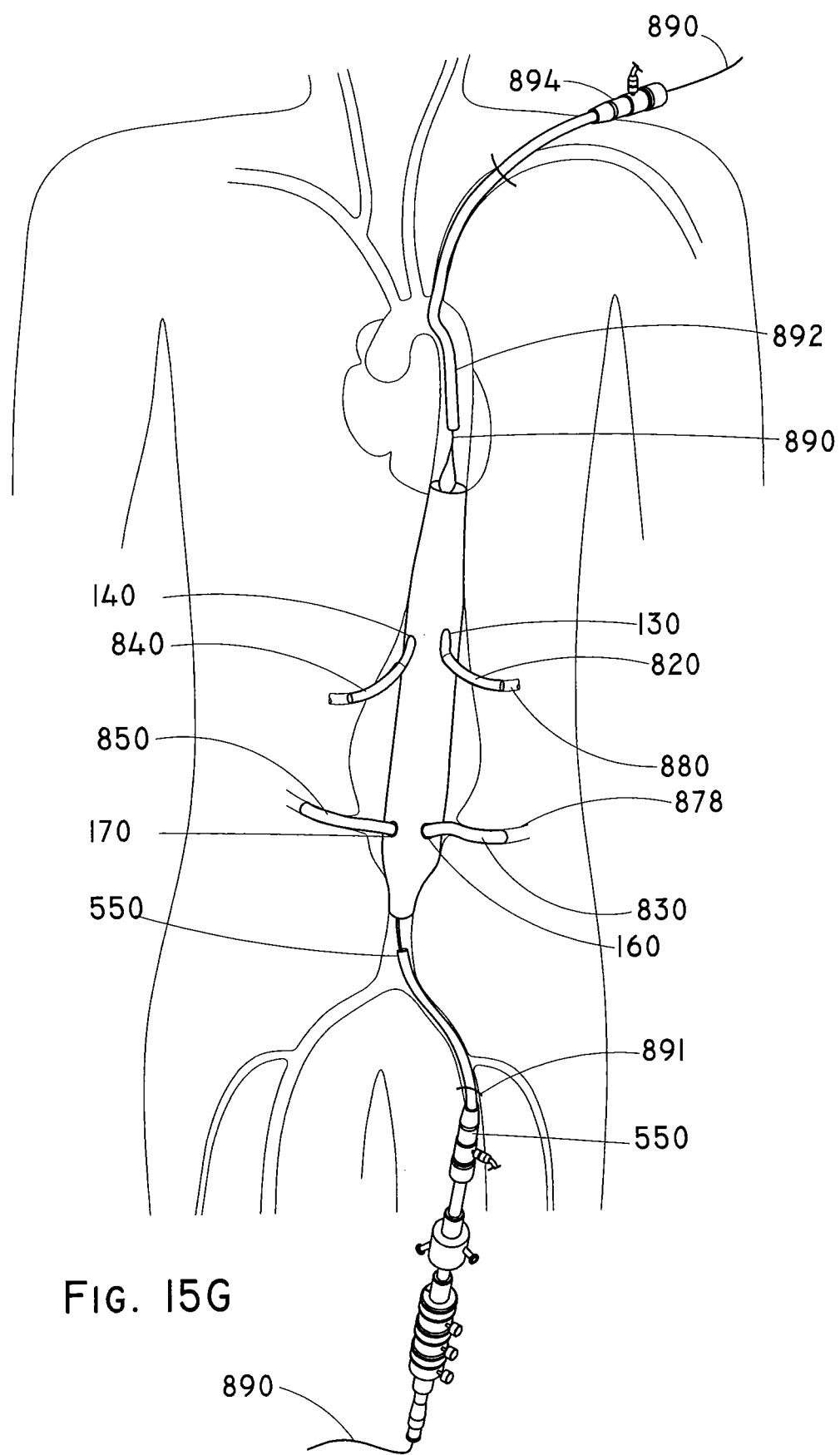
FIG. 15G shows the endoluminal prosthesis of FIG. 1 deployed within the aorta of the patient.

In a next stage, a side branch prosthesis 840 may be deployed in the superior mesenteric artery 879. The side branch prosthesis 840 may be compressed into a delivery state and delivered using a first introducer, which may be configured as described above with reference to the introducer 816. The first introducer 816 may be introduced over the third wire guide and through the first sheath in a distal direction from the brachial artery and ultimately into the superior mesenteric artery 879. The side branch prosthesis 840 may be deployed from the first introducer. Upon deployment, the side branch prosthesis 840 may extend from the second branch 140 of the prosthesis 110 into the superior mesenteric artery 879 as shown in FIG. 15G. The side branch prosthesis 840 and the second branch 140 of the prosthesis 110 may be mated such that there is a suitable tromboning connection as described above. Optionally, the devices may be expanded for about 30 seconds using a suitably sized balloon dilation catheter. At this time, the side branch prosthesis 840 may provide patent fluid flow through the prosthesis 110 into the superior mesenteric artery 879. The first introducer, the third wire guide, and the first sheath then may be withdrawn proximally out of the patient's body via the brachial artery.

A side branch prosthesis 850 may be deployed in the right renal artery 877. The side branch prosthesis 850 may be compressed into a delivery state and delivered using a second introducer, which may be configured as described above with reference to the introducer 818. The second introducer may be introduced over the fourth wire guide and through the second auxiliary sheath 540*b* in a proximal direction from the femoral artery and ultimately into the right renal artery 877. The side branch prosthesis 850 may be deployed from the second introducer. Upon deployment, the side branch prosthesis 850 may extend from the second fenestration 170 into the right renal artery 877 as shown in FIG. 15G. Upon deployment, the side branch prosthesis 850 and the second fenestration 170 may be mated. Optionally, the devices may be expanded for about 30 seconds using a suitably sized balloon dilation catheter. At this time, the side branch prosthesis 850 may provide patent fluid flow through the prosthesis 110 into the right renal artery 877. The second introducer, the fourth wire guide, and the second auxiliary sheath 540*b* then may be withdrawn distally out of the patient's body via the femoral artery.

In one example, the side branch prosthesis 840 may be deployed in the superior mesenteric artery 879 before the side branch prosthesis 850 is deployed in the right renal artery 877. In another example, the side branch prosthesis 850 may be deployed in the right renal artery 877 before the side branch prosthesis 840 is deployed in the superior mesenteric artery 879. In yet another example, the side branch prosthesis 840 and the side branch prosthesis 850 may be deployed substantially simultaneously in the superior mesenteric artery 879 and the right renal artery 877, respectively, at substantially the same time.

The configuration and placement of the various branches 130, 140 and fenestrations 160, 170 along the graft 112 may provide the ability to manipulate the first and second portions 542*a*, 542*b* or the auxiliary guide wire 542 and delivery components in a manner that will allow for relatively quick delivery of four different side branch prostheses. The preloaded system provided by the present embodiments may save multiple steps and significant time during a surgical operation.

The access provided by the auxiliary guide wire 542 into each of the openings in the prosthesis 110 corresponding to each of the visceral arteries may enable multiple side branch prostheses to be deployed substantially simultaneously. For example, one physician may deploy side branch prostheses into the celiac and/or superior mesenteric arteries from the brachial puncture 893 while a second physician deploys side branch prostheses into the left and/or right renal arteries from the femoral puncture 891. In another example, a first physician may deploy a side branch prosthesis into the celiac artery 880 from the brachial puncture 893 while a second physician may deploy a side branch prosthesis into the superior mesenteric artery 879 from the brachial puncture. At the same time, a third physician may deploy a side branch prosthesis into the left renal artery 878 from the femoral puncture 891 while a fourth physician may deploy a side branch prosthesis into the right renal artery 877. In this example, four physicians may deploy four side branch prostheses (one in each of the visceral arteries) substantially simultaneously. The ability to deploy side branch prostheses from both ends of the delivery device 500 (e.g., from the femoral access and the brachial access) substantially simultaneously may reduce the amount of time that may be required to perform a deployment procedure. Multiple access sites may allow for substantially simultaneous cannulation of vessels, which may decrease the time required to perform a procedure and the patient's exposure to x-rays or fluoroscopy contrast.

Once a side branch prosthesis has been deployed into each of the visceral arteries, the sheath 550 may be further retracted to release the distal end 119 of the prosthesis 110, and the proximal retention mechanisms may be activated to release the proximal end 118 of the prosthesis. Releasing the distal end 119 and the proximal end 118 of the prosthesis 110 may enable the prosthesis to expand to a fully expanded deployed configuration as shown in FIG. 15G. The delivery device 500 then may be retracted through the femoral puncture 891, and the brachial access sheath 892 may be retracted through the brachial puncture 893.

Figure 16:
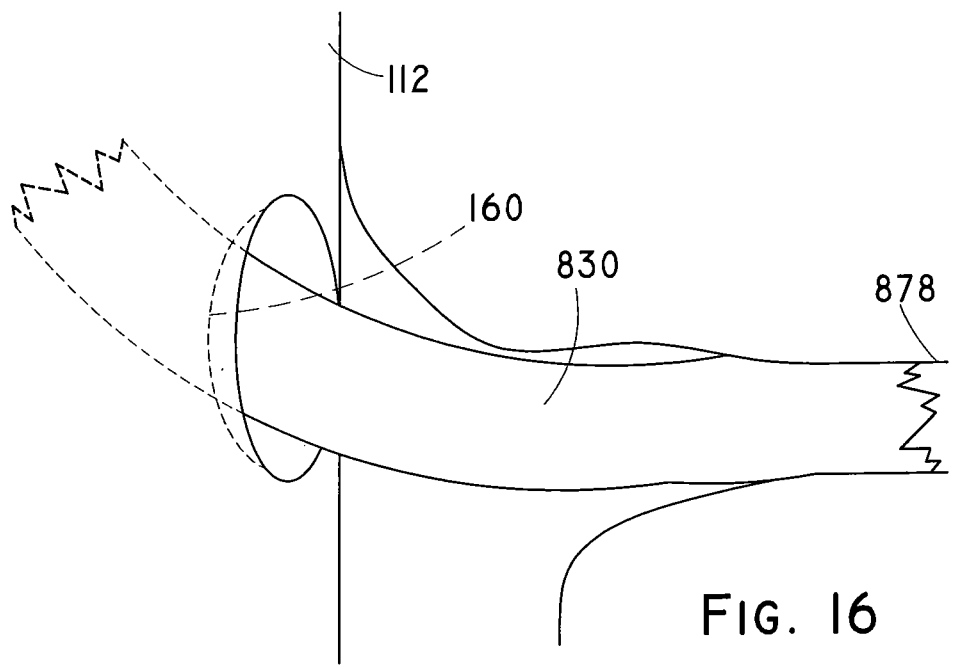
FIG. 16 illustrates a branch prosthesis deployed in a left branch vessel, where the left branch vessel is positioned lower than the corresponding right branch vessel.
Figure 17:
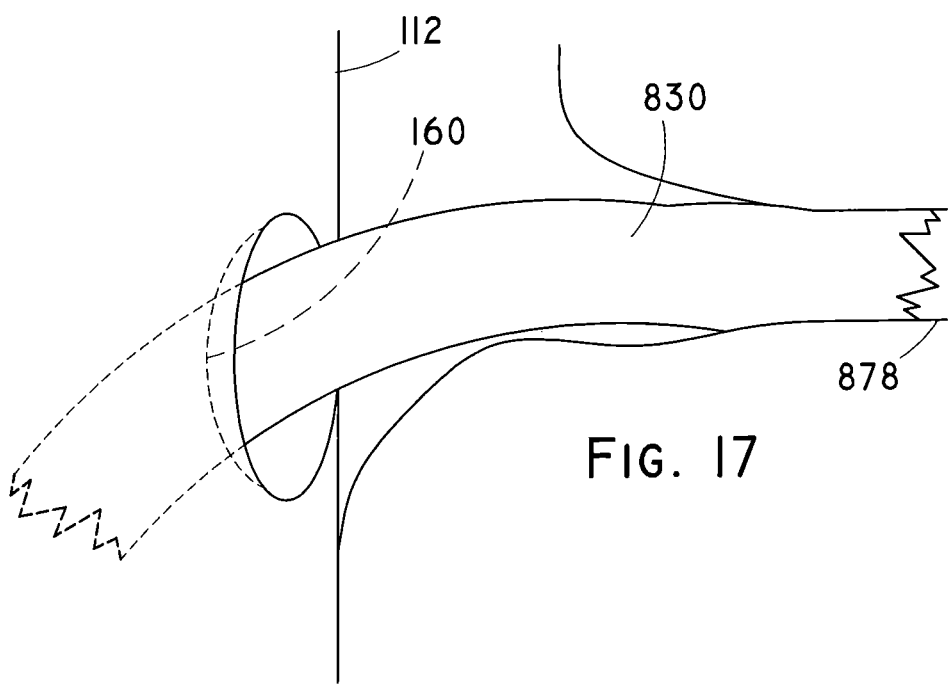
FIG. 17 illustrates a branch prosthesis deployed in a left branch vessel, where the left branch vessel is positioned higher than the corresponding right branch vessel.

As shown in FIGS. 16-17, the fenestrations 160, 170 of the prosthesis 110 may not align completely with the branch vessels of the patient. The fenestrations may not align because, for example, the patient's left renal artery 878 may be may be positioned higher than the patient's right renal artery 877, or vice versa. To accommodate placement of the side branch prostheses 830, 850 into the left and right renal arteries 878, 877, the fenestrations 160, 170 may be configured as pivot fenestrations as described above to provide flexibility and ability to pivot so that the side branch prostheses 830, 850 may be deployed into the left and right renal arteries 878, 877.

FIGS. 16-17 show the side branch prosthesis 830 deployed in the left renal artery 878 in greater detail. In one example, shown in FIG. 16, the side branch prosthesis 830 may be deployed within the left renal artery 878 which may be positioned lower than its corresponding right renal artery 877. The first fenestration 160 may be configured to pivot to allow the side branch prosthesis 830 to be positioned at an angle relative to the graft 112. The ability to angle the side branch prosthesis 830 may allow an off-the-shelf prosthesis, such as the prosthesis 110, to be used to treat a patient whose anatomy does not align completely with the first fenestration 160. In another example, shown in FIG. 17, the side branch prosthesis 830 may be deployed within the left renal artery 878 which may be positioned higher than its corresponding right renal artery 877. The fenestration 160 may be configured to pivot to accommodate the offset position of the left renal artery 878 and provide access to the left renal artery 878 through the use of a delivery device, such as a catheter.

Once a catheter is placed within the left renal artery 878, the side branch prosthesis 830 may be deployed within the left renal artery 878. The side branch prosthesis 830 may be balloon expandable or self-expandable. In one example, the side branch prosthesis is balloon expandable. Once the side branch prosthesis 830 is deployed within the left renal artery 878, the end of the side branch prosthesis remaining within the interior surface of the graft 112 may be flared to provide a proper seal between the fenestration 161 and the left renal artery 878.

FIGS. 18A-18L illustrate exemplary method steps for deploying the prosthesis 210. The prosthesis 210 may be positioned within the patient's aorta 860 as described above with reference to FIGS. 14A-14F. The first portion 542a of the auxiliary guide wire 542 may provide clear access to the first branch 230 and the third branch 260 of the prosthesis 210 from the brachial puncture 893 as further described below. The second portion 542b of the auxiliary guide wire 542 may provide clear access to the second branch 240 of the prosthesis 210 from the brachial puncture 893 and clear access to the fourth branch 170 of the prosthesis from the femoral puncture 891 also as further described below.

It should be noted that, in FIGS. 18A-18L, outer surfaces of the prosthesis 210 are not shown as being in contact with inner surfaces of the aorta 860 solely for illustrative purposes. In use, the graft 212 may be sized and configured so that at least an outer surface of the region proximal to the tapered portion securely engages an inner surface of the aorta 860 to hold the prosthesis 210 in place relative to the vasculature. Additional outer regions of the graft may securely engage the inner surface of the aorta 860. Optionally, additional modular prostheses may be coupled to the prostheses (e.g., extending into one or more of the iliac arteries) whereby the modular prostheses have outer surfaces dimensioned to securely engage inner surfaces of the iliac arteries or other vasculature.

Figure 18A:
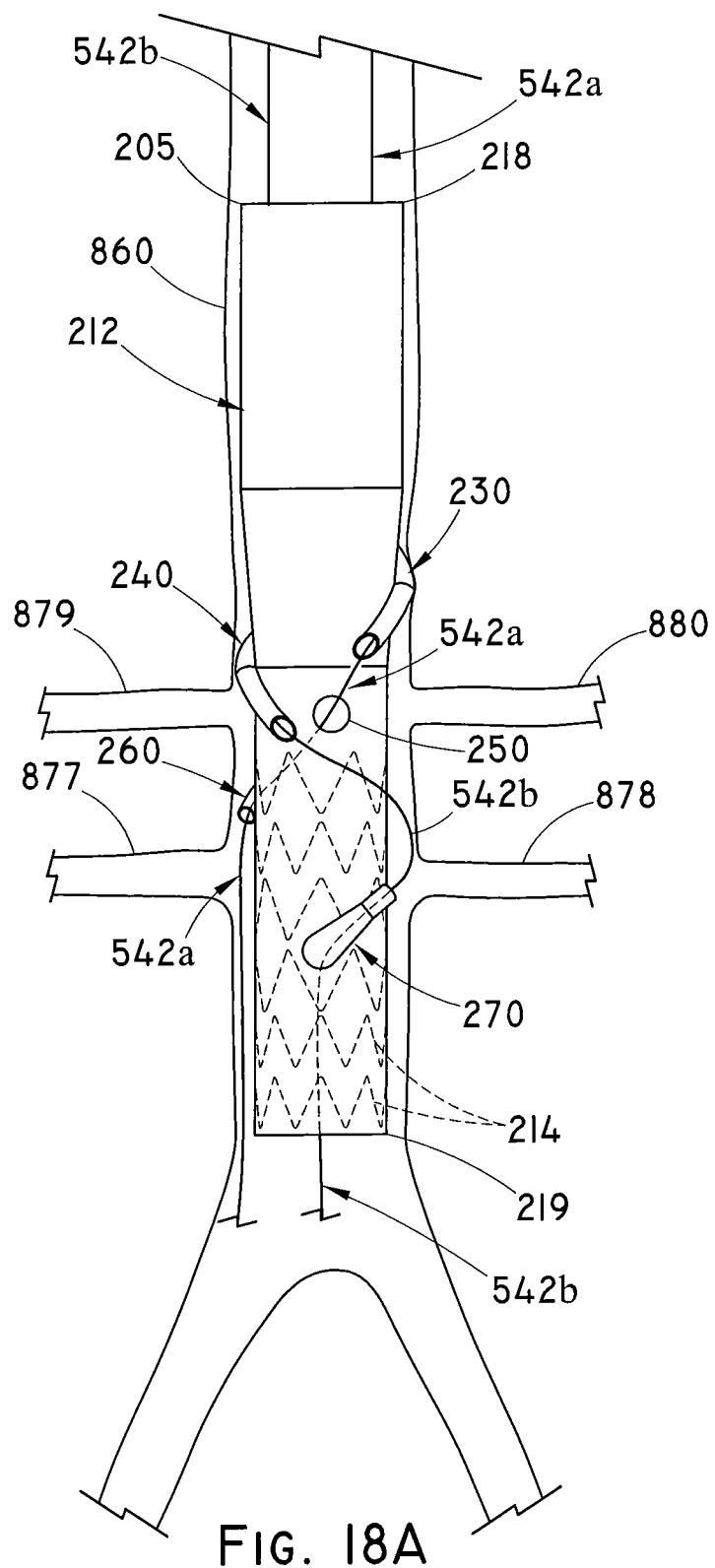
FIG. 18A illustrates the endoluminal prosthesis of FIG. 8 positioned within a thoracoabdominal aorta of a patient.
Figure 18B:
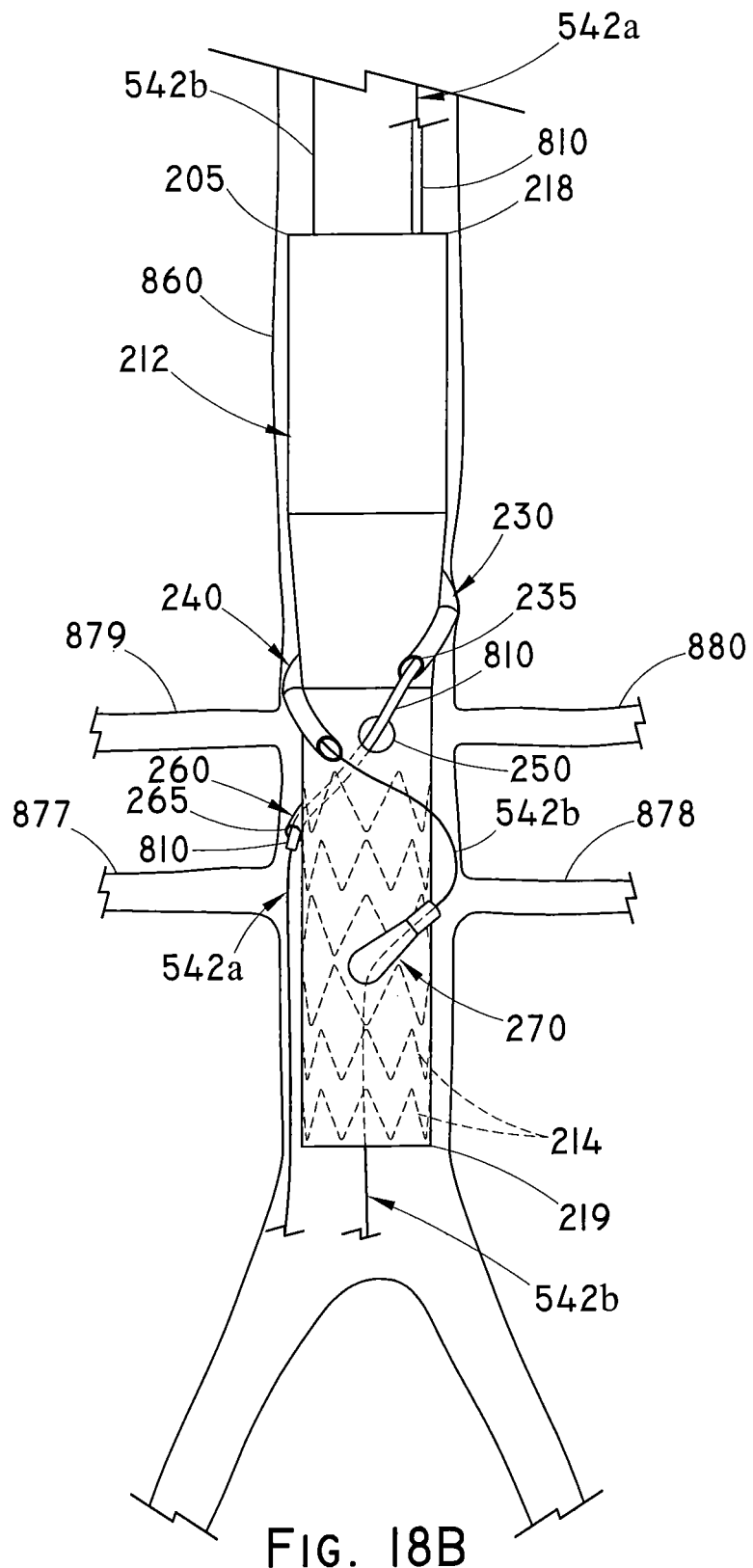
FIGS. 18B-18E illustrate exemplary method steps for deploying a branch prosthesis within one branch of the endoluminal prosthesis of FIG. 8.

Referring now to FIG. 18B, in a next step, a sheath 810 may be advanced over the first portion 542a of the auxiliary guide wire 542, in a direction from the brachial artery and distally down the aorta 860. In one example, the sheath 810 comprises a size of about 6 French. The sheath 810 may be advanced distally through the lumen 235 of the first branch 230, through the self-sealing fenestration 250, through the lumen 265 of the third branch 260, and toward the right renal artery 877, as depicted in FIG. 18B. Optionally, a dilator may be used in conjunction with the sheath 810 to facilitate advancement of the sheath 810 to the position shown in FIG. 18B. If a dilator is used, then after desired placement of the sheath 810, the dilator may be withdrawn proximally out of the patient's anatomy via the brachial artery, leaving the sheath 810 in place near the right renal artery 877.

Figure 18C:
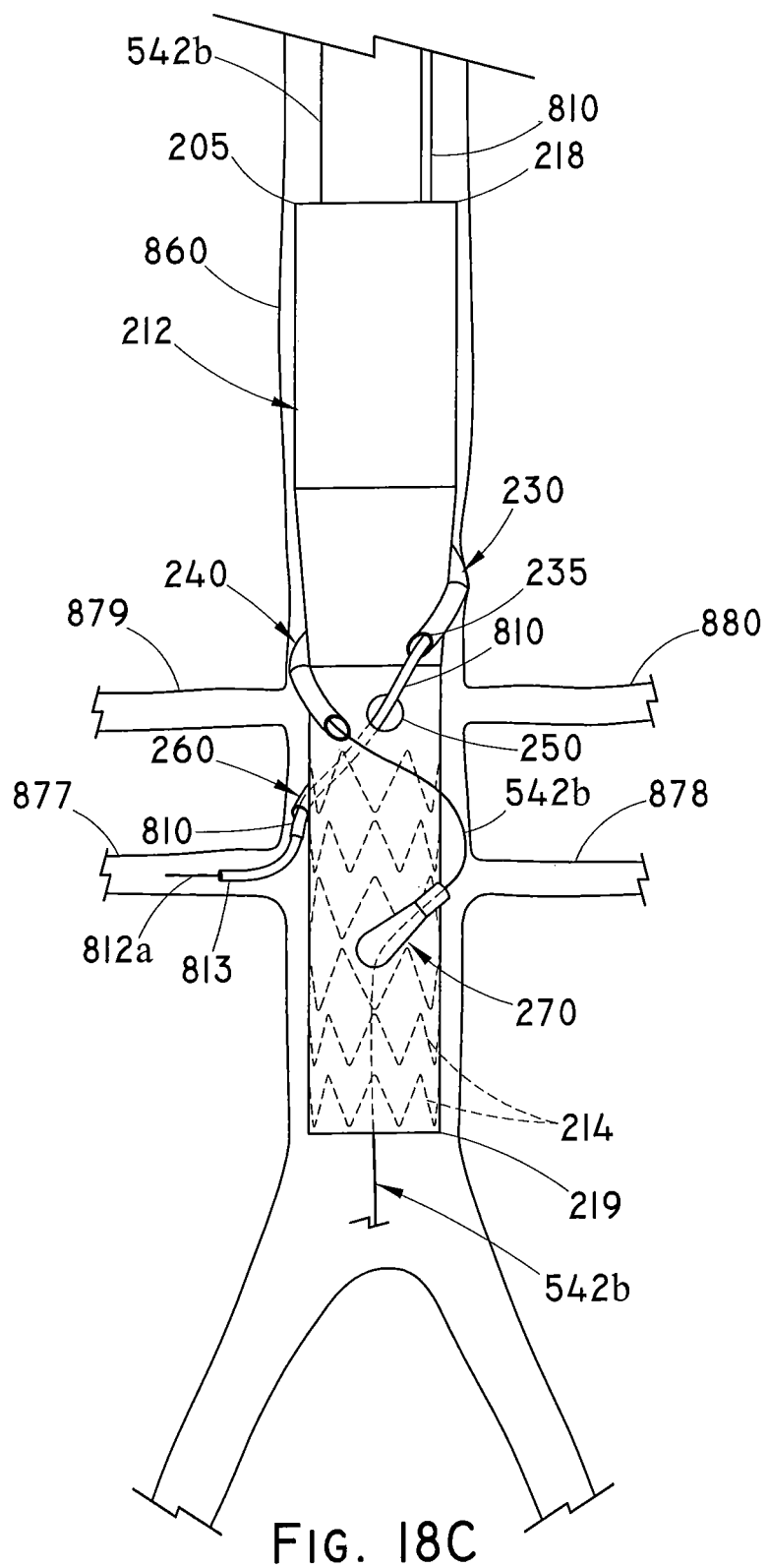
Figure 18D:
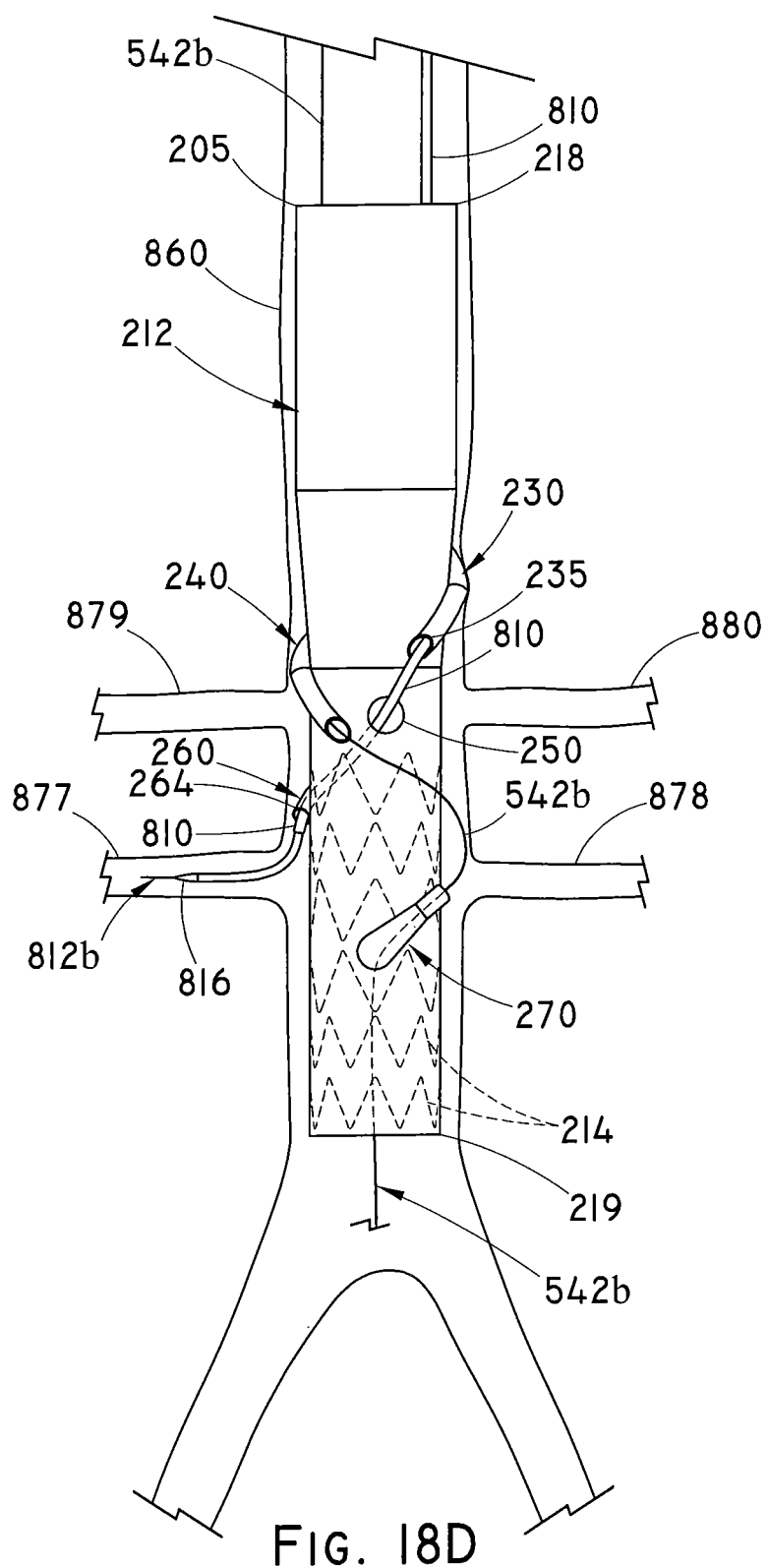

Referring now to FIG. 18C, at this stage, the first portion 542a of the auxiliary guide wire 542 can be withdrawn from the brachial artery, and another wire guide 812a may be introduced via the sheath 810. The wire guide 812a may be received within the catheter 813, which may be introduced with the wire guide 812a via the sheath 810 as described above. The catheter 813 may aid in guiding the wire guide 812a into the right renal artery 877. To that end, the catheter 813 may be advanced such that a distal end of the catheter 813 is positioned proximate the ostium of the right renal artery 877, and the wire guide 812a and the catheter 813 may be further advanced into the right renal artery 877 as shown in FIG. 18C. In one example, the first portion 542a of the auxiliary guide wire 542 may remain in place to stabilize the third branch 260 during advancement of the wire guide 812a and/or the catheter 813. The wire guide 812a may be replaced with the wire guide 812b, which may have a stiffness that is greater than a stiffness of the wire guide 812a as described above. The catheter 813 may be retracted proximally relative to the sheath 810 and removed from the patient's body. The wire guide 812b may remain in place within the right renal artery 877 as shown in FIG. 18D. The position of the wire guide 812b in the right renal artery 877 may enable delivery of a side branch prosthesis into the right renal artery 877 using any suitable endovascular delivery technique.

The further deployment device 816 can then be introduced via the sheath 810 and the wire guide 812b, such that the deployment device 816 is advanced through a length of the sheath 810 in a distal direction from the brachial artery and ultimately into the right renal artery 877 as shown in FIG. 18D. The deployment device 816 may extend out of the distal end 264 of the third branch 260 of the prosthesis 210 so that a side branch prosthesis 820 can be deployed to extend from the third branch 260 into the right renal artery 877 as shown in FIG. 18E.

Figure 18E:
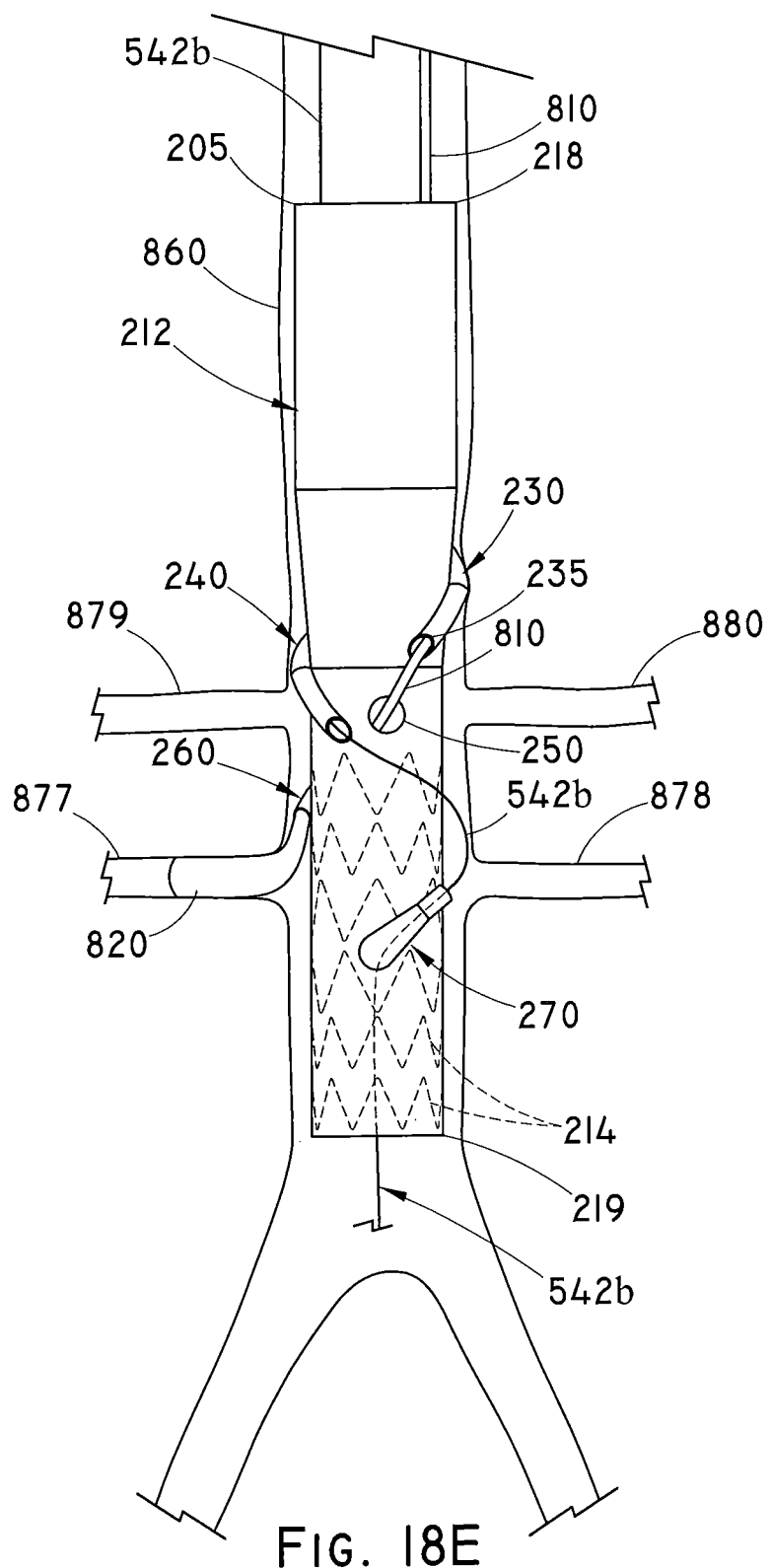

Referring to FIG. 18E, upon deployment from the deployment device 816, the side branch prosthesis 820 and the third branch 260 of the prosthesis 210 may be mated such that there is a suitable tromboning connection, preferably with a 1.5 to 2 cm overlap and a 1 mm or less difference in diameter at the interconnection. Optionally, the devices may be expanded for about 30 seconds using a suitably sized balloon dilation catheter. At this time, the side branch prosthesis 820 may provide patent fluid flow through the graft 212 into the right renal artery 877. The deployment device 816 and the wire guide 812b may be retracted proximally and removed from the patient's body.

Figure 18F:
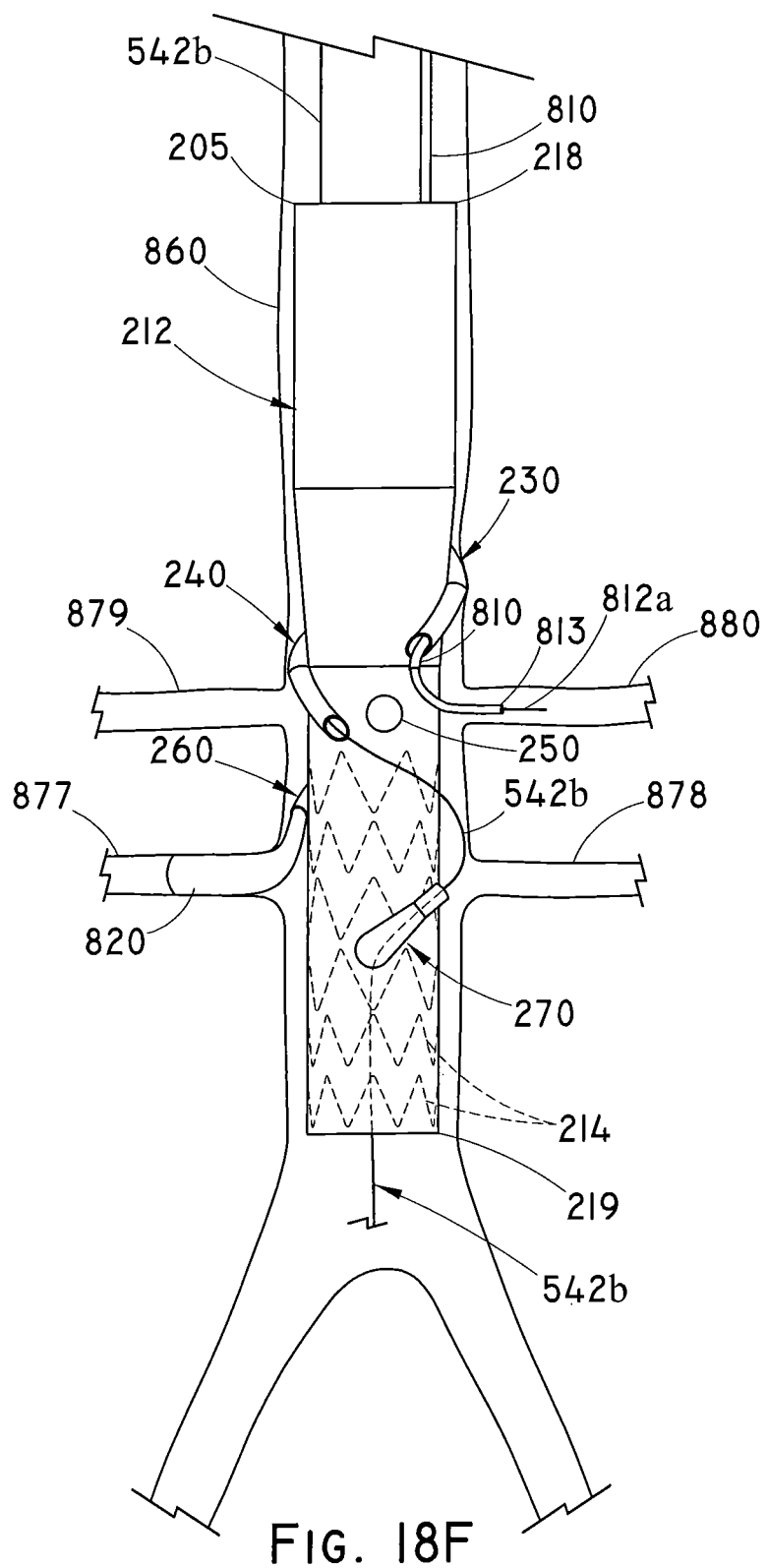
FIGS. 18F-18G illustrate exemplary method steps for deploying a branch prosthesis within another branch of the endoluminal prosthesis of FIG. 8.

Referring now to FIG. 18F, in a next step, the sheath 810 may be proximally retracted away from the right renal artery 877 and through the self-sealing fenestration 250 until the distal end of the sheath 810 is positioned just distal to the first branch 230 at a location adjacent to the celiac artery 880. Notably, the self-sealing fenestration 250 may become closed without leakage upon removal of various components (e.g., the first portion 542a of the auxiliary guide wire 542, the wire guides 812a, 812b, the deployment device 816, and/or the sheath 810), as explained above. The wire guide 812a, or another wire guide, then may be advanced from the sheath 810 in a distal direction into the celiac artery 880, as shown in FIG. 18F. The wire guide 812a may be received within the catheter 813, or another catheter, which may be introduced with the wire guide 812a via the sheath 810 as described above. The catheter 813 may aid in guiding the wire guide 812a into the celiac artery 880. To that end, the catheter 813 may be advanced such that the distal end of the catheter 813 is positioned proximate the ostium of the celiac artery 880, and the wire guide 812a and the catheter 813 may be further advanced into the celiac artery 880 as shown in FIG. 18F. The wire guide 812a may be replaced with the wire guide 812b, or another wire guide, which may have a stiffness that is greater than a stiffness of the wire guide 812a as described above. The catheter 813 may be retracted proximally relative to the sheath 810 and removed from the patient's body, and the wire guide 812b may remain in place within the celiac artery 880. The position of the wire guide 812b in the celiac artery 880 may enable delivery of a side branch prosthesis into the celiac artery 880 using any suitable endovascular delivery technique.

Figure 18G:
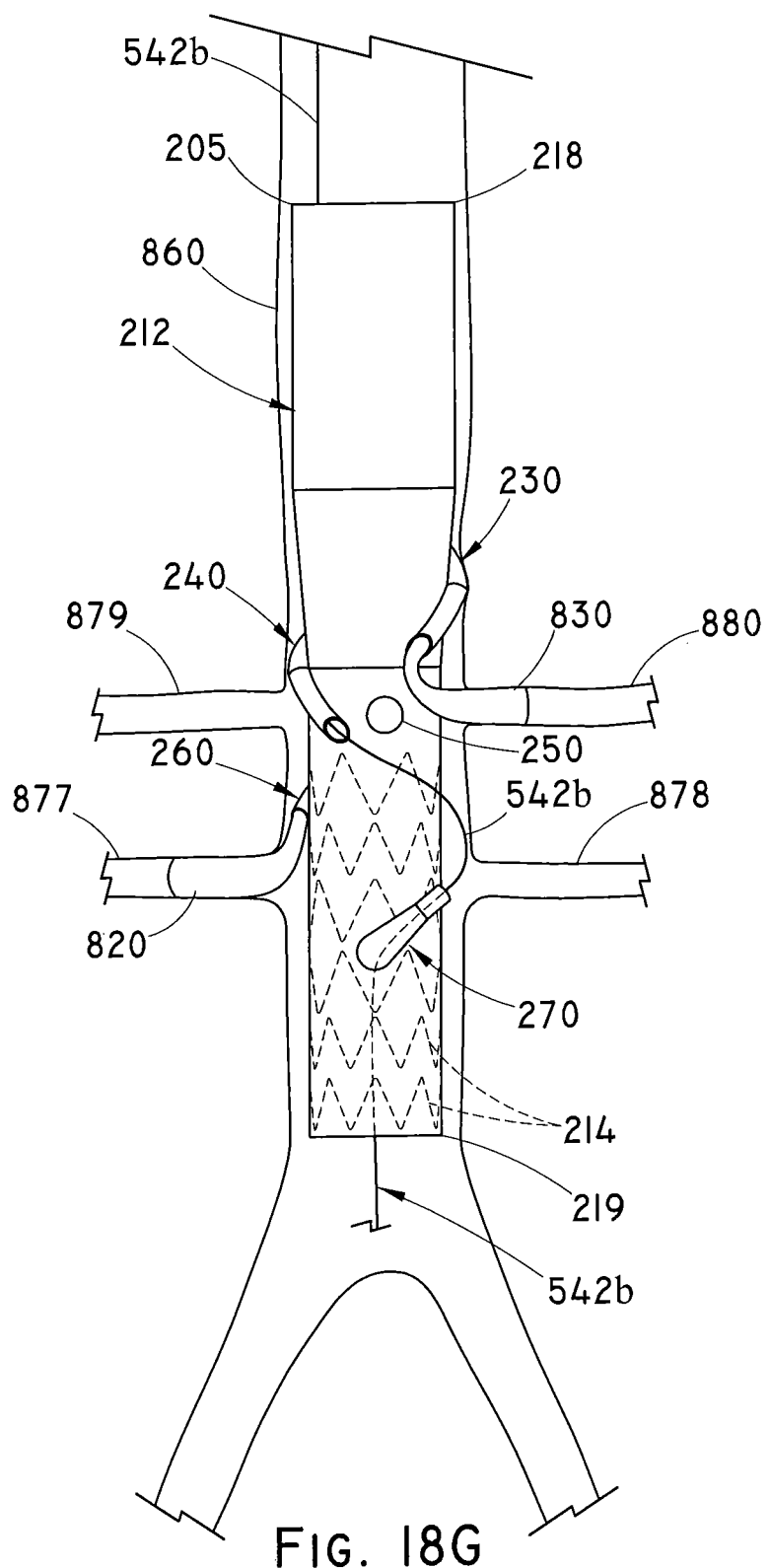

Referring now to FIG. 18G, in a next step, the sequence shown in FIGS. 18D-18E may be repeated whereby the deployment device 816, or another deployment device, may be introduced via the sheath 810 and the wire guide 812b in a distal direction from the brachial artery and ultimately into the celiac artery 880. The deployment device 816 may extend out of the distal end 234 of the first branch 230 of the prosthesis 210 so that a side branch prosthesis 830 can be deployed to extend from the first branch 230 into the celiac artery 880. Upon deployment from the deployment device 816, the side branch prosthesis 830 and the first branch 230 of the prosthesis 210 may be mated such that there is a suitable tromboning connection in the manner described above. At this time, the side branch prosthesis 830 may provide patent fluid flow through the graft 212 into the celiac artery 880, and the deployment device 816, the sheath 810, and the wire guide 812b may be removed from the patient's body, as shown in FIG. 18G.

Figure 18H:
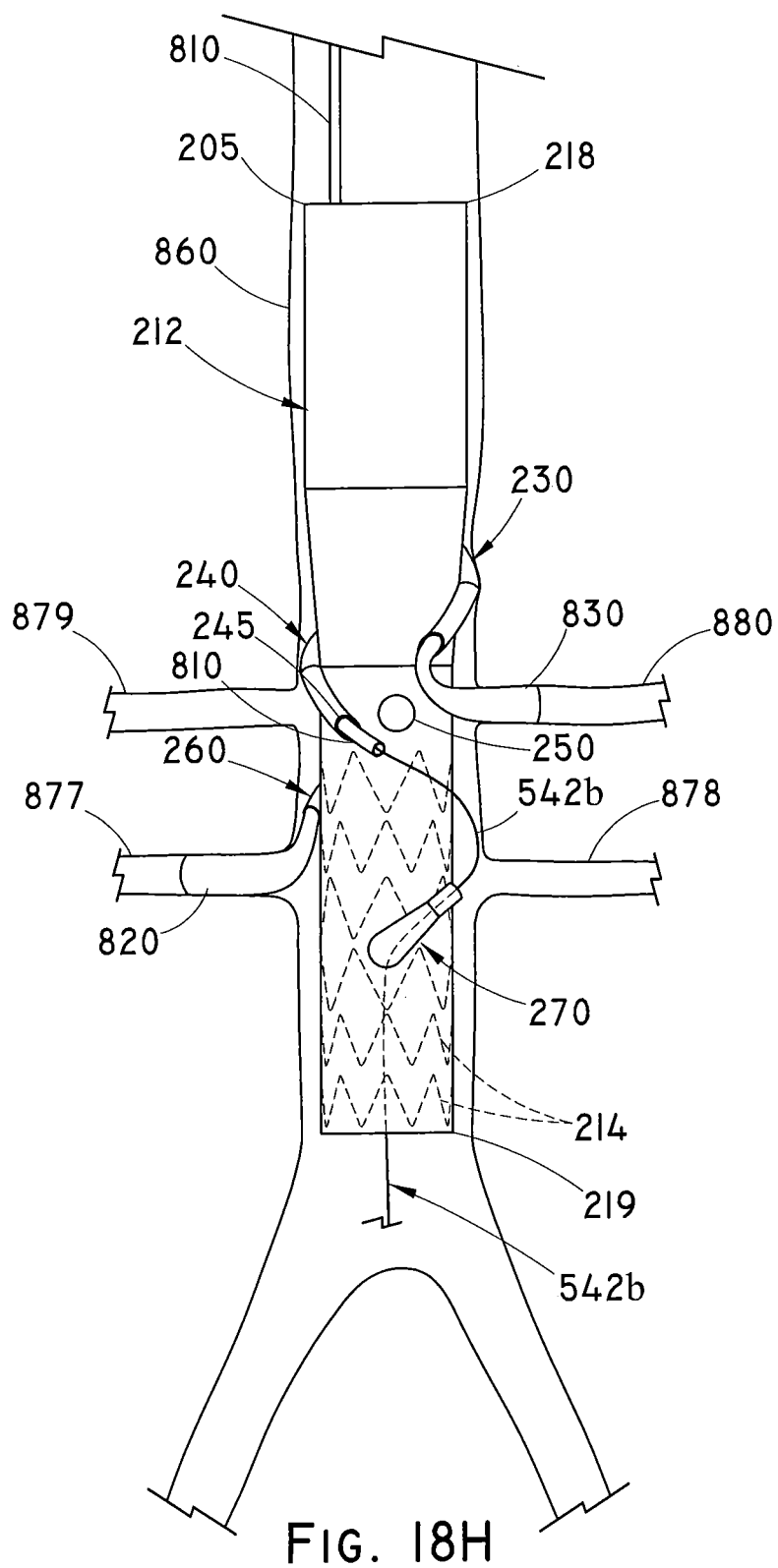
FIGS. 18H-18J illustrate exemplary method steps for deploying a branch prosthesis within another branch of the endoluminal prosthesis of FIG. 8.

Referring now to FIG. 18H, in a next step, the sheath 810, or another sheath, and optional dilator may be advanced over the second portion 542b of the auxiliary guide wire 542, in a direction from the brachial artery and distally down the aorta 860. The sheath 810 and optional dilator may be advanced distally through the lumen 245 of the second branch 240, and disposed adjacent to the superior mesenteric artery 879, as depicted in FIG. 18H.

Figure 18I:
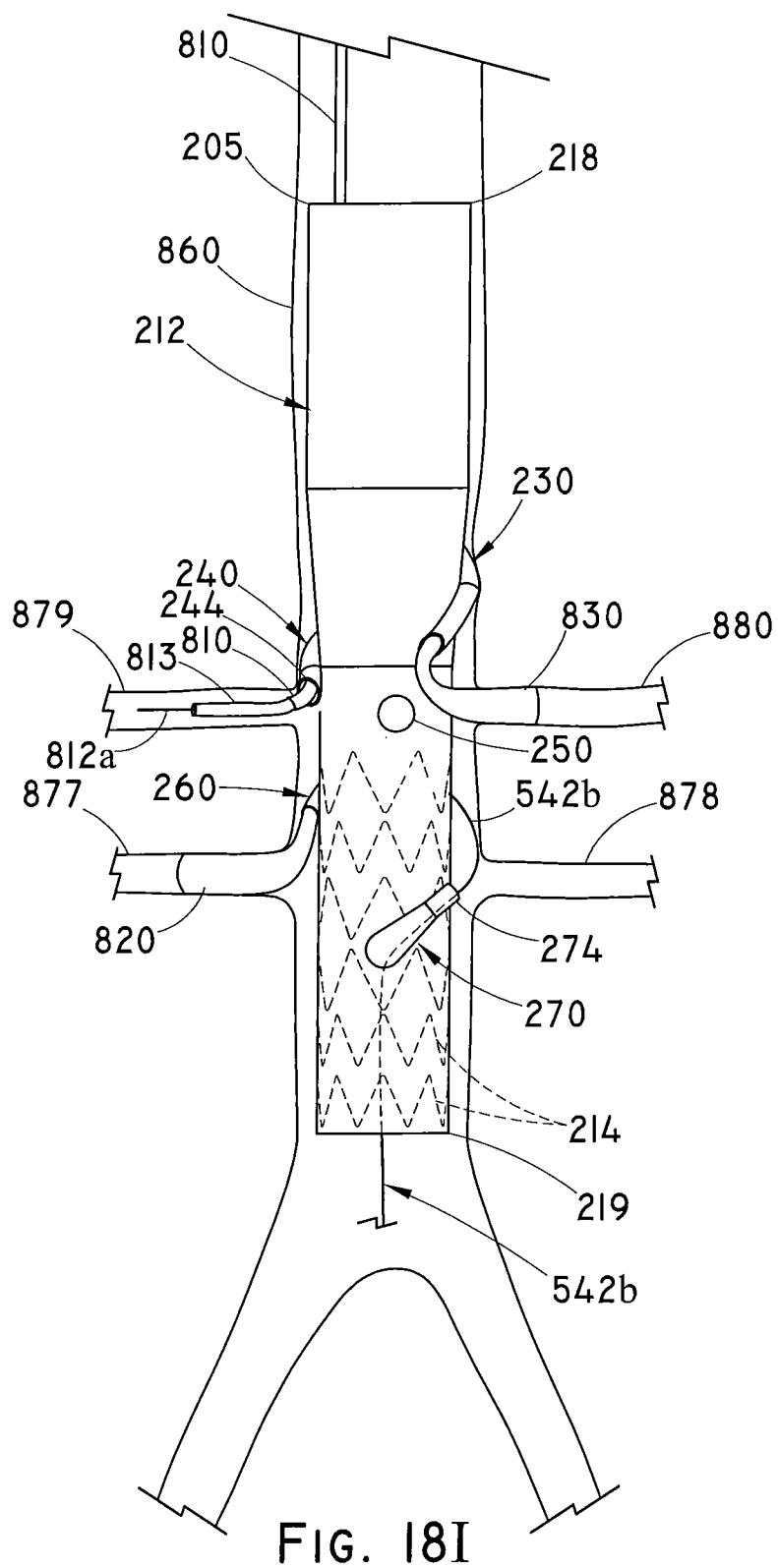

Referring to FIG. 18I, in a next step, the second portion 542b of the auxiliary guide wire 542 may be retracted distally away from the brachial artery, such that the most proximal region of the second portion 542b of the auxiliary guide wire 542 is positioned at a location outside of the graft 212 between the distal end 244 of the second branch 240 and the distal end 274 of the fourth branch 270. The wire guide 812a, or another wire guide, and the catheter 813, or another catheter, then may be advanced from the sheath 810 in a distal direction and into the superior mesenteric artery 879 to cannulate the superior mesenteric artery 879. The wire guide 812a may be replaced with the wire guide 812b, or another wire guide, and the catheter 813 may be removed from the patient's body as described above. Notably, the distal end 244 of the second branch 240 may accommodate positioning of the wire guide 812a and the catheter 813 since the second portion 542b of the auxiliary guide wire 542 has been withdrawn from an overlapping relationship with the second branch 240. The position of the wire guide 812b in the superior mesenteric artery 879 may enable delivery of a side branch prosthesis into the superior mesenteric artery 879 using any suitable endovascular delivery technique.

Figure 18J:
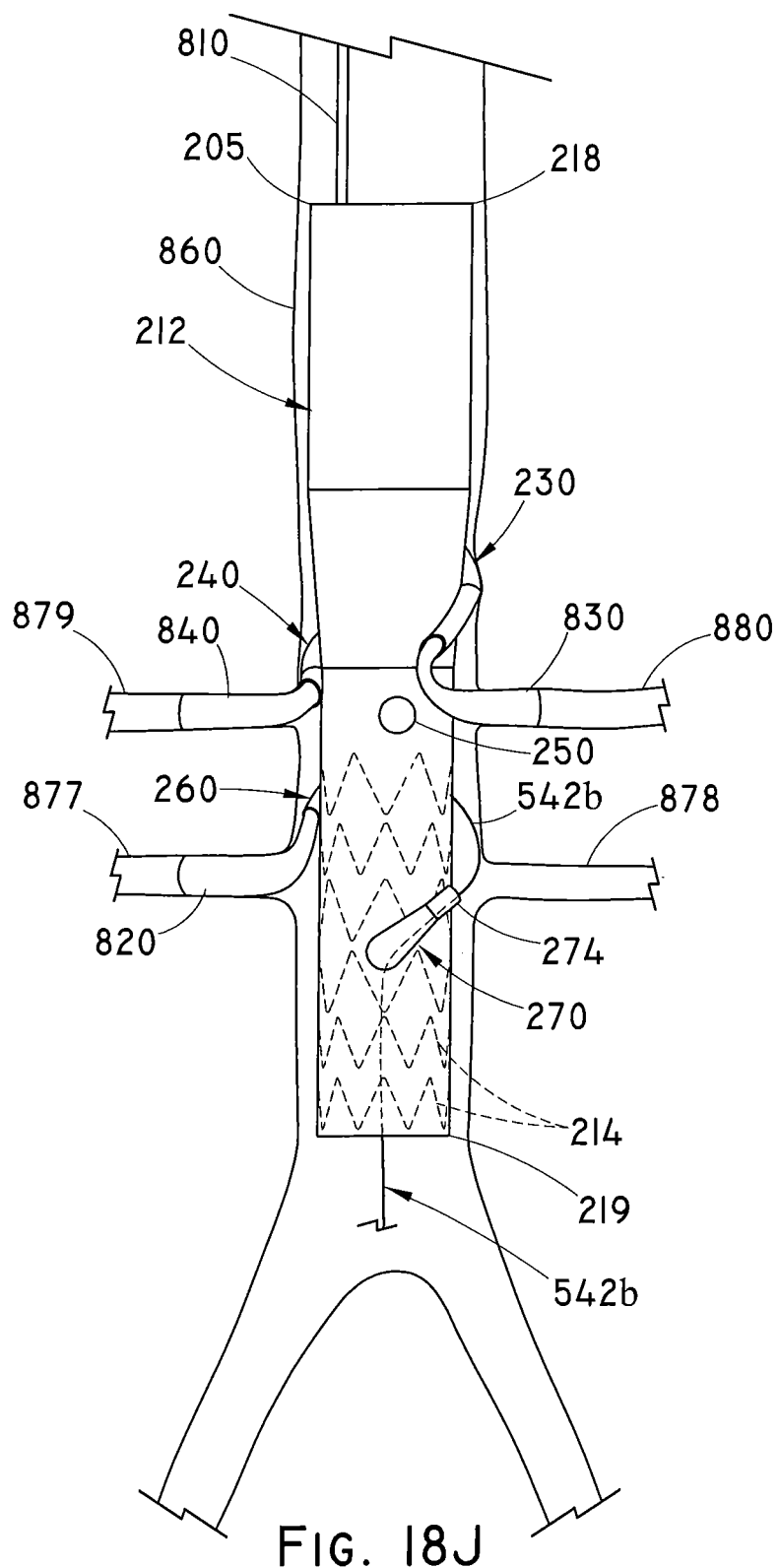

Referring now to FIG. 18J, in a next step, the sequence shown in FIGS. 18D-18E may be repeated whereby the deployment device 816, or another deployment device, may be introduced via the sheath 810 and the wire guide 812b in a distal direction from the brachial artery and ultimately into the superior mesenteric artery 879. The deployment device 816 may extend out of the distal end 244 of the second branch 240 of the prosthesis 210 so that a side branch prosthesis 840 can be deployed to extend from the second branch 240 of the prosthesis 210 into the superior mesenteric artery 879. Upon deployment from the deployment device 816, the side branch prosthesis 840 and the second branch 240 of the prosthesis 210 may be mated such that there is a suitable tromboning connection in the manner described above. At this time, the side branch prosthesis 840 may provide patent fluid flow through the graft 212 into the superior mesenteric artery 879, as shown in FIG. 18J. The deployment device 816, the sheath 810, and the wire guide 812b then may be withdrawn proximally out of the patient's body via the brachial artery.

Figure 18K:
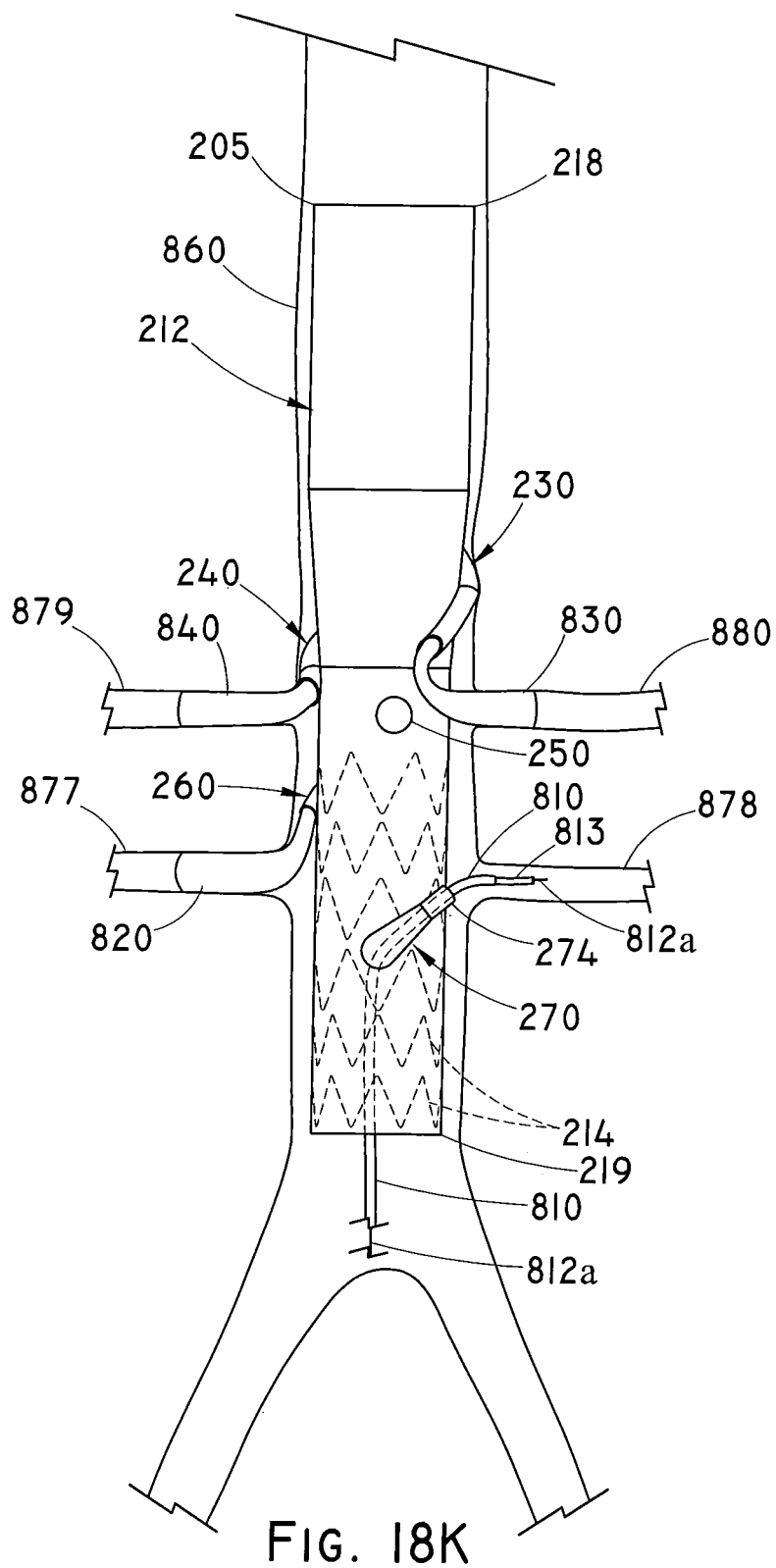
FIGS. 18K-18L illustrate exemplary method steps for deploying a branch prosthesis within another branch of the endoluminal prosthesis of FIG. 8.

Since the proximal region of the second portion 542b of the auxiliary guide wire 542 is now positioned adjacent to the left renal artery 878, as shown in FIG. 18J, the sheath 810, or another sheath, and the optional dilator then may be advanced over the distal region of the second portion 542b of the auxiliary guide wire 542 in a direction from the femoral artery and proximally up the aorta 860. The sheath 810 and the optional dilator may be advanced distally through the lumen 275 of the fourth branch 270 (i.e., proximally relative to the graft 212), and toward the left renal artery 878 as shown in FIG. 18K. The optional dilator then may be withdrawn distally out of the patient's anatomy via the femoral artery, leaving the sheath 810 in place near the left renal artery 878.

Figure 18L:
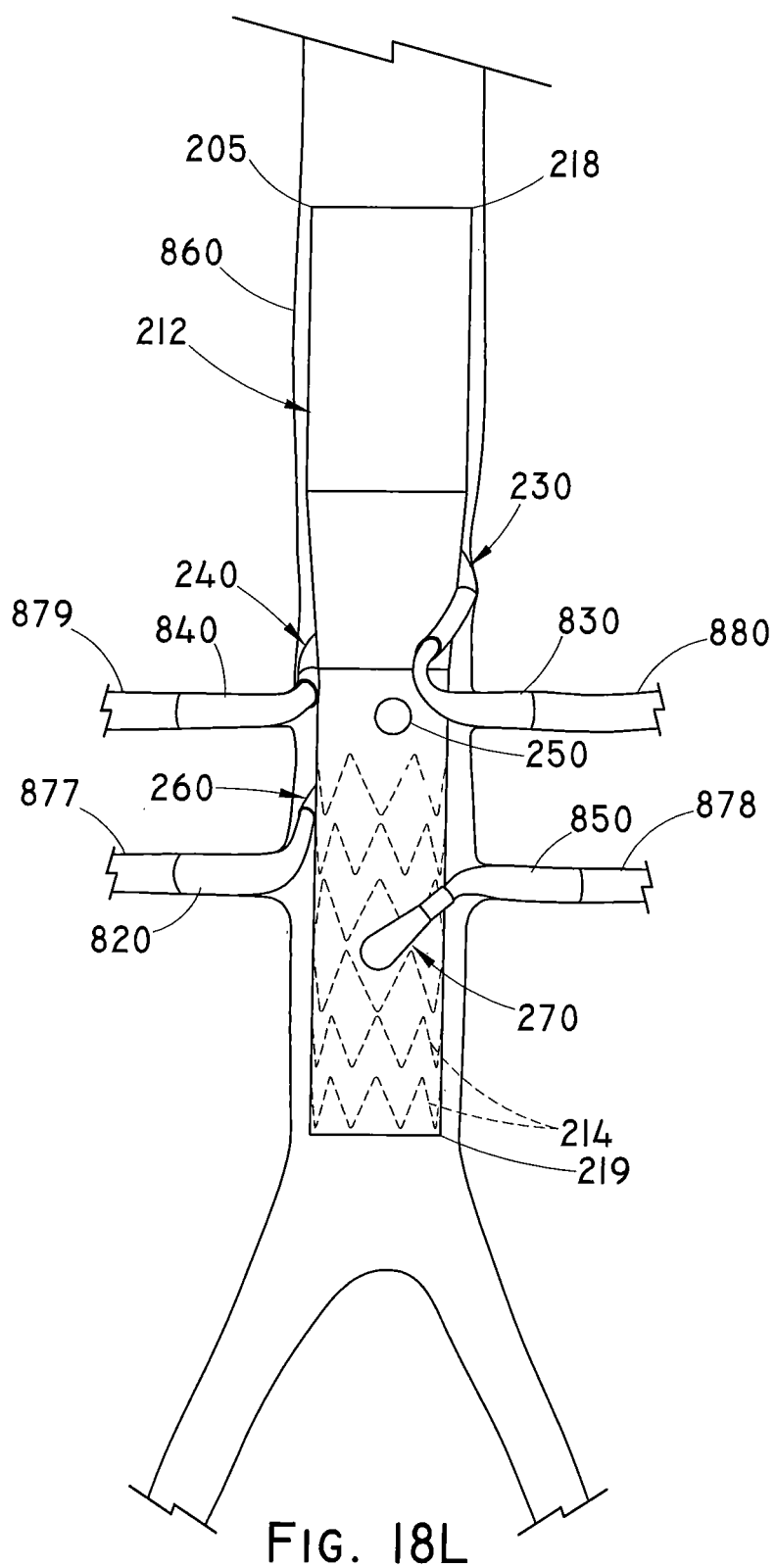

Referring to FIG. 18K, with the sheath 810 disposed near the left renal artery 878, the second portion 542b of the auxiliary guide wire 542 may be removed distally through the sheath 810, and the wire guide 812a, or another wire guide, and the catheter 813, or another catheter, then may be advanced through the sheath 810 in a proximal direction relative to the graft 212, distally through the fourth branch 270, and into the left renal artery 878 to cannulate the left renal artery 878. The wire guide 812a may be replaced with the wire guide 812b, or another wire guide, and the catheter 813 may be removed from the patient's body as described above. Then, the sequence shown in FIGS. 18D-18E may be repeated whereby the deployment device 816, or another deployment device, may be introduced via the sheath 810 and the wire guide 812b in a proximal direction from the femoral artery and ultimately into the left renal artery 878. The deployment device 816 may extend out of the distal end 274 of the fourth branch 270 of the prosthesis 210 so that a side branch prosthesis 850 can be deployed to extend from the fourth branch 270 into the left renal artery 878. Upon deployment from the deployment device 816, the side branch prosthesis 850 and the fourth branch 270 of the prosthesis 210 may be mated such that there is a suitable tromboning connection in the manner described above. At this time, the side branch prosthesis 850 may provide patent fluid flow through the graft 212 into the left renal artery 878, as shown in FIG. 18L. The deployment device 818, the sheath 810, and the wire guide 812b then may be withdrawn distally out of the patient's body via the femoral artery.

The configuration and placement of the various branches 230, 240, 260, 270 along the graft 212, together with the self-sealing fenestration 250, may provide the ability to manipulate the first and second portions 542a, 542b of the auxiliary guide wire 542 and the delivery components in a manner that will allow for relatively quick delivery of four different side branch prostheses. The preloaded system provided by the present embodiments may save multiple steps and significant time during a surgical operation.

It will be appreciated that the exact number, orientation, and placement of the various branches and or fenestrations along the graft may be varied without departing from the spirit of the present embodiments. Moreover, while one exemplary procedure has been described with reference to the thoracoabdominal aorta and its branches, a graft having multiple branches and/or fenestrations as described herein may be used in other procedures, and particularly those that may benefit from a preloaded arrangement to facilitate insertion of delivery components into the various branches and/or fenestrations. Moreover, alternative systems may include greater or fewer branches, fenestrations, and/or wires than shown herein. For example, in an alternative embodiment, a system for facilitating deployment of an endoluminal prosthesis may include the graft 212, the first and third branches 230, 260 extending radially outward from the graft, and a wire extending through the lumens of the first and third branches 230, 260 in the preloaded configuration. The second and fourth branches 240, 270 may be omitted in this example, such that only two branches and one wire segment are provided. In alternative embodiments, any number of branches, any number of fenestrations, and any number of wires may be provided without departing from the spirit of the present embodiments.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A prosthesis system comprising:
    a delivery system;
    a prosthesis, comprising:
    a tubular body of biocompatible graft material having a proximal end, a distal end, an inner lumen, a sidewall, and a longitudinal axis from the proximal end to the distal end;
    a proximal portion having a first diameter;
    a distal portion having a second diameter;
    a tapered portion between the proximal portion and the distal portion;
    a first fenestration in the sidewall of the tapered portion;
    a second fenestration in the sidewall of the tapered portion;
    a first antegrade portal connected to and extending entirely longitudinally from the first fenestration and having an inner lumen and a distally extending open end, the first portal disposed at least partially in the tapered portion and configured to permit antegrade flow therethrough;
    a second antegrade portal connected to and extending entirely longitudinally from the second fenestration and having an inner lumen and a distally extending open end, the second portal disposed at least partially in the tapered portion and configured to permit antegrade flow therethrough;
    a first auxiliary guide preloaded in the prosthesis prior to delivery to a patient, wherein a portion of the first auxiliary guide extends through the inner lumen of the prosthesis and through the inner lumen the first antegrade portal and a portion extends beyond the proximal end of the prosthesis; and
    a second auxiliary guide preloaded in the prosthesis prior to delivery to a patient, wherein a portion of the second auxiliary guide extends through the inner lumen of the prosthesis and through the inner lumen the second antegrade portal.

2. The system of claim 1, wherein the first and second auxiliary guides comprise first and second auxiliary guide wires.

3. The system of claim 2, further comprising first and second auxiliary sheaths preloaded in the prosthesis.

4. The system of claim 1, wherein a portion of the first auxiliary guide extends out of the distally extending open end of the first portal.

5. The system of claim 4, wherein a portion of the second auxiliary guide extends out of the distally extending open end of the second portal.

6. The system of claim 1, further including an access sheath, wherein the access sheath is disposed at least partially proximal of the prosthesis and is configured to be introduced through the right brachial artery, the left brachial artery, or the axillary artery.

7. The system of claim 6, where the first and second auxiliary guides are configured to extend to and through the access sheath.

8. The system of claim 1, further including an access hub and an access sheath extending from the access hub, wherein the access hub is disposed proximal of the access sheath and is configured to receive the first and second auxiliary guides.

9. The system of claim 1, wherein each of the first antegrade portal, the second antegrade portal, the third antegrade portal and the fourth portal is configured to receive a prosthesis.

10. The system of claim 1, wherein the delivery system comprises a tapered nose cone and a portion of each of the first and second guides extends to the nose cone.

11. The system of claim 1, wherein a portion of the first and second auxiliary guides extends distally of the distally extending open ends of the first and second antegrade portals and along an exterior surface of the prosthesis.

12. A prosthesis system comprising:
a delivery device;
a prosthesis retained on the delivery device, comprising:
a tubular body of biocompatible graft material having a proximal end, a distal end, an internal lumen, a sidewall, and a longitudinal axis from the proximal end to the distal end;
a proximal portion having a first diameter;
a distal portion having a second diameter;
a tapered portion between the proximal portion and the distal portion;
first and second antegrade portals extending entirely longitudinally and parallel to the longitudinal axis, each portal having a distally extending open end perpendicular to the longitudinal axis, the first and second antegrade portals disposed at least partially in the tapered portion and configured to permit antegrade fluid flow therethrough;
first and second auxiliary guides preloaded within the prosthesis prior to delivery to a patent, wherein the first auxiliary guide extends through the distally extending open end of the first antegrade portal, through the inner lumen of the first antegrade portal, through the inner lumen of the prosthesis and toward the proximal end of the prosthesis; and wherein the second auxiliary guide extends through the distally extending open end of the second antegrade portal, through the inner lumen of the second antegrade portal, through the inner lumen of the prosthesis and toward the proximal end of the prosthesis.

13. The system of claim 12, wherein the first and second auxiliary guides comprise first and second auxiliary guide wires.

14. The system of claim 13, further comprising first and second auxiliary sheaths preloaded in the prosthesis.

15. The system of claim 12, further including an access sheath, wherein the access sheath is disposed at least partially proximal of the prosthesis and is configured to be introduced through the right brachial artery, the left brachial artery, or the axillary artery.

16. The system of claim 15, where the first and second auxiliary guides are configured to extend to and through the access sheath.

17. The system of claim 12, wherein the delivery device comprises a tapered nose cone and a portion of each of the first and second auxiliary guides extends to the nose cone.

18. The system of claim 12, wherein a portion of the first and second auxiliary guides extends distally of the distally extending open ends of the first and second antegrade portals and along an exterior surface of the prosthesis.

19. A prosthesis system comprising:
a delivery device;
a prosthesis retained on the delivery device, comprising:
a tubular body of biocompatible graft material having a proximal end, a distal end, an internal lumen, a sidewall, and a longitudinal axis from the proximal end to the distal end;
a proximal portion having a first diameter;
a distal portion having a second diameter;
a tapered portion between the proximal portion and the distal portion;
first and second antegrade portals extending entirely longitudinally and parallel to the longitudinal axis, each portal having a distally extending open end perpendicular to the longitudinal axis, the first and second antegrade portals disposed at least partially in the tapered portion and configured to permit antegrade fluid flow therethrough;
first and second auxiliary guide wires preloaded within the prosthesis prior to delivery to a patent, wherein the first auxiliary guide wire extends along an outer surface of the prosthesis, through the distally extending open end of the first antegrade portal, through the inner lumen of the first antegrade portal, through the inner lumen of the prosthesis, toward the proximal end of the prosthesis and out of the proximal end of the prosthesis; and wherein the second auxiliary guide wire extends along the outer surface of the prosthesis, through the distally extending open end of the second antegrade portal, through the inner lumen of the second antegrade portal, through the inner lumen of the prosthesis toward the proximal end of the prosthesis and out of the proximal end of the prosthesis.

20. The system of claim 19, further comprising first and second auxiliary sheaths preloaded in the prosthesis prior to delivery to a patient.

* * * * *